(12) United States Patent
Ishiwata et al.

(10) Patent No.: US 8,259,167 B2
(45) Date of Patent: Sep. 4, 2012

(54) SCATTERING MEDIUM INTERNAL OBSERVATION APPARATUS, IMAGE PICKUP SYSTEM, IMAGE PICKUP METHOD AND ENDOSCOPE APPARATUS

(75) Inventors: Hiroshi Ishiwata, Hachioji (JP);
Hiroyuki Nishida, Sagamihara (JP);
Keiji Handa, Hachioji (JP); Kenji Harano, Hachioji (JP); Daisuke Asada, Hachioji (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 972 days.

(21) Appl. No.: 12/207,239

(22) Filed: Sep. 9, 2008

(65) Prior Publication Data
US 2009/0009595 A1 Jan. 8, 2009

Related U.S. Application Data

(63) Continuation of application No. PCT/JP2007/053926, filed on Mar. 1, 2007.

(30) Foreign Application Priority Data

| | | | |
|---|---|---|---|
| Mar. 13, 2006 | (JP) | | 2006-068289 |
| Mar. 15, 2006 | (JP) | | 2006-071198 |
| Mar. 16, 2006 | (JP) | | 2006-073181 |
| Mar. 28, 2006 | (JP) | | 2006-088781 |
| Mar. 28, 2006 | (JP) | | 2006-088782 |

(51) Int. Cl.
*A62B 1/04* (2006.01)
*A61B 1/04* (2006.01)

(52) U.S. Cl. ............................................ 348/65; 348/68
(58) Field of Classification Search ..................... 348/65
See application file for complete search history.

(56) References Cited

U.S. PATENT DOCUMENTS

| | | | |
|---|---|---|---|
| 5,305,759 A | | 4/1994 | Kaneko et al. |
| 5,374,953 A | * | 12/1994 | Sasaki et al. ..................... 348/65 |
| 2002/0175993 A1 | * | 11/2002 | Ueno et al. ....................... 348/68 |

(Continued)

FOREIGN PATENT DOCUMENTS

DE 195 25 995 C1 7/1996

(Continued)

OTHER PUBLICATIONS

Supplementary European Search Report dated Nov. 3, 2011 from corresponding European Patent Application No. EP 07 73 7606.9.

*Primary Examiner* — Firmin Backer
*Assistant Examiner* — James Edwards
(74) *Attorney, Agent, or Firm* — Scully, Scott, Murphy & Presser, P.C.

(57) ABSTRACT

A scattering medium internal observation apparatus according to the present invention includes: a light source; an illuminating apparatus that guides light from the light source to an observation object that is a scattering body; and an observation optical system for observing the observation object illuminated by the illuminating apparatus, wherein the illuminating apparatus has a light-guiding member that guides light from the light source to a surface of the observation object, and a light-shielding member that covers the surface of the observation object and which shields light reflected or scattered in the vicinity of the light-guiding member of the observation object is disposed in the vicinity of an end portion of the light-guiding member on an observation object-side.

80 Claims, 34 Drawing Sheets

U.S. PATENT DOCUMENTS

| | | |
|---|---|---|
| 2004/0092829 A1 | 5/2004 | Furnish et al. |
| 2004/0140425 A1 | 7/2004 | Iizuka et al. |
| 2004/0257438 A1* | 12/2004 | Doguchi et al. ............... 348/65 |
| 2005/0014995 A1 | 1/2005 | Amundson et al. |

FOREIGN PATENT DOCUMENTS

| | | |
|---|---|---|
| JP | 63-136015 | 6/1988 |
| JP | 63-143022 | 6/1988 |
| JP | 63-214229 | 9/1988 |
| JP | 04-189349 | 7/1992 |
| JP | 06-022968 | 2/1994 |
| JP | 2528104 | 6/1996 |
| JP | 10-216080 | 8/1998 |
| JP | 2000-339445 | 12/2000 |
| JP | 2002-263055 | 9/2002 |
| JP | 2003-010189 | 1/2003 |
| JP | 2004-166913 A | 6/2004 |
| JP | 2004-237051 | 8/2004 |
| JP | 2005-000640 A | 1/2005 |
| JP | 2005-507731 | 3/2005 |
| JP | 2005-192945 | 7/2005 |
| JP | 2005-261826 | 9/2005 |
| JP | 2006-505360 | 2/2006 |
| WO | WO 03/039350 A2 | 5/2003 |
| WO | WO 2004/043251 A1 | 5/2004 |

* cited by examiner

- - - : ILLUMINATING LIGHT IRRADIATION REGION
▨ : INVISIBLE REGION

SCATTERING MEDIUM INTERNAL OBSERVATION APPARATUS, IMAGE PICKUP SYSTEM, IMAGE PICKUP METHOD AND ENDOSCOPE APPARATUS

CROSS REFERENCE TO RELATED APPLICATION

This application is a continuation application of PCT/JP2007/053926 filed on Mar. 1, 2007 and claims benefit of Japanese Applications No. 2006-068289 filed in Japan on Mar. 13, 2006, No. 2006-071198 filed in Japan on Mar. 15, 2006, No. 2006-073181 filed in Japan on Mar. 16, 2006, No. 2006-088781 filed in Japan on Mar. 28, 2006, and No. 2006-088782 filed in Japan on Mar. 28, 2006, the entire contents of each of which are incorporated herein by their reference.

BACKGROUND OF THE INVENTION

1. Field of the Invention

The present invention relates to a technique for optically observing an observation object site within a living body, and in particular, to a scattering medium internal observation apparatus, an image pickup system, an image pickup method and an endoscope apparatus for observing blood vessels, nerves and the like existing within a living body.

2. Description of the Related Art

When performing a surgical operation such as a removal of a diseased portion, the operation proceeds while being aware of positions of circulatory organs such as blood vessels and lymph channels as well as nerves in order to avoid damaging the same. During such an operation, a surgeon-in-charge must have intimate anatomical knowledge of positions of blood vessels and the like. In particular, it is essential that locations of blood vessels are identified.

However, the arrangement and distribution of blood vessels and the like vary between individuals. Accordingly, since it is required that an operation be performed while cautiously identifying the positions of blood vessels, surgeries tend to be prolonged.

A prolonged surgery leads to an increased burden on the patient. In order to reduce the burden to be borne by the patient, a method is required which enables positions of blood vessels and the like to be identified regardless of differences in the distribution of blood vessels and the like between individuals.

As a method for obtaining positional information on blood vessels, a vein authentication technique is disclosed in Japanese Patent Application Laid-Open Publication No. 2000-339445.

The disclosed vein authentication technique identifies individuals using differences in vascular arrangement and distribution which exist between individuals, and is applied to information security management as an alternative to personal identification numbers and passwords used for information management.

The vein authentication technique disclosed in Japanese Patent Application Laid-Open Publication No. 2000-339445 is a technique for detecting a vein existing in the vicinity of palmar skin using light absorption characteristics of blood hemoglobin. A palm is irradiated with a light having a wavelength band of 700 to 1000 nm for which blood hemoglobin has light absorption characteristics, whereby the arrangement and distribution of veins in the vicinity of skin are detected based on distribution information of differences in intensities of irradiated light and returned light.

In addition, there conventionally exists a method for observing an observation object site by reducing the influence of scattering by tissue in the vicinity of a living body surface when observing the inside from the surface or the influence of matter existing between an observation apparatus and the observation object site, as well as a method for observing an observation object site using pulsed light in an infrared wavelength.

For example, a technique disclosed in Japanese Patent Application Laid-Open Publication No. H06-022968 aims to reduce the influence of scattered light by synchronizing with a pulsed light generated by a light source and temporarily picking up an image transmitted from image transmitting means using instantaneous image pickup means.

Furthermore, a technique disclosed in Japanese Patent Application Laid-Open Publication No. 2005-261826 involves observing an observation object using a terahertz-range wavelength generated using an infrared pulsed laser.

Furthermore, in recent years, a device is proposed which is capable of obtaining, for example, the number of blood hemoglobin, a state of vascular flow, or the like as information regarding the inside of a living body tissue by irradiating the living body tissue with infrared light having a wavelength band that corresponds to light absorption characteristics of blood vessels, blood, and the like.

As a device capable of obtaining information regarding the inside of a living body tissue as described above, for example, there is a vascular visualization method proposed in Japanese Patent Application Laid-Open Publication No. 2004-237051.

The vascular visualization method proposed in Japanese Patent Application Laid-Open Publication No. 2004-237051 enables a state of vascular flow to be obtained as information regarding living body tissue existing at a desired observation site while removing, using a light-shielding apparatus, reflected light reflected off a surface of the living body tissue among reflected light of illuminating light having a predetermined band based on a hemoglobin-absorption spectrum and which is irradiated to the living body tissue, by receiving reflected light reflected after reaching blood vessels directly underneath the living body tissue with a CCD (charge coupled device).

Meanwhile, recently, in the field of medicine or the like, endoscope apparatuses using an endoscope have come to be widely used in examinations, observations, and treatment using a treatment instrument.

In addition, there are cases where an endoscope apparatus is used to observe a flow of blood vessels as an internal observation object tissue inside living body tissue within a body cavity. For example, a conventional example described in Japanese Patent No. 2528104 discloses an endoscope apparatus that brings a distal end face of a light guide into close contact with living body tissue in order to suppress reflected light from the living body surface.

Furthermore, Japanese Patent Application Laid-Open Publication No. 2005-192945 discloses a medical apparatus protruding in a cylindrical shape from a distal end portion of an insertion portion of an endoscope and which performs suction through ultrasonic vibration.

SUMMARY OF THE INVENTION

A scattering medium internal observation apparatus according to the present invention includes: a light source; an illuminating apparatus that guides light from the light source to an observation object that is a scattering body; and an observation optical system for observing the observation object illuminated by the illuminating apparatus, wherein the illuminating apparatus has a light-guiding member that guides light from the light source to a surface of the observation object, and a light-shielding member that covers the surface of the observation object and which shields light reflected or scattered in the vicinity of the light-guiding member of the observation object is disposed in the vicinity of an end portion of the light-guiding member on an observation object-side.

A scattering medium internal observation apparatus according to the present invention includes: a light source; an illuminating apparatus that guides light from the light source to an observation object that is a scattering body; and an image pickup apparatus that picks up an image of the observation object illuminated by the illuminating apparatus, wherein the illuminating apparatus has a light-guiding member that guides light from the light source to a surface of the observation object, a light-shielding member that covers the surface of the observation object and which shields light reflected or scattered in the vicinity of the light-guiding member of the observation object is disposed in the vicinity of an end portion of the light-guiding member on an observation object-side, and the image pickup apparatus creates an image of a structure existing inside the observation object using light scattered inside the observation object and which is returned from a portion other than a region covered by the light-shielding member among light guided to the surface of the observation object by the light-guiding member.

A scattering medium internal observation apparatus according to the present invention includes: a light source; an illuminating apparatus that guides light from the light source to an observation object that is a scattering body; and an observation optical system for observing the observation object illuminated by the illuminating apparatus, wherein the illuminating apparatus has a light-guiding member that guides light from the light source to the inside of the observation object, and a light-shielding member that covers the surface of the observation object and which shields light reflected or scattered in the vicinity of the light-guiding member of the observation object is disposed in the vicinity of an end portion of the light-guiding member on an observation object-side.

A scattering medium internal observation apparatus according to the present invention includes: a light source; an illuminating apparatus that guides light from the light source to an observation object that is a scattering body; and an image pickup apparatus that picks up an image of the observation object illuminated by the illuminating apparatus, wherein the illuminating apparatus has a light-guiding member that guides light from the light source to the inside of the observation object, a light-shielding member that covers the surface of the observation object and which shields light reflected or scattered in the vicinity of the light-guiding member of the observation object is disposed in the vicinity of an end portion of the light-guiding member on an observation object-side, and the image pickup apparatus creates an image of a structure existing inside the observation object using light scattered inside the observation object and which is returned from a portion other than a region covered by the light-shielding member among light guided to the inside of the observation object by the light-guiding member.

An image pickup system according to the present invention includes: an illuminating apparatus that illuminates a sample with a pulsed illuminating light including at least an infrared wavelength component; an image pickup apparatus that picks up an image of light from the sample illuminated by the illuminating apparatus; and a timing control apparatus that controls an image pickup timing of the image pickup apparatus, wherein the timing control apparatus is configured so as to match an irradiating interval of the illuminating apparatus with an image pickup interval of the image pickup apparatus, and to send, to the image pickup apparatus, an image pickup timing signal that causes an image to be picked up after a predetermined time lag from an irradiating timing of the illuminating apparatus so that an image of at least a portion of unnecessary scattered light occurring at the sample illuminated by the illuminating apparatus is not picked up.

An image pickup system according to the present invention includes: an illuminating apparatus that illuminates a sample with a pulsed illuminating light including at least an infrared wavelength component; an image pickup apparatus that picks up an image of light from the sample illuminated by the illuminating apparatus; a shutter apparatus disposed either inside the image pickup apparatus or between the image pickup apparatus and the sample; and a timing control apparatus that controls a shutter timing of the shutter apparatus, wherein the timing control apparatus is configured so as to match an irradiating interval of the illuminating apparatus with a shutter interval of the shutter apparatus, and to send, to the shutter apparatus, a shutter timing signal that causes the shutter apparatus to operate after a predetermined time lag from an irradiating timing of the illuminating apparatus so that an image of at least a portion of unnecessary scattered light occurring at the sample illuminated by the illuminating apparatus is not picked up.

An image pickup method according to the present invention is an image pickup method using an illuminating apparatus that illuminates a sample with an illuminating light including at least an infrared wavelength component and an image pickup apparatus that picks up an image of light from the sample illuminated by the illuminating apparatus, wherein the image pickup method: causes the illuminating apparatus to repetitively irradiate the illuminating light in a pulsed form; matches an irradiating interval of the illuminating apparatus with an image pickup interval of the image pickup apparatus; and causes an image pickup timing of the image pickup apparatus to be delayed by a predetermined time period from an irradiating timing of the illuminating apparatus so that an image of at least a portion of unnecessary scattered light occurring at the sample illuminated by the illuminating apparatus is not picked up.

An image pickup method according to the present invention is an image pickup method using an illuminating apparatus that illuminates a sample with an illuminating light including at least an infrared wavelength component, an image pickup apparatus that picks up an image of light from the sample illuminated by the illuminating apparatus, and a shutter apparatus disposed either inside the image pickup apparatus or between the image pickup apparatus and the sample, wherein the image pickup method: causes the illuminating apparatus to repetitively irradiate the illuminating light in a pulsed form; matches an irradiating interval of the illuminating apparatus with a shutter interval of the shutter apparatus; and causes a shutter timing of the shutter apparatus to be delayed by a predetermined time period from an irradiating timing of the illuminating apparatus so that an image of at least a portion of unnecessary scattered light occurring at the sample illuminated by the illuminating apparatus is not picked up.

An image pickup system according to the present invention includes: illuminating section for irradiating an illuminating light having a predetermined wavelength band which at least exceeds a wavelength of 1200 nm to a living body tissue; reflected light suppressing section for shielding among illuminating light irradiated to the living body tissue reflected light reflected off of a first living body tissue existing in the vicinity of a surface of the living body tissue and for passing among the illuminating light reflected light reflected off of a second living body tissue that exists inside the living body tissue in a state where at least a portion of the second living body tissue is covered by the first living body tissue; image pickup section that is sensitive in at least an infrared region whose wavelength exceeds 1200 nm and which picks up an image of the living body tissue based on reflected light reflected off of the second living body tissue; and positioning section for maintaining a constant predetermined distance between the reflected light suppressing section and the image pickup section by fixing a position at which the reflected light suppressing section is disposed.

An image pickup system according to the present invention includes: illuminating section capable of irradiating to a living body tissue a plurality of illuminating lights respectively having wavelength bands that differ from each other in at least a wavelength band equal to or greater than 1000 nm; image pickup section that is sensitive in at least a wavelength band equal to or greater than 1000 nm and which picks up living body tissue images respectively illuminated by the plurality of illuminating lights; luminance value comparing section for detecting luminance values of a plurality of images corresponding to the plurality of living body tissue images picked up by the image pickup section and for comparing, based on the detection results, differences in luminance values between a predetermined living body tissue image and an image other than the predetermined living body tissue for each of the plurality of images; image extracting section for extracting a single image with maximum difference in luminance values among the plurality of images; and illumination selecting section for selecting, based on information regarding the single image, a single illuminating light having a single wavelength band that enables an image having a difference in luminance values similar to the single image to be obtained among the plurality of illuminating lights respectively having wavelength bands that differ from each other.

An endoscope apparatus according to the present invention includes: an endoscope having an insertion portion provided with a distal end portion capable of bringing at least a distal end face which an observation window faces into close contact with a surface of a living body tissue to be an observation object; a suction apparatus having a sheath for suction to be mounted on the endoscope and which interiorly includes the distal end portion and in which a distal end opening is formed on an outer peripheral side of the distal end portion, and suction section provided on a proximal end-side of the sheath for suction so as to communicate with the distal end opening and which performs suction; and distance reducing section for sucking in the living body tissue around the distal end face and in a portion opposing the distal end opening through a suction operation of the suction apparatus to reduce a distance from a surface of the living body tissue to blood vessels running inside the surface as an internal observation object tissue within an observation field of view of the observation window.

DESCRIPTION OF THE PREFERRED EMBODIMENT(S)

(First Embodiment)

Figure 1:
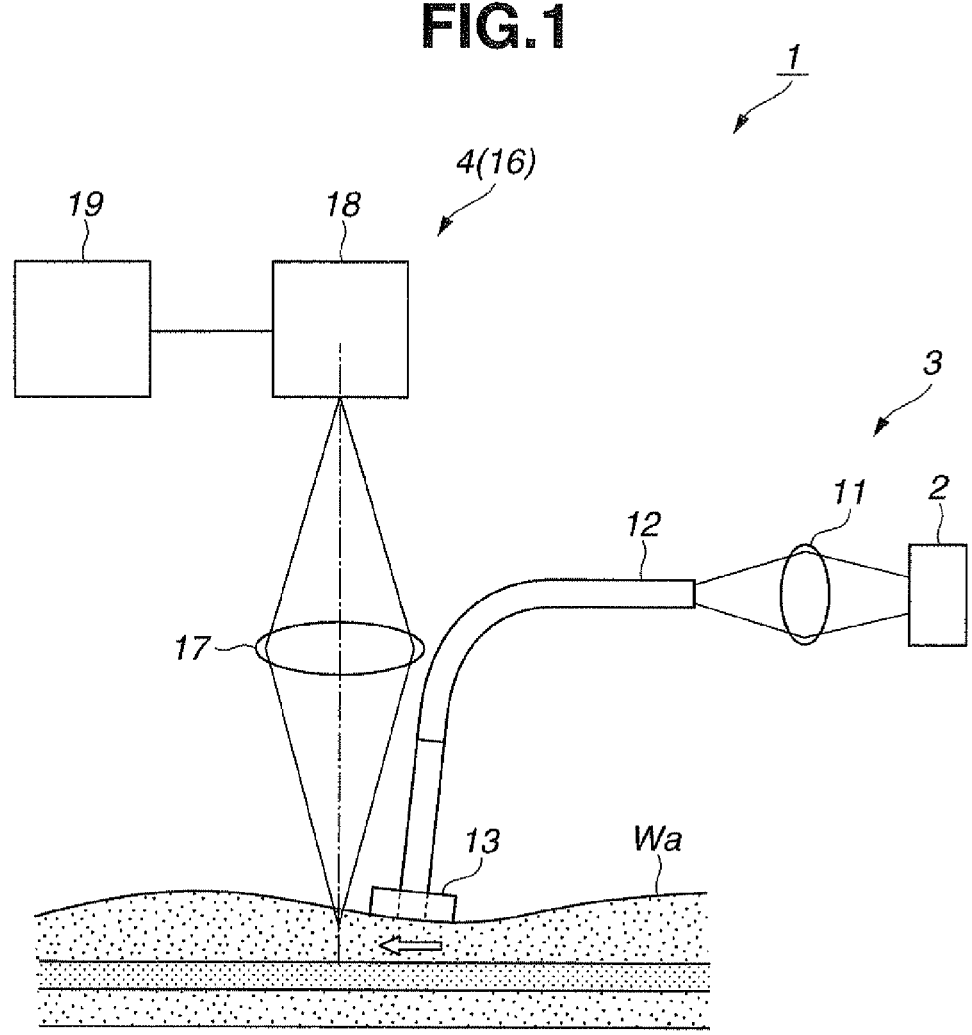
FIG. 1 is a diagram showing a schematic configuration of a scattering medium internal observation apparatus according to a first embodiment of the present invention.

Disclosed in embodiments of the present invention are various techniques related to the contents described below.

The present invention provides a scattering medium internal observation apparatus including: a light source; an illuminating apparatus that guides light from the light source to an observation object that is a scattering body; and an observation optical system for observing the observation object illuminated by the illuminating apparatus, wherein the illuminating apparatus has a light-guiding member that guides light from the light source to a surface of the observation object, and a light-shielding member that covers the surface of the observation object and which shields light reflected or scattered in the vicinity of the light-guiding member of the observation object is disposed in the vicinity of an end portion of the light-guiding member on an observation object-side.

In addition, the present invention provides a scattering medium internal observation apparatus including: a light source; an illuminating apparatus that guides light from the light source to an observation object that is a scattering body; and an image pickup apparatus that picks up an image of the observation object illuminated by the illuminating apparatus, wherein the illuminating apparatus has a light-guiding member that guides light from the light source to a surface of the observation object, a light-shielding member that covers the surface of the observation object and which shields light reflected or scattered in the vicinity of the light-guiding member of the observation object is disposed in the vicinity of an end portion of the light-guiding member on an observation object-side, and the image pickup apparatus creates an image of a structure existing inside the observation object using light scattered inside the observation object and which is returned from a portion other than a region covered by the light-shielding member among light guided to the surface of the observation object by the light-guiding member.

The present invention described above has been made based on the following novel findings.

When an illuminating light is irradiated on a surface of a scattering body having uniform scattering characteristics, a portion of the illuminating light is scattered by the scattering body and light diffuses in a direction that differs from an irradiation direction of the illuminating light. Consequently, an illuminating range of the illuminating light gradually widens as the illuminating light advances through the scattering body. In addition, illuminating light intensity gradually attenuates as the illuminating light advances through the scattering body.

A portion of the scattered light diffuses in a direction opposite to the irradiating direction of the illuminating light. Therefore, by using scattered light which reaches a position that is even deeper than an observation object existing inside a scattering body and which returns in a direction opposite to the irradiation direction of the illuminating light, it is possible to acquire an image of the observation object inside the scattering body.

More specifically, since the observation object is to be secondarily illuminated by the scattered light, by detecting such scattered light at a surface of the scattering body, information on the observation object can be acquired based on information such as intensity of the scattered light.

As described, a scattering body at a position deeper than the observation object can be regarded as a virtual illuminating light source. The size of the virtual illuminating light source (virtual light source) approaches a size similar to an illuminating range of the illuminating apparatus at a surface of the scattering body the closer the virtual light source is to a superficial layer of the scattering body, and brightness as a light source becomes greater. In addition, the deeper inside the scattering body, the size of the virtual light source increases and brightness as a light source decreases.

As an example, a description will now be given on a case where a body to be an observation object exists inside a scattering medium and the observation object is to be observed by irradiating the same with an illuminating light, such as the case of observing blood vessels in fat.

When the observation object is in a vicinity of a surface of the scattering body, most of a virtual light source exists at a portion deeper than the observation object. Thus, the virtual light source serves to secondarily illuminate the observation object, thereby enabling the observation object to be observed based on light (scattered light) emitted by the virtual light source.

However, when the observation object is at a portion deep underneath the surface of the scattering body, light scattered at a position shallower than the observation object is unable to secondarily illuminate the observation object. In addition, the intensity of light scattered at a position shallower than the observation object becomes greater than the intensity of light scattered at a position deeper than the observation object.

Consequently, when acquiring an image of the observation object using light scattered at a position deeper than the observation object, there is a problem in that light scattered at a position shallower than the observation object becomes noise light and causes deterioration of an acquired image.

Since the noise light occurs strongly in the vicinity of a superficial layer of a scattering body when irradiating the scattering body with an illuminating light, observing the observation object becomes more difficult the deeper the position of the observation object inside the scattering body and the higher the scattering coefficient of the scattering body.

Accordingly, in order to remove the noise light described above, the present invention is arranged so that light scattered at a position shallower than the observation object does not reach an observation optical system or an image pickup apparatus for acquiring an image of the observation object.

As described above, the size of a distribution range of light scattered in the vicinity of a superficial layer of a scattering body is similar to the size of an illuminating range of an illuminating light. Accordingly, in the present invention, a configuration is adopted in which a light-shielding member is disposed around the illuminating range of the illuminating range (i.e., around a light-guiding apparatus) so as to shield a range wider than the illuminating range with the light-shielding member. As a result, light scattered in the vicinity of the superficial layer of the scattering body can be shielded and noise light reaching an observation optical system can be removed.

Incidentally, portions of the scattering body which oppose a light-guiding member or a light-shielding member are covered by the light-guiding member or the light-shielding member and therefore cannot be directly observed.

However, by detecting scattered light returned from a detectable range around the light-shielding member, based on information on the scattered light, an image of a portion of the observation object which opposes the light-guiding member and a portion covered by the light-shielding member can be acquired.

Therefore, with the scattering medium internal observation apparatus according to the present invention, an image of an observation object in a scattering body can be acquired using light scattered inside the scattering body.

In this case, by appropriately setting a light-shielded region of a light-shielding member according to a scattering coefficient of a scattering body and a depth at which an observation object exists in the scattering body, noise light reaching an observation optical system can be removed more effectively.

In the scattering medium internal observation apparatus according to the present invention, a light-shielding member may be configured so as to be able to come into contact with an observation object.

In this case, by bringing the light-shielding member into contact with the observation object that is a scattering body, light scattered in the vicinity of a superficial layer in a region of the observation object which is covered by the light-shielding member can be shielded more effectively. As a result, noise light removal can be effectively performed and a favorable image can be obtained.

In addition, the scattering medium internal observation apparatus according to the present invention may include a scanning apparatus that causes a light-guiding member to scan over an observation object.

In this case, by having the light-guiding member scan over the observation object, internal observation can be performed over a wide range of the observation object.

Particularly, by having the illuminating apparatus scan and by providing an image processing apparatus that synthesizes a plurality of images acquired by an observation optical system or an image pickup apparatus, internal images can be acquired over a wide range inside the scattering body.

Furthermore, the present invention provides a scattering medium internal observation apparatus including: a light source; an illuminating apparatus that guides light from the light source to an observation object that is a scattering body; and an observation optical system for observing the observation object illuminated by the illuminating apparatus, wherein the illuminating apparatus has a light-guiding member that guides light from the light source to the inside of the observation object, and a light-shielding member that covers the surface of the observation object and which shields light reflected or scattered in the vicinity of the light-guiding member of the observation object is disposed in the vicinity of an end portion of the light-guiding member on an observation object-side.

Moreover, the present invention provides a scattering medium internal observation apparatus including: a light source; an illuminating optical system that guides light from the light source to an observation object that is a scattering body; and an image pickup apparatus that picks up an image of the observation object illuminated by the illuminating optical system, wherein the illuminating apparatus has a light-guiding member that guides light from the light source to the inside of the observation object, a light-shielding member that covers the surface of the observation object and which shields light reflected or scattered in the vicinity of the light-guiding member of the observation object is disposed in the vicinity of an end portion of the light-guiding member on an observation object-side, and the image pickup apparatus creates an image of a structure existing inside the observation object using light scattered inside the observation object and which is returned from a portion other than a region covered by the light-shielding member among light guided to the inside of the observation object by the light-guiding member.

As described above, by guiding illuminating light into the inside of a scattering body by the illuminating apparatus, a greater amount of illuminating light reaches positions deeper than the observation object.

As a result, the intensity of a virtual light source existing at a position deeper than the observation object can be increased and the contrast of an image of the observation object acquired by an observation optical system or an image pickup apparatus can be improved.

Incidentally, even in such a configuration, by disposing a light-shielding member around a light-guiding member, noise light scattered at a position shallower than the observation object can be removed.

Here, the aforementioned observation object-side end portion of the light-guiding member may be housed inside a hollow needle-like member of which at least a distal end is to be inserted into the observation object.

In this case, by inserting the hollow needle-like member into the observation object, the observation object-side end portion of the light-guiding member may be readily introduced into the observation object.

In addition, the same effect may be achieved by forming the observation object-side end portion of the light-guiding member in a needle-like shape.

In this case, the light-shielding member preferably doubles as a stopper formed at, for example, an outer peripheral portion of the hollow needle-like member or a light-guiding member and which regulates an ingression amount of the needle-like member into the observation object so as to prevent excessive ingress of the needle-like member upon insertion.

Furthermore, by providing a light-shielding member that configures a stopper so that a position thereof is adjustable with respect to the light-guiding member, a depth to which the light-guiding member is inserted into the scattering body can be adjusted according to the depth of the observation object. Through such a configurations for example, it is possible to prevent damages to blood vessels in fat.

Moreover, by using a plurality of light-guiding members, it is possible to widen a range in which an image of an observation object can be acquired by an observation optical system or an image pickup apparatus or to increase light that secondarily illuminates the observation object (increase the intensity of a virtual light source existing at a position deeper than the observation object) and enhance a contrast of an image of the observation object acquired by the observation optical system.

A first embodiment of the present invention will now be described with reference to FIGS. 1 to 6.

As shown in FIG. 1, a scattering medium internal observation apparatus 1 according to a first embodiment of the present invention includes: a light source 2; an illuminating apparatus 3 that guides light from the light source 2 to an observation object Wa that is a scattering body; and an observation optical system 4 for observing the observation object Wa illuminated by the illuminating apparatus 3.

The illuminating apparatus 3 includes: a collecting lens 11 that focuses light from the light source 2; and a light-guiding member 12 that guides light collected by the collecting lens 11 onto a surface of the observation object Wa. As the light-guiding member 12, for example, a thin linear light guide such as an optical fiber is used. In addition, a light-shielding member 13 that covers the surface of the observation object Wa and shields light reflected or scattered in a vicinity of the light-guiding member 12 of the observation object Wa is disposed in a vicinity of an observation object-side end portion of the light-guiding member 12.

In the first embodiment, the light-guiding member 12 is configured by a bundle of optical fibers 12a. In addition, optical fibers 12a are disposed in rows in a direction perpendicular to axis lines of the optical fibers 12a in the vicinity of an observation object-side end portion of the light-guiding member 12. As a result, an illuminating range of the light-guiding member 12 is formed in a band-like shape along an alignment direction of the optical fibers 12a.

Figure 2:
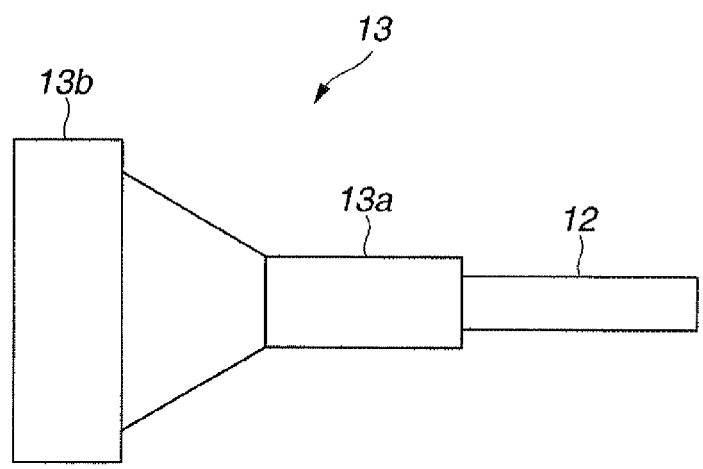
FIG. 2 is a side view showing a configuration of a light-shielding member of a scattering medium internal observation apparatus according to the first embodiment of the present invention.

As shown in FIG. 2, a light-shielding member 13 includes a sleeve 13a into which an end portion of the light-guiding member 12 is inserted and a widening portion 13b provided at a distal end of the sleeve 13a. In the first embodiment, the light-shielding member 13 is fixed to the light-guiding member 12 and the widening portion 13b is configured so as to receive the observation object Wa by a distal end thereof.

Figure 3:
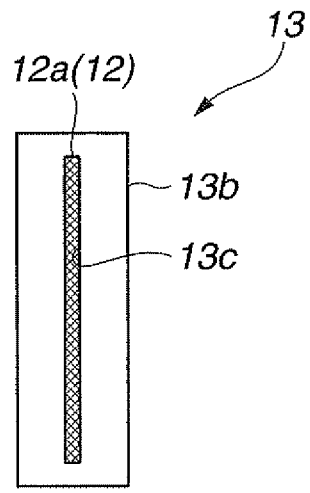
FIG. 3 is a distal end view showing a configuration of a light-guiding member and a light-shielding member of a scattering medium internal observation apparatus according to the first embodiment of the present invention.

As shown in FIG. 3, a slit 13c is formed along a longitudinal direction (the width direction of the widening portion 13b) on a distal end face of the widening portion 13b.

The optical fiber 12a is inserted into the slit 13c. As a result, at a distal end of the light-guiding member 12, the entire circumference of the light-guiding member 12 is covered by the widening portion 13b, and optical fibers 12a configuring the light-guiding member 12 are integrally retained with respect to the widening portion 13b in a state where the optical fibers 12a are disposed in rows in a direction perpendicular to axis lines of the optical fibers 12a.

As the observation optical system 4, an optical system for visually observing the observation object Wa may be used. Alternatively, an optical system may be used which includes an image pickup apparatus that acquires an appearance of the observation object Wa as image information.

In the first embodiment, as shown in FIG. 1, as the observation optical system 4, an image pickup apparatus 16 is used which creates an image of a structure existing inside the observation object Wa using light scattered inside the observation object Wa and returned from a portion other than a region covered by the light-shielding member 13 among light guided to a surface of the observation object Wa by the light-guiding member 12. The image pickup apparatus 16 includes: an objective lens 17; an image pickup device 18 that picks up an image formed by the objective lens 17; and an image processing apparatus 19 that creates an image of a structure existing inside the observation object Wa based on an output of the image pickup device 18. As the image pickup device 18, for example, a CCD (charge coupled device) apparatus is used.

An observation method of the observation object Wa using the scattering medium internal observation apparatus 1 configured as shown will now be described.

First, a principle of observation of the observation object Wa by the scattering medium internal observation apparatus 1 will be described with reference to FIGS. 4 to 6.

Figure 4:
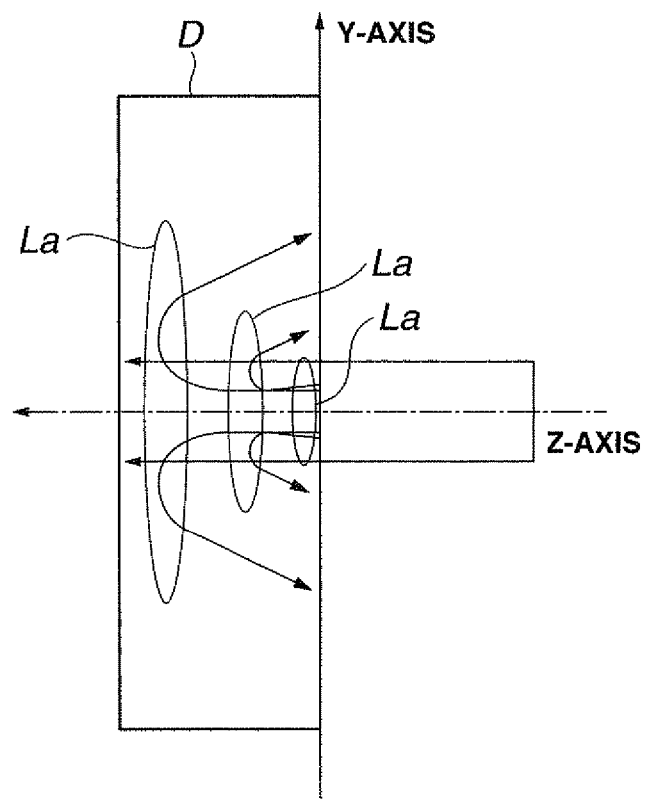
FIG. 4 is a diagram schematically showing a behavior of light when irradiating illuminating light for observation to a surface of a scattering body having uniform scattering characteristics.
Figure 5:
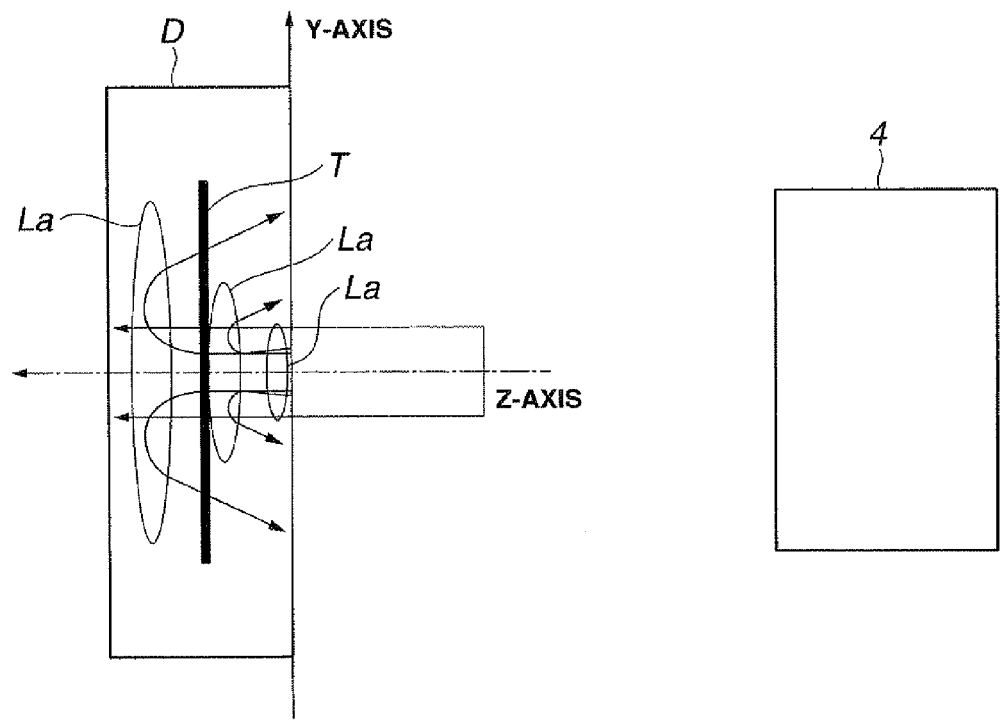
FIG. 5 is a diagram schematically showing scattering of light inside a scattering body.
Figure 6:
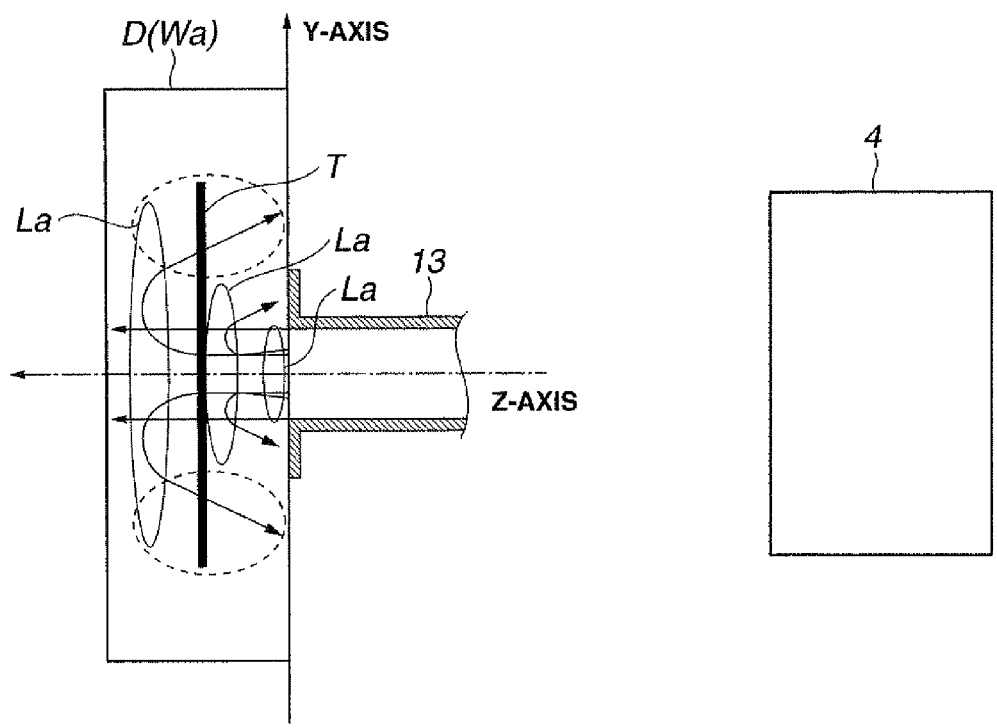
FIG. 6 is a diagram schematically showing a principle of observation by a scattering medium internal observation apparatus according to the first embodiment of the present invention.

FIGS. 4 to 6 are diagrams schematically showing a behavior of light when irradiating illuminating light for observation to a surface of a scattering body D. In FIGS. 4 to 6, the direction of progress of the illuminating light and the thickness direction of the scattering body D are represented as a Z-axis and a direction along the surface of the scattering body D is represented as a Y-axis, whereby an appearance of light inside the scattering body D is simplistically expressed by a Y-Z plane.

As shown in FIG. 4, when an illuminating light is irradiated on the surface of the scattering body D having uniform scattering characteristics, a portion of the illuminating light is scattered by the scattering body D and light diffuses in a direction that differs from the irradiation direction of the illuminating light. Consequently, an illuminating range of the illuminating light gradually widens as the illuminating light advances through the scattering body D. In addition, illuminating light intensity gradually attenuates due to scattering as the illuminating light advances through the scattering body D.

The scattering medium internal observation apparatus 1 shown in the first embodiment acquires an image of an observation object T (refer to FIG. 5) in the scattering body D using light scattered inside the scattering body D. More specifically, the scattering medium internal observation apparatus 1 is arranged to use light that reaches a position deeper than the observation object T existing inside the scattering body D and which returns in a direction opposite to the irradiating direction of the illuminating light.

Since the observation object T is to be secondarily illuminated by the scattered light, information on the observation object T can be acquired by detecting the scattered light at the surface of the scattering body D.

As described, a portion of the scattering body D which is at a position deeper than the observation object T can be regarded as a virtual illuminating light source La.

As schematically shown in FIG. 4, the size of the virtual light source La approaches a size similar to an illuminating range of the illuminating apparatus 3 at the surface of the scattering body D the closer the virtual light source La is to a superficial layer of the scattering body D, and brightness as a light source also becomes greater. In addition, the deeper inside the scattering body D, the size of the virtual light source La increases and brightness as a light source decreases.

Next, a description will be given on a case where a body to be an observation object exists inside a scattering medium and the observation object T is to be observed by irradiating the same with an illuminating light, such as a case of observing blood vessels in fat.

When the observation object T is in the vicinity of the surface of the scattering body D, most of the virtual light source La exists at a portion deeper than the observation object T. Thus, the virtual light source La serves to secondarily illuminate the observation object T, thereby enabling the observation object T to be observed. However, as shown in FIG. 5, when the observation object T is at a portion deep underneath the surface of the scattering body D, light scattered at a position shallower than the observation object T is unable to secondarily illuminate the observation object T. In addition, the intensity of light scattered at a position shallower than the observation object T becomes greater than the intensity of light scattered at a position deeper than the observation object T.

Consequently, when acquiring an image of the observation object T using light scattered at a position deeper than the observation object T, light scattered at a position shallower than the observation object T becomes noise light that causes deterioration of an acquired image.

Since the noise light occurs strongly in the vicinity of a superficial layer of the scattering body D when irradiating the same with an illuminating light observing the observation object T becomes more difficult the deeper the position of the observation object T inside the scattering body D and the higher the scattering coefficient of the scattering body D.

Accordingly, with the scattering medium internal observation apparatus 1 shown in the first embodiment, in order to remove the noise light described above, light scattered at a position shallower than the observation object T in the scattering body D is arranged so as not to reach the observation optical system 4 for acquiring an image of the observation object T.

As shown in FIG. 6, the size of a distribution range of light scattered in the vicinity of a superficial layer of the scattering body D is similar to the size of the illuminating range of the illuminating light. Accordingly, with the scattering medium internal observation apparatus 1, a configuration is adopted in which a light-shielding member 13 is disposed around the illuminating range of the illuminating light so as to shield a range wider than the illuminating range using the light-shielding member 13. As a result, light scattered in the vicinity of the superficial layer of the scattering body D can be shielded and noise light reaching the observation optical system 4 can be removed.

A specific observation method according to the scattered medium internal observation apparatus 1 will now be described. In the first embodiment, as shown in FIGS. 1 and 6, illumination by the illuminating apparatus 3 is performed in a state where the distal end face of the light-shielding member 13 is in close contact with a surface of fat so that light does not escape peripherally from a surface of a portion of fat that is an observation object Wa and which opposes the light-shielding member 13 of the illuminating apparatus 3. In addition, the observation optical system 4 is disposed at a predetermined distance from the fat surface so that a predetermined observation object region around the light-shielding member 13 on the fat surface is included in the field of view.

Light irradiated from the illuminating apparatus 3 reaches the inside of fat and is scattered. Light scattered at a position that is shallower than blood vessels distributed inside the fat is shielded by the light-shielding member 13 even when reaching the fat surface. Light scattered at a position deeper than the blood vessels exit the fat surface without being shielded by the light-shielding member 13 and is captured by the observation optical system 4. An image of the observation object T is created by an image processing apparatus 19 based on the scattered light.

More specifically, the image processing apparatus 19 creates an image of a distribution state of blood vessels existing in fat based on a distribution of contrasts using the fact that a contrast is created between blood vessels and the surrounding fat in an image picked up by the image pickup device 18 due to differences in scattering coefficients and absorption coefficients of fat and blood vessels.

Note that portions of the scattering body D which oppose the light-guiding member 12 or the light-shielding member 13 are covered by the light-guiding member 12 or the light-shielding member 13 and therefore cannot be directly observed.

However, by detecting scattered light returned from a detectable region (the region shown enclosed in the dashed line in FIG. 6) around the light-shielding member 13, based on information on the scattered light, an image of a portion of the observation object T which opposes the light-guiding member 12 and a portion covered by the light-shielding member 13 can be acquired.

Therefore, with the scattering medium internal observation apparatus 1 according to the first embodiment, using light scattered inside the scattering body D, an image of the observation object T in the scattering body D can be acquired including a portion opposing the light-guiding member 12 and a portion covered by the light-shielding member 13.

As described above, according to the scattering medium internal observation apparatus 1 shown in the first embodiment, an image of the observation object T in the scattering body D can be easily and accurately acquired using light scattered inside the scattering body D.

In this case, in the first embodiment, while an example was shown in which observation is performed in a state where the light-guiding member 12 and the light-shielding member 13 are fixed with respect to the observation object Wa, the present invention is not limited thereto. Instead, the scattering medium internal observation apparatus 1 may be provided with a scanning apparatus (not shown) which causes an object-side end portion of the light-guiding member 12 and the light-shielding member 13 to scan in a direction (for example, the direction indicated by an arrow in FIG. 1) approximately perpendicular to an arrangement direction of optical fibers 12*a* configuring the light-guiding member 12.

The scanning apparatus can be configured by, for example, a moving apparatus that integrally moves the light-guiding member 12 and the light-shielding member 13 in a predetermined scan direction and the aforementioned image processing apparatus 19. In this case, the image processing apparatus 19 is configured so as to cause the observation optical system 4 to acquire, in chronological order, a plurality of images in synchronization with a movement of the light-guiding member 12 and the light-shielding member 13 by the moving apparatus, whereby the respective images are synthesized to obtain an image including the entire scan range.

As a result, a distribution state of blood vessels can be accurately grasped over a wide range.

Moreover, in order to have light reach deep portions of a scattering body such as fat, the wavelength of the illuminating light is desirably such that is less susceptible to scattering, or more specifically, an infrared light with a wavelength equal to or greater than 1000 nm.

Furthermore, with the scattering medium internal observation apparatus 1, by appropriately setting the size of a light-shielded region of the light-shielding member 13 according to a scattering coefficient of the scattering body D and the depth at which the observation object T exists in the scattering body D, noise light reaching the observation optical system 4 can be removed more effectively.

(Second Embodiment)

Figure 7:
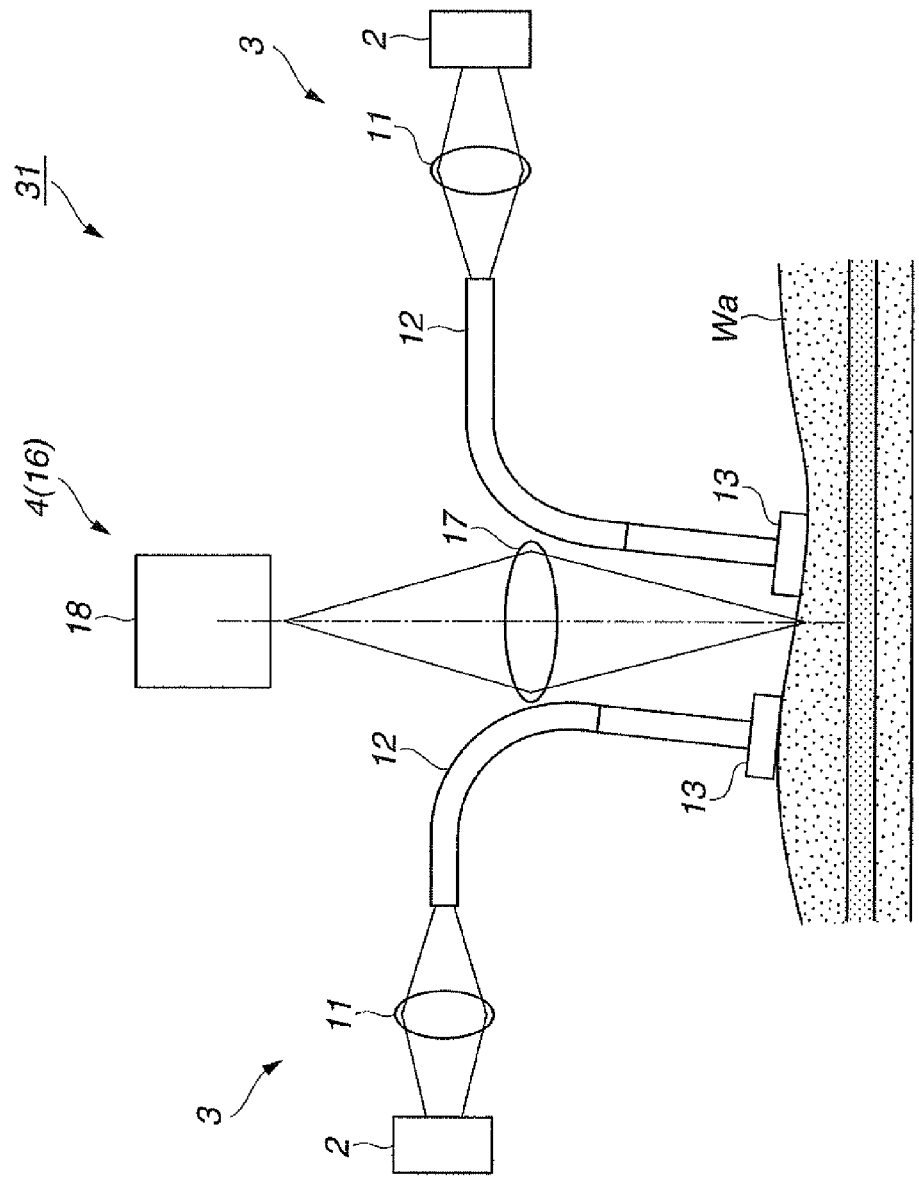
FIG. 7 is a diagram showing a schematic configuration of a scattering medium internal observation apparatus according to a second embodiment of the present invention.

A second embodiment of the present invention will now be described with reference to FIGS. 7 and 8. As shown in FIG. 7, a scattering medium internal observation apparatus 31 shown in the second embodiment is the scattering medium internal observation apparatus 1 shown in the first embodiment provided with a plurality of illuminating apparatuses 3.

The second embodiment is configured such that distal end portions of light-guiding members 12 of two illuminating apparatuses 3 are connected using a stay or the like so that respective rows of optical fibers 12*a* are approximately parallel to each other and that regions of virtual light sources respectively formed by the illuminating apparatuses 3 overlap each other.

According to the scattering medium internal observation apparatus 31, providing the plurality of illuminating apparatuses 3 enables a region in which the inside of fat is illuminated to be widened. As a result, images of blood vessels inside the fat can be created at high contrast across a wide range.

In addition, according to the scattering medium internal observation apparatus 31, since providing a plurality of illuminating apparatuses 3 increases the light amount of the virtual light sources, blood vessels distributed in the fat to be rendered at high contrast.

In this case, even with the scattering medium internal observation apparatus 31, a scanning apparatus can be provided which causes a plurality of illuminating apparatuses on a surface of fat that is an observation object to be synchronized and scanned.

Figure 8:
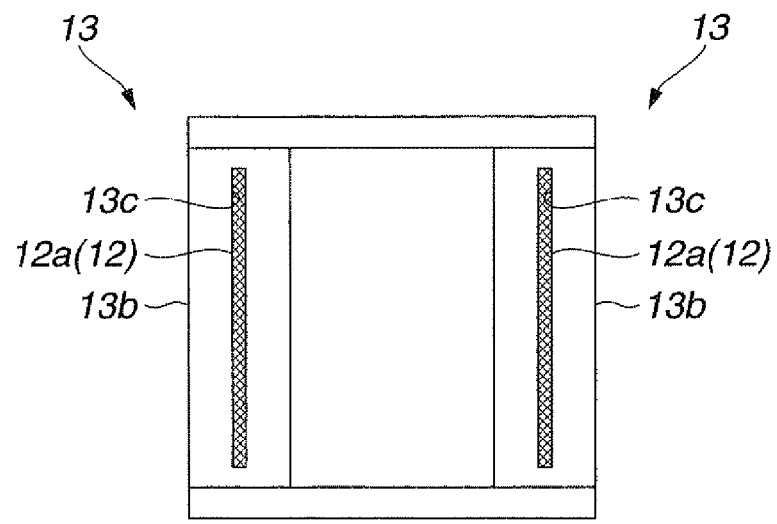
FIG. 8 is a diagram showing an arrangement of an illuminating apparatus of a scattering medium internal observation apparatus according to the second embodiment of the present invention.
Figure 9:
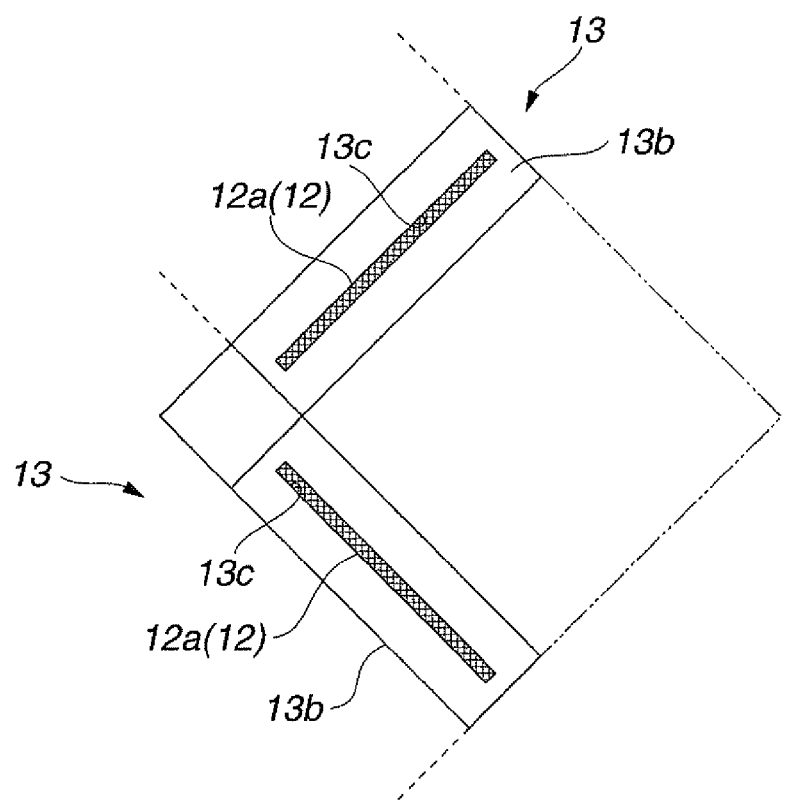
FIG. 9 is a diagram showing another example of an arrangement of an illuminating apparatus of a scattering medium internal observation apparatus according to the second embodiment of the present invention.

Furthermore, the scattering medium internal observation apparatus 31 can also be configured so that rendering can be performed with perspective even in a state where blood vessels are sterically distributed by: adjacently disposing distal ends of light-guiding members 12 of the respective illuminating apparatuses 3 in a direction intersecting an arrangement direction of optical fibers 12*a* as shown in FIG. 8 (an approximately perpendicular direction in FIG. 8); creating a range (the region indicated by the dashed-to dotted line) in which regions of virtual light sources formed by the respective illuminating apparatuses 3 overlap each other and a range (the region indicated by the dashed line) in which regions of virtual light sources do not overlap each other; and creating an intensity distribution at the virtual light sources.

(Third Embodiment)

A third embodiment of the present invention will now be described with reference to FIGS. 10 and 11.

Figure 10:
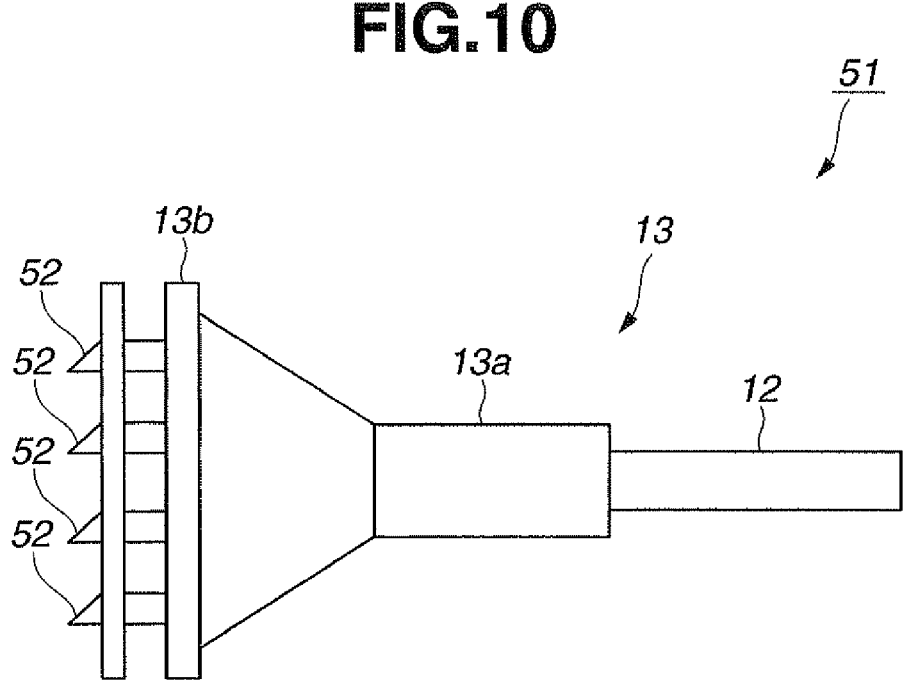
FIG. 10 is a diagram showing a configuration of an illuminating apparatus of a scattering medium internal observation apparatus according to a third embodiment of the present invention.

As shown in FIG. 10, a scattering medium internal observation apparatus 51 shown in the third embodiment is the scattering medium internal observation apparatus 1 shown in the first embodiment or the scattering medium internal observation apparatus 31 shown in the second embodiment in which the configuration of the illuminating apparatus 3 has been changed.

Figure 11:
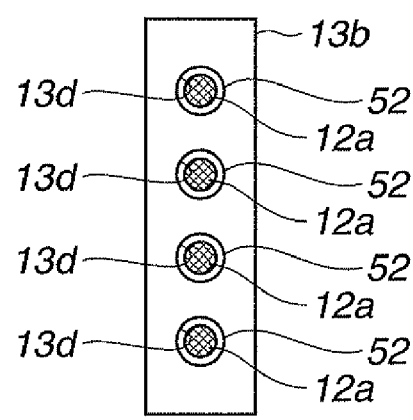
FIG. 11 is a distal end view showing a configuration of an illuminating apparatus of a scattering medium internal observation apparatus according to the third embodiment of the present invention.

As shown in FIG. 11, with the scattering medium internal observation apparatus 51, an observation object-side end portion of a light-guiding member 12 that configures the illuminating apparatus 3 is housed inside a hollow needle-like member 52 of which at least a distal end is inserted into an observation object Wa.

In the third embodiment, a widening portion 13*b* of a light-shielding member 13 is provided with a plurality of through-holes 13*d* arranged in a row along a width direction in place of the slits 13*c*.

Optical fibers 12a configuring the light-guiding member 12 is separated into the same number of bundles as the number of the through-holes 13d. A distal end of each bundle of the optical fibers 12a is inserted into the hollow needle-like member 52 and then inserted through a through-hole 13d together with the hollow needle-like member 52, whereby the distal end of the hollow needle-like member 52 protrudes from the distal end of the widening portion 13b.

As a result, by inserting the hollow needle-like member 52 into an observation object, it is possible to have the distal end of the light-guiding member 12 proceed into the observation object.

With the third embodiment, the light-guiding member 12 and the light-shielding member 13 are integrally fixed and the light-shielding member 13 configures a stopper that regulates an ingression amount of the hollow needle-like member 52 into the inside of the observation object.

Blood vessels having positions difficult to detect during a surgical operation or the like tend to exist in deep portions located 3 mm or more from the surface. Therefore, even when fat is penetrated, no blood vessels are damaged as long as the penetration depth is 1 to 2 mm from the fat surface. Accordingly, the amount of protrusion of the distal end of the hollow needle-like member 52 from the light-shielding member 13 is set to around 1 to 2 mm.

In this manner, by having the needle-like distal end portion of the illuminating apparatus enter the surface of fat that is the observation object to a predetermined depth (around 1 to 2 mm), it is possible to guide a large amount of light to positions deeper than the blood vessels. As a result, a vascular distribution image can be acquired with high contrast.

When positions of blood vessels inside fat tissue could not be detected using the scattering material internal observation apparatuses 1 and 31 shown in the first and second embodiments, it is anticipated that the blood vessels exist in deeper portions than a detectable range of the scattering material internal observation apparatuses 1 and 31 shown in the first and second embodiments. The illuminating apparatus according to the third embodiment is effective in such a case.

In addition, with the third embodiment, since illumination can be performed by moving the illuminating apparatus 3 closer to an observation object such as a blood vessel, a distribution image of an observation object T can be acquired at high contrast even when using a light whose wavelength is equal or is less than 1000 nm (in other words, a light with a wavelength susceptible to scattering) as the illuminating light.

Here, in the third embodiment, the light-shielding member 13 to function as a stopper is provided so that the position of the light-shielding member 13 is adjustable with respect to the light-guiding member 12. Accordingly, by adjusting the position (the position in an axis line direction of the light-guiding member 12) of the light-shielding member 13, an ingression amount of the light-guiding member 12 with respect to the observation object can be adjusted.

Moreover, with the third embodiment, while an example has been shown in which a hollow needle-like member 52 is provided at the light-shielding member 13, for example, the same effect can be achieved by forming the observation object-side distal end portion of the light-guiding member 12 in a needle-like shape.

Furthermore, while a configuration in which optical fibers 12a that are light guides are arranged in a row has been shown in each of the first to third embodiments described above, the present invention is not limited thereto, and no problems should occur even if the light guides are disposed in a different arrangement such as an arc-like shape.

(Fourth Embodiment)

Disclosed in embodiments of the present invention are various techniques related to the contents described below.

An image pickup system according to the present embodiment includes: an illuminating apparatus that illuminates a sample with a pulsed illuminating light including at least an infrared wavelength component; an image pickup apparatus that picks up an image of light from the sample illuminated by the illuminating apparatus; and a timing control apparatus that controls an image pickup timing of the image pickup apparatus, wherein the timing control apparatus is configured so as to match an irradiating interval of the illuminating apparatus with an image pickup interval of the image pickup apparatus, and to send, to the image pickup apparatus, an image pickup timing signal that causes an image to be picked up after a predetermined time lag from an irradiating timing of the illuminating apparatus such that an image of at least a portion of unnecessary scattered light occurring at the sample illuminated by the illuminating apparatus is not picked up.

Generally, among light incident into material that causes scattering of light (hereinafter referred to as "scattering material"), an average optical path length of light returning after passing near a surface of the scattering material is shorter than an average optical path length of light that has passed through a deep area in the scattering material. Therefore, light that has passed near the surface of the scattering material returns earlier than light that has passed through a deep area in the scattering material. In addition, light returning from near the surface of the scattering material has a higher light intensity while light returning from a deep area in the scattering material has a lower light intensity.

Consequently, when simply observing light returning from the scattering material, intense light returning from near the surface acts as noise light that makes it difficult to observe an observation object site in the scattering material.

In consideration thereof, with the image pickup system according to the present invention, an SN ratio of image pickup information is enhanced using the fact that intense noise light returning from near the surface of the scattering material returns earlier than light returning from the observation object site inside the scattering material.

More specifically, with the image pickup system according to the present invention, the illuminating apparatus irradiates a pulsed illuminating light to a sample.

The timing control apparatus controls an image pickup timing of the image pickup apparatus to delay the image pickup timing of the image pickup apparatus with respect to an irradiating timing of the illuminating apparatus so that an image of intense noise light which returns early among pulsed light returning from the sample is not picked up.

Consequently, the image pickup apparatus is able to pickup an image of light that returns later than the noise light or, in other words, light returning from a deep area of the sample at a favorable SN ratio.

The degree of scattering of illuminating light by the sample depends on the wavelength of the illuminating light and the shorter the wavelength of the illuminating light, the stronger the scattering. Therefore, in order to observe an observation object site at a deep area of the sample, it is important that illuminating light from the illuminating apparatus includes infrared light with a long wavelength which is less susceptible to scattering.

Here, as the illuminating apparatus, for example, an apparatus that generates pulsed light in synchronization with a pulsed trigger signal generated by an oscillator or the like (e.g., a pulsed laser generating apparatus) is used. In this case, the timing control apparatus can be configured so as to use an irradiating timing of the illuminating apparatus detected based on the trigger signal of the illuminating apparatus for controlling image pickup timings.

When actually performing image pickup, there may exist a time lag from the time a trigger signal pulse of the illuminating apparatus is generated to the time the illuminating apparatus actually irradiates pulsed light, or a time lag from the time the timing control apparatus issues an image pickup instruction to the image pickup apparatus to the time image pickup is actually performed by the image pickup apparatus.

Furthermore, an amount of time lag of the image pickup timing with respect to the irradiating timing must be set also taking into consideration a time period required for a light emitted by a light source of the illuminating apparatus to be transmitted through an optical system including the illuminating apparatus, and the lens, light guides (e.g., optical fibers or the like), and the like of the image pickup apparatus.

Although a suitable value of the amount of time lag can be estimated in advance to a certain extent, there are cases where a suitable value cannot be accurately known. In addition, while an absence of unnecessary scattered light is always better, due to the relationship with the brightness of an image, there may be cases where an observation can be performed easier when brighter even if a certain amount of unnecessary scattered light remains and contrast is somewhat inferior.

Therefore, favorable pickup images can be obtained by configuring the timing control apparatus such that, after setting an amount of time lag between the irradiating timing and the image pickup timing to an arbitrary initial value and having the image pickup apparatus perform preliminary image pickup, the amount of time lag is varied based on a result of the preliminary image pickup to optimize a state of scattered light removal from a pickup image of the image pickup apparatus.

In addition, the present invention provides an image pickup system including: an illuminating apparatus that illuminates a sample with a pulsed illuminating light including at least an infrared wavelength component; an image pickup apparatus that picks up an image of light from the sample illuminated by the illuminating apparatus; a shutter apparatus disposed either inside the image pickup apparatus or between the image pickup apparatus and the sample; and a timing control apparatus that controls a shutter timing of the shutter apparatus, wherein the timing control apparatus is configured so as to match an irradiating interval of the illuminating apparatus with a shutter interval of the shutter apparatus, and to send, to the shutter apparatus, a shutter timing signal that causes the shutter apparatus to operate after a predetermined time lag from the irradiating timing such that an image of at least a portion of unnecessary scattered light occurring at the sample illuminated by the illuminating apparatus is not picked up.

With the present image pickup system, an SN ratio of image pickup information is enhanced using the fact that intense noise light returning from near the surface of the scattering material returns earlier than light returning from the observation object site inside the scattering material.

More specifically, with the image pickup system, the illuminating apparatus irradiates a pulsed illuminating light to a sample.

The timing control apparatus controls a shutter timing of the shutter apparatus to delay the shutter timing of the shutter apparatus with respect to an irradiating timing of the illuminating apparatus so that an image of intense noise light which returns early among pulsed light returning from the sample is not picked up.

Consequently, the image pickup apparatus is able to pick up an image of light that returns later than the noise light or, in other words, light returning from a deep area of the sample at a favorable SN ratio.

The degree of scattering of illuminating light by the sample depends on the wavelength of the illuminating light and the shorter the wavelength of the illuminating light, the stronger the scattering. Therefore, in order to observe an observation object site at a deep area of a sample, it is important that illuminating light from the illuminating apparatus includes infrared light with a long wavelength which is less susceptible to scattering.

Here, in a case where an image pickup time period of one frame of the image pickup apparatus is significantly longer than an attenuation time period of image pickup light intensity, a pulse frequency of the illuminating light can be increased, and when a brightness of an obtained image is insufficient due to sample characteristics, it is more efficient if images could be integrated within one frame.

Accordingly, with the image pickup system, by setting a shutter interval of the shutter apparatus to a predetermined shutter interval that is longer than the time period required by a single pulsed light emitted by the illuminating apparatus to return but shorter than an image pickup time period of one frame of the image pickup apparatus, the image pickup apparatus is now capable of picking up an image of returned light of a plurality of pulsed lights within the image pickup time period of one frame. Consequently, since images (light intensity detected by each image pickup pixel of the image pickup apparatus) configured by a plurality of pulsed lights are integrated by the image pickup apparatus within one frame, a bright image can be obtained.

The aforementioned timing control apparatus is preferably configured such that, after setting an amount of time lag between the irradiating timing and the shutter timing to an arbitrary initial value and having the image pickup apparatus perform preliminary image pickup, the amount of time lag is varied based on a result of the image pickup to optimize a state of scattered light removal from a pickup image of the image pickup apparatus.

In this case, an amount of time lag can be optimized and a favorable pickup image can be obtained even when an adequate value of the amount of time lag between the irradiating timing and the shutter timing for removing unnecessary scattered light cannot be accurately estimated in advance or when a complete removal of unnecessary scattered light results in insufficient image brightness.

Furthermore, in each of the image pickup systems described above, if d denotes a spatial deviation between an illuminating range of the illuminating apparatus at the sample surface and an image pickup range of the image pickup apparatus, z denotes a distance from the sample surface to the observation object site in the depth direction, n denotes a refractive index of the sample, and c denotes the speed of light through air, the timing control apparatus may be configured so as to control the image pickup timing or the shutter timing so that image pickup is not performed on light exiting the sample at least before a time period $\Delta t$ provided by the following formula elapses after the illuminating light is incident to the sample.

$$\Delta t = n\left(z + \sqrt{d^2 + z^2}\right)/c$$

Here, with respect to the spatial deviation d between the illuminating range of the illuminating apparatus at the sample surface and the image pickup range of the image pickup apparatus (d=0 is assumed when an overlap exists between the illuminating range and the image pickup range), when observing an observation object site existing at a depth z from the sample surface on the edge of the image pickup range, it is assumed that the illuminating light does not scatter in mid-course inside the sample and is reflected/scattered at the observation object site.

In this case, a shortest optical path for the illuminating light to enter the sample and to return once again to the surface is configured by a straight optical path connecting the point of incidence to the sample and the observation object site and a straight optical path connecting the observation object site and an outer peripheral edge of the image pickup range which is closest to the observation object site. If Δt denotes the time that is required by the illuminating light to travel the shortest optical path, then Δt may be expressed by the formula provided above.

Light returning at a time point earlier than time Δt after entering the sample surface is limited to light scattered closer to the sample surface than the observation object site (i.e., unnecessary scattered light). Therefore, by controlling the image pickup timing so as not to pick up images of light exiting the sample before at least a time Δt has elapsed from incidence to the sample surface, the influence of unnecessary scattered light can be reliably reduced.

Here, while reducing the irradiating interval of the illuminating apparatus enables the number of integrations of pulsed light in one frame of the image pickup apparatus to be increased and is therefore advantageous, in order to reliably reduce unnecessary scattered light, incidence of a subsequent pulsed light to the image pickup apparatus must be avoided until returned light of a pulsed light incident to the sample is sufficiently attenuated. In addition, a saturation of an image pickup device due to an excessive number of pulsed light integrations must also be avoided.

In consideration thereof by arranging the irradiating interval of the illuminating apparatus and the shutter interval of the shutter apparatus to be variable, the image pickup apparatus is able to perform image pickup at an optimum brightness and image quality.

Here, even if the deviation of an image pickup timing or a shutter timing can be optimized with respect to a single pulsed light, if the distances of the illuminating apparatus and the image pickup apparatus with respect to the sample change temporally, image pickup conditions change and favorable images cannot be obtained.

In this case, it shall suffice to change the image pickup timing or the shutter timing in accordance with the change in the distances of the illuminating apparatus and the image pickup apparatus with respect to the sample so that image pickup is always performed under certain image pickup conditions. However, in many cases, an actual implementation is difficult.

Therefore, by arranging the respective image pickup systems described above so that the distances of the illuminating apparatus and the image pickup apparatus can be fixed with respect to the sample, since image pickup conditions become stable and the influence of unnecessary scattered light during observation of an observation object site is reduced, favorable image pickup can be performed.

Moreover, the present invention provides an image pickup method that uses an illuminating apparatus that illuminates a sample with an illuminating light including at least an infrared wavelength component and an image pickup apparatus that picks up an image of light from the sample illuminated by the illuminating apparatus, wherein the image pickup method: causes the illuminating apparatus to repetitively irradiate the illuminating light in a pulsed form; matches an irradiating interval of the illuminating apparatus with an image pickup interval of the image pickup apparatus; and causes an image pickup timing of the image pickup apparatus to be delayed by a predetermined time period from an irradiating timing of the illuminating apparatus so that an image of at least a portion of unnecessary scattered light occurring at the sample illuminated by the illuminating apparatus is not picked up.

With the image pickup method according to the present invention, an SN ratio of image pickup information is enhanced using the fact that intense noise light returning from near the surface of the scattering material returns earlier than light returning from the observation object site inside the scattering material.

More specifically, with the image pickup method according to the present invention, pulsed illuminating light is irradiated to a sample by controlling the irradiating timing of the illuminating apparatus. In addition, the image pickup timing of the image pickup apparatus is controlled in order to delay the image pickup timing of the image pickup apparatus with respect to an irradiating timing of the illuminating apparatus so that an image of intense noise light which returns early among pulsed light returning from the sample is not picked up.

Consequently, the image pickup apparatus is able to pickup an image of light that returns later than the noise light or, in other words, light returning from a deep area of the sample at a favorable SN ratio.

Here, the degree of scattering of illuminating light depends on the wavelength of the illuminating light and the shorter the wavelength of the illuminating light, the stronger the scattering. Therefore, in order to observe an observation object site at a deep area of the sample, it is important that illuminating light from the illuminating apparatus includes infrared light with a long wavelength.

With the present image pickup method, preferably, after setting an amount of time lag between the irradiating timing and the image pickup timing to an arbitrary initial value and having the image pickup apparatus perform preliminary image pickup, the amount of time lag is varied based on a result of the image pickup to optimize a state of scattered light removal from a pickup image of the image pickup apparatus.

In this case, an amount of time lag can be optimized and a favorable pickup image can be obtained even when an adequate value of the amount of time lag between the irradiating timing and the image pickup timing for removing unnecessary scattered light cannot be accurately estimated in advance or when a complete removal of unnecessary scattered light results in insufficient brightness of an pickup image.

Furthermore, the present invention provides an image pickup method that uses an illuminating apparatus that illuminates a sample with an illuminating light including at least an infrared wavelength component, an image pickup apparatus that picks up an image of light from the sample illuminated by the illuminating apparatus, and a shutter apparatus disposed either inside the image pickup apparatus or between the image pickup apparatus and the sample, wherein the image pickup method: causes the illuminating apparatus to repetitively irradiate the illuminating light in a pulsed form; matches an irradiating interval of the illuminating apparatus with a shutter interval of the shutter apparatus; and causes a shutter timing of the shutter apparatus to be delayed by a predetermined time period from an irradiating timing of the illuminating apparatus so that an image of at least a portion of unnecessary scattered light occurring at the sample illuminated by the illuminating apparatus is not picked up.

With the present image pickup method, an SN ratio of image pickup information is enhanced using the fact that intense noise light returning from near the surface of the scattering material returns earlier than light returning from the observation object site inside the scattering material.

More specifically, with the image pickup method, pulsed illuminating light is irradiated to a sample by controlling the irradiating timing of the illuminating apparatus.

In addition, the shutter timing of the shutter apparatus is controlled in order to delay the shutter timing of the shutter apparatus for a predetermined time with respect to an irradiating timing of the illuminating apparatus so that an image of intense noise light which returns early among pulsed light returning from the sample is not picked up.

Consequently, the image pickup apparatus is able to pick up an image of light that returns later than the noise light or, in other words, light returning from a deep area of the sample at a favorable SN ratio.

Here, in a case where an image pickup time period of one frame of the image pickup apparatus is significantly longer than an attenuation time period of image pickup light intensity, a pulse frequency of the illuminating light can be increased, and when a brightness of an obtained image is insufficient due to sample characteristics, it is more efficient if images could be integrated within one frame.

Accordingly, with the image pickup method, by setting a shutter interval of the shutter apparatus to a predetermined shutter interval that is longer than the time period required by a single pulsed light emitted by the illuminating apparatus to return but shorter than an image pickup time period of one frame of the image pickup apparatus, the image pickup apparatus is now capable of picking up an image of returned light of a plurality of pulsed lights within the image pickup time period of one frame. Consequently, since images (light intensity detected by each image pickup pixel of the image pickup apparatus) configured by a plurality of pulsed lights are integrated by the image pickup apparatus within one frame, a bright image can be obtained.

Here, with the present image pickup method, preferably, after setting an amount of time lag between an irradiating timing and a shutter timing to an arbitrary initial value and having the image pickup apparatus perform preliminary image pickup, the amount of time lag is varied based on a result of the image pickup to optimize a state of scattered light removal from a pickup image of the image pickup apparatus.

In this case, an amount of time lag can be optimized and a favorable pickup image can be obtained even when an adequate value of the amount of time lag between the irradiating timing and the shutter timing for removing unnecessary scattered light cannot be accurately estimated in advance or when a complete removal of unnecessary scattered light results in insufficient image brightness.

Moreover, in each of the image pickup methods described above, if d denotes a spatial deviation between an illuminating range of the illuminating apparatus at the sample surface and an image pickup range of the image pickup apparatus, z denotes a distance from the sample surface to the observation object site in the depth direction, n denotes a refractive index of the sample, and c denotes the speed of light through air, the image pickup timing or the shutter timing may be controlled so that image pickup is not performed on light exiting the sample at least before a time period $\Delta t$ provided by the following formula elapses after the illuminating light is incident to the sample.

$$\Delta t = n(z + \sqrt{d^2 + z^2})/c$$

With respect to the spatial deviation d between the illuminating range of the illuminating apparatus at the sample surface and the image pickup range of the image pickup apparatus (d=0 is assumed when an overlap exists between the illuminating range and the image pickup range), when observing an observation object site existing at a depth z from the sample surface on the edge of the image pickup range, assuming that the illuminating light does not scatter in midcourse inside the sample and is reflected/scattered at the observation object site, a shortest optical path for the illuminating light to enter the sample and to return once again to the surface is configured by a straight optical path connecting the point of incidence to the sample and the observation object site and a straight optical path connecting the observation object site and an outer peripheral edge of the image pickup range which is closest to the observation object site. If $\Delta t$ denotes the time that is required by the illuminating light to travel the shortest optical path, then $\Delta t$ may be expressed by the formula provided above.

Light returning at a time point earlier than time $\Delta t$ after entering the sample surface is limited to light scattered closer to the sample surface than the observation object site (i.e., unnecessary scattered light). Therefore, by controlling the image pickup timing so as not to pick up images of light exiting the sample before at least a time $\Delta t$ has elapsed from incidence to the sample surface, the influence of unnecessary scattered light can be reliably reduced.

Here, while reducing the irradiating interval of the illuminating apparatus enables the number of integrations of pulsed light in one frame of the image pickup apparatus to be increased and is therefore advantageous, in order to reliably reduce unnecessary scattered light, incidence of a subsequent pulsed light to the image pickup apparatus must be avoided until returned light of a pulsed light incident to the sample is sufficiently attenuated. In addition, a saturation of an image pickup device due to an excessive number of pulsed light integrations must also be avoided.

In consideration thereof, by adjusting and optimizing the irradiating interval of the illuminating apparatus and the shutter interval of the shutter apparatus in accordance with image pickup conditions, the image pickup apparatus is able to perform image pickup at an optimum brightness and image quality.

Here, even if the deviation of an image pickup timing or a shutter timing can be optimized with respect to a single pulsed light, if the distances of the illuminating apparatus and the image pickup apparatus with respect to the sample change temporally, image pickup conditions change and favorable images cannot be obtained.

In this case, it shall suffice to change the image pickup timing or the shutter timing in accordance with the change in distances of the illuminating apparatus and the image pickup apparatus with respect to the sample so that image pickup is always performed under certain image pickup conditions. However, in many cases, an actual implementation is difficult.

Therefore, in the respective image pickup systems described above, by fixing the distances of the illuminating apparatus and the image pickup apparatus with respect to the sample, since image pickup conditions become stable and the influence of unnecessary scattered light during observation of an observation object site is reduced, favorable image pickup can be performed.

A fourth embodiment of the present invention will now be described with reference to FIGS. 12 to 16.

In the fourth embodiment, an example in which the present invention is applied to an endoscope apparatus will be described.

Figure 12:
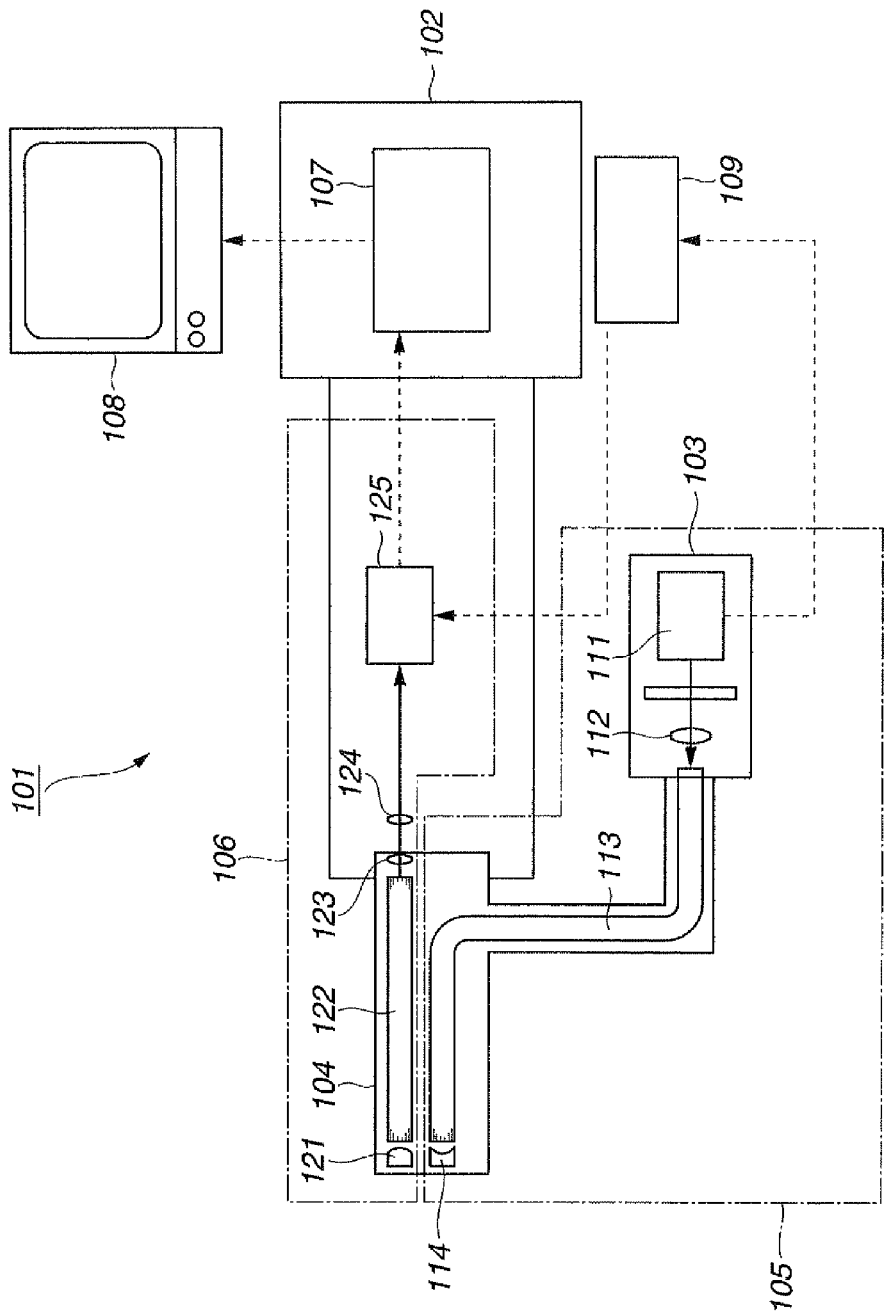
FIG. 12 is a block diagram showing a configuration of an endoscope apparatus (image pickup system) according to a fourth embodiment of the present invention.

As shown in FIG. 12, an endoscope apparatus 101 (image pickup system) according to the fourth embodiment includes: an apparatus main body 102; an operation portion 103 independent of the apparatus main body 102 and which is graspable by an operator; and an elongated and flexible insertion portion 104 to be inserted into an examination object space.

In addition, the endoscope apparatus 101 includes: an illuminating apparatus 105 that illuminates a sample with illuminating light including at least an infrared-range wavelength component; an image pickup apparatus 106 that picks up an image of light from the sample illuminated by the illuminating apparatus 105; a video processing apparatus 107 that processes an image pickup signal transmitted from the image pickup apparatus 106 and generates a video signal; a display apparatus 108 that displays a pickup image of the image pickup apparatus 106 based on the video signal outputted from the video processing apparatus 107; and a timing control apparatus 109 that controls the image pickup timing of the image pickup apparatus 106.

The illuminating apparatus 105 includes: a light source 111; a lens 112 that collects illuminating light emitted by the light source 111; a light guide 113 (optical fiber) that relays illuminating light collected by the lens 112 to a distal end of the insertion portion 4; and a lens 114 provided at the distal end of the insertion portion 104 and which shapes illuminating light irradiated from the light guide 113 and irradiates the shaped light from the distal end of the insertion portion 104.

The light source 111 and the lens 112 are housed inside the operation portion 103, and of the light guide 113, at least an end portion on an insertion portion 104 side is housed inside the insertion portion 104.

In the fourth embodiment, a laser generating apparatus that emits a pulsed laser is used as the light source 111. The laser generating apparatus is configured so as to generate a pulsed laser having a central wavelength of 1450 nm and a pulse width of 10 picoseconds at half bandwidth. In addition, the laser generating apparatus is configured so as to generate, based on a pulsed trigger signal generated by an oscillator or the like, a pulsed laser in which the trigger signal and a pulse are synchronized. The laser generating apparatus is arranged so that a pulse cyclic frequency is variable within a range from 1 Hz to 1 MHz.

The image pickup apparatus 106 includes: an objective lens 121 provided on the distal end of the insertion portion 104; a light guide 122 (optical fiber) that relays light collected by the objective lens 121 to the apparatus main body 102; a lens 123 provided on an apparatus main body 102 side edge portion of the insertion portion 104 and which relays light outputted from the light guide 122; a lens 124 provided inside the apparatus main body 102 and which relays light passed through the lens 123; and an image pickup device 125 to which light relayed by the lens 124 is inputted. The lens 124 and the image pickup device 125 are respectively housed in the apparatus main body 102.

The image pickup device 125 is configured so as to convert an image formed by the objective lens 121 and relayed by the light guide 122, the lens 123 and the lens 124 into an image pickup signal and to output the signal to the video processing apparatus 107. In the present embodiment, as the image pickup device 125, for example, a CCD (charge coupled device) apparatus is used. An electronic shutter that opens and closes an image pickup gate is provided at the CCD apparatus.

The timing control apparatus 109 is configured so as to use an irradiating timing of the illuminating apparatus 105 detected based on the trigger signal that drives the illuminating apparatus 105 for controlling an image pickup timing of the image pickup apparatus 106.

The timing control apparatus 109 is configured so as to match an irradiating interval of the illuminating apparatus 105 with an image pickup interval of the image pickup apparatus 106 and to send an image pickup timing signal to the image pickup apparatus 106 so that image pickup is performed after a predetermined time lag from an irradiating timing in order to prevent at least a portion of unnecessary scattered light generated by the sample illuminated by the illuminating apparatus 105 from being picked up.

More specifically, after receiving a trigger signal, the timing control apparatus 109 outputs an image pickup timing signal after a predetermined time lag. The image pickup timing signal is arranged to be inputted to the image pickup device 125. The image pickup device 125 is arranged to perform image pickup in synchronization with the image pickup timing signal.

Hereinafter, an image pickup method of a sample by the endoscope apparatus 101 configured as shown above will be described.

First, a principle of image pickup by the endoscope apparatus 101 will be described.

Figure 13A:
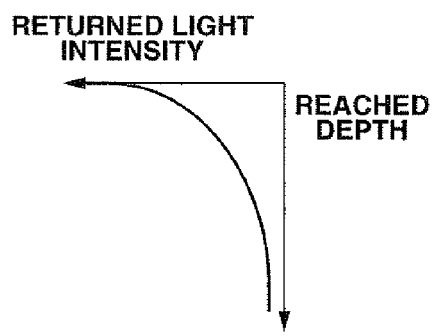
FIG. 13A is a graph showing a relationship between an optical path and intensity of light in a case where light incident into scattering material returns to a surface.
Figure 13B:
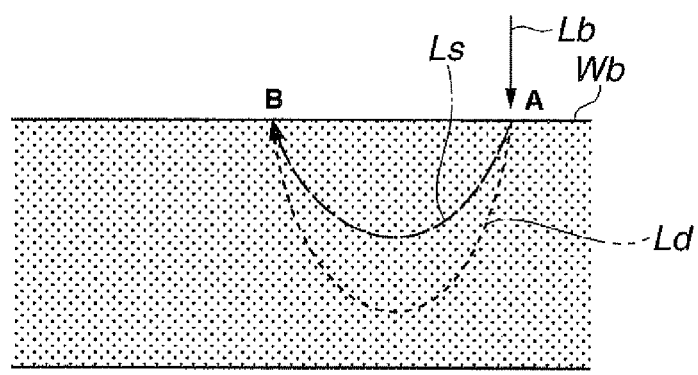
FIG. 13B is a conceptual diagram showing a relationship between an optical path and intensity of light in a case where light incident into scattering material returns to a surface.

FIG. 13B shows a schematic diagram regarding the behavior of light Lb incident into a scattering material Wb. In FIG. 13B, examples of a path of light outputted to a point B on an incident-side among light incident to a point A of the scattering material Wb are indicated by the dashed line and the dashed-two dotted line. Although the actual light Lb is subject to multiple scattering by the scattering material Wb and therefore cannot be accurately depicted, the path indicated by the dashed line and the path indicated by the dashed-two dotted line in FIG. 13B respectively represent approximate optical paths (average optical paths) in the scattering material Wb.

The fact that light Ls returning after passing near the surface of the scattering material Wb (the light traveling the path indicated by the dashed-two dotted line) has a shorter average optical path than light Ld that has passed through a deep area (the light traveling the path indicated by the dashed line) and therefore returns earlier is apparent also from FIG. 12 and is also shown in the aforementioned prior art documents. In addition, as depicted in the graph shown in FIG. 13A, there is a fact that light returning from near the surface of the scattering material Wb has a higher intensity while light returning from a deeper area has a lower intensity.

When actually observing an observation object site inside a scattering material Wb, it is extremely difficult to observe weak signal light (light Ld) from an observation object site at a deep position in the scattering material Wb because strong light Ls returning from near the surface of the scattering material Wb becomes noise light and acts as an obstacle. In particular, this fact becomes more evident when the observation object site is an absorbing material that absorbs light because the weak signal light is further absorbed and weakened.

In consideration thereof, with the endoscope apparatus 1001 according to the fourth embodiment, using the fact that strong noise light returning from near the surface of the scattering material Wb returns early, images of strong noise light returning early are arranged not to be picked up by using pulsed light as the illuminating light and delaying the image pickup timing of the image pickup apparatus 106 with respect to returning pulsed light, thereby arranging images of signal light returning from a deep area of the scattering material Wb to be picked up at a favorable SN ratio.

Here, since a degree of scattering of illuminating light depends on the wavelength of the illuminating light and the shorter the wavelength, the stronger the scattering, in order to observe an observation object site P at a deep area in the scattering material Wb, it is important that infrared light having a long wavelength is included in the illuminating light and that the image pickup apparatus 106 is capable of detecting infrared light.

Figure 14:
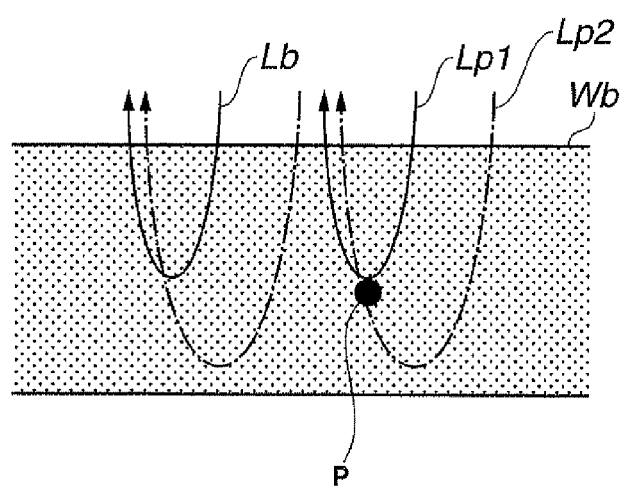
FIG. 14 is a diagram showing a concept of observation image formation when observing absorbing material in scattering material.

In the endoscope apparatus 101, as shown in FIG. 14, the image pickup apparatus 106 may be arranged to instantaneously pickup an image of light Lp1 exactly reflected and scattered at the observation object site P among light Lb incident to the scattering material Wb to observe the observation object site P based on a contrast of a pickup image created from a difference in intensity between light Lp1 that has passed through the observation object site P that is an absorbing body and light Lb that has not passed through the observation object site P. However, it is more advantageous to pick up an image by also including light Lp2 that has been scattered at an area deeper than the observation object site P and which passes through the observation object site P.

Therefore, in the fourth embodiment, instead of instantaneously picking up an image by delaying the image pickup timing of the image pickup apparatus 106, image pickup is arranged to be performed using all of the light that returns within an image pickup time of one frame of the image pickup apparatus 106. At this point, since the cyclic interval of the pulsed light and the image pickup interval of the image pickup apparatus 106 are approximately consistent, an observation image with a favorable SN ratio can be obtained without picking up an image of at least a portion of unnecessary scattered light that becomes noise in every frame.

A slightly more detailed description will now be given with reference to FIG. 15. When pulsed light is irradiated from the illuminating apparatus 105, strong scattering light from the vicinity of the surface of the scattering material Wb among the pulsed light returns first to the image pickup apparatus 106. The deeper the reached depth of pulsed light from the surface of the scattering material Wb, the greater the delay of arrival at the image pickup apparatus and the greater the attenuation in regards to light intensity. Thus, by performing image pickup by delaying the image pickup timing of the image pickup apparatus 106 by a predetermined amount with respect to the irradiating timing of the illuminating apparatus 105 (by delaying an opening timing of the image pickup gate of the image pickup device 125 by a predetermined amount with respect to the irradiating timing of the illuminating apparatus 105), an image free from the influence of strong scattered light from the vicinity of the surface can be picked up.

Figure 15:
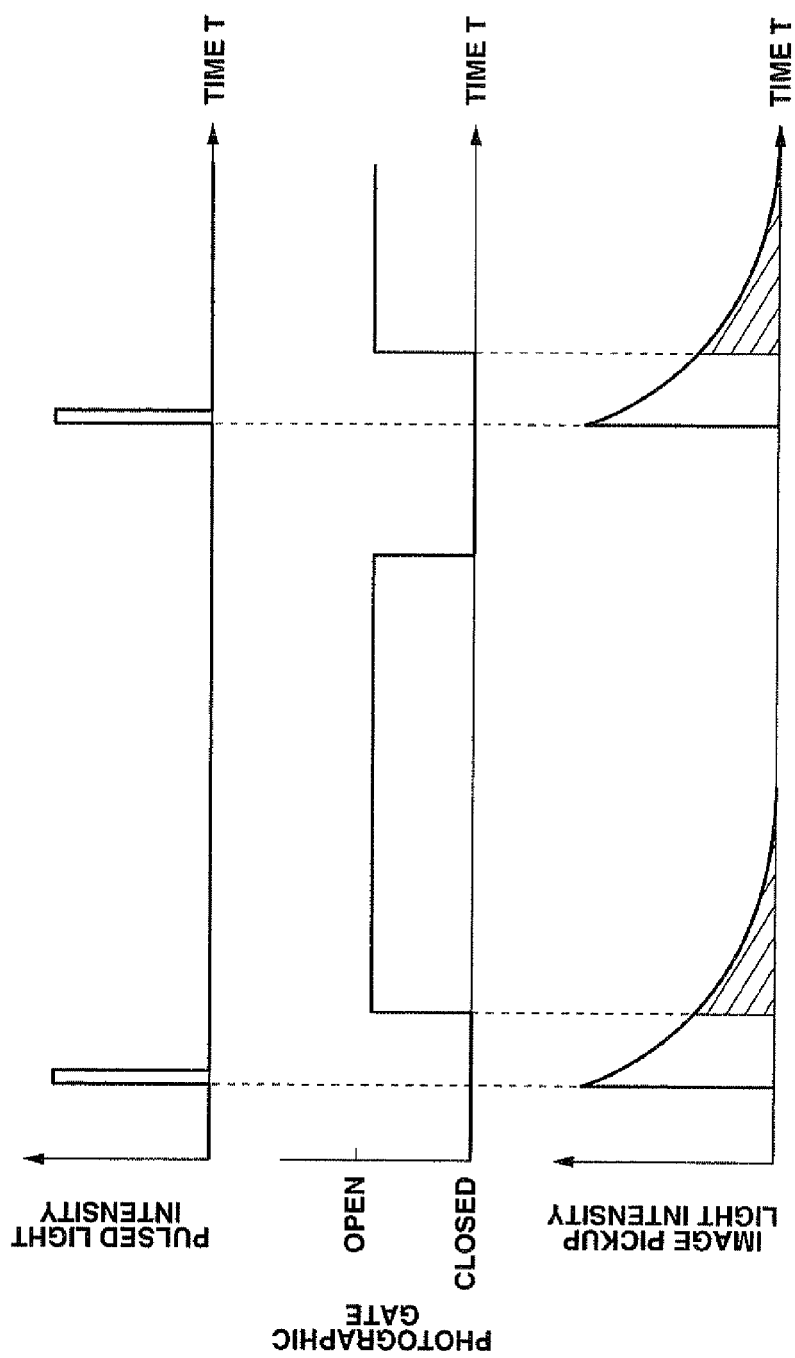
FIG. 15 is a diagram showing temporal relationships with respect to pulsed light intensity of an illuminating apparatus, operations of an image pickup gate of an image pickup apparatus, and image pickup light intensity of an image pickup apparatus.

In addition, in the case of a configuration in which the predetermined time period is set to one frame and the image pickup apparatus 106 integrates light incident to the image pickup device 125 within one frame to obtain a pickup image instead of performing instantaneous image pickup, by setting the time period in which images for one frame is picked up to be significantly longer than a time period necessary for all components of the irradiated pulsed light to return, images of light in the shaded portion among the graph representing image pickup light intensity shown in the lower third of FIG. 15 can be picked up. Therefore, image pickup can be performed brighter than performing instantaneous image pickup of light exactly reflected/scattered at the observation object site P.

When actually performing image pickup, there may exist a time lag from the time a trigger signal pulse of the illuminating apparatus 105 is generated to the time the illuminating apparatus 105 actually irradiates pulsed light, or a time lag from the time the timing control apparatus 109 issues an image pickup instruction to the image pickup apparatus 106 to the time image pickup is actually performed by the image pickup apparatus 106.

Furthermore, an amount of time lag of the image pickup timing with respect to the irradiating timing must be set also taking into consideration a time period required for a light emitted by a light source of the illuminating apparatus to be transmitted through an optical system including the illuminating apparatus 105, and the lens, light guides (e.g., optical fibers) and the like of the image pickup apparatus 106.

Although a suitable value of the amount of time lag can be estimated in advance to a certain extent, there are cases where a suitable value cannot be accurately known. In addition, while an absence of unnecessary scattered light is always better, due to the relationship with the brightness of an image, there may be cases where an observation can be performed easier when brighter even if a certain amount of unnecessary scattered light remains and contrast is somewhat inferior.

Therefore, favorable pickup images can be obtained by setting an amount of time lag between the irradiating timing and the image pickup timing to an arbitrary initial value and having the image pickup apparatus 106 perform preliminary image pickup and then varying the amount of time lag based on a result of the preliminary image pickup to optimize a state of scattered light removal from a pickup image of the image pickup apparatus 106.

Here, the optimization processing of the aforementioned amount of time lag may be configured such that either a user of the endoscope apparatus 101 manually sets an amount of time lag, or the timing control apparatus 109 automatically adjusts an amount of time lag based on contrast information of a pickup image of the image pickup apparatus 106 obtained from an output of the video processing apparatus 107 or on information on the brightness of the pickup image so that contrast, brightness, or a balance of the two is optimized.

Figure 16:
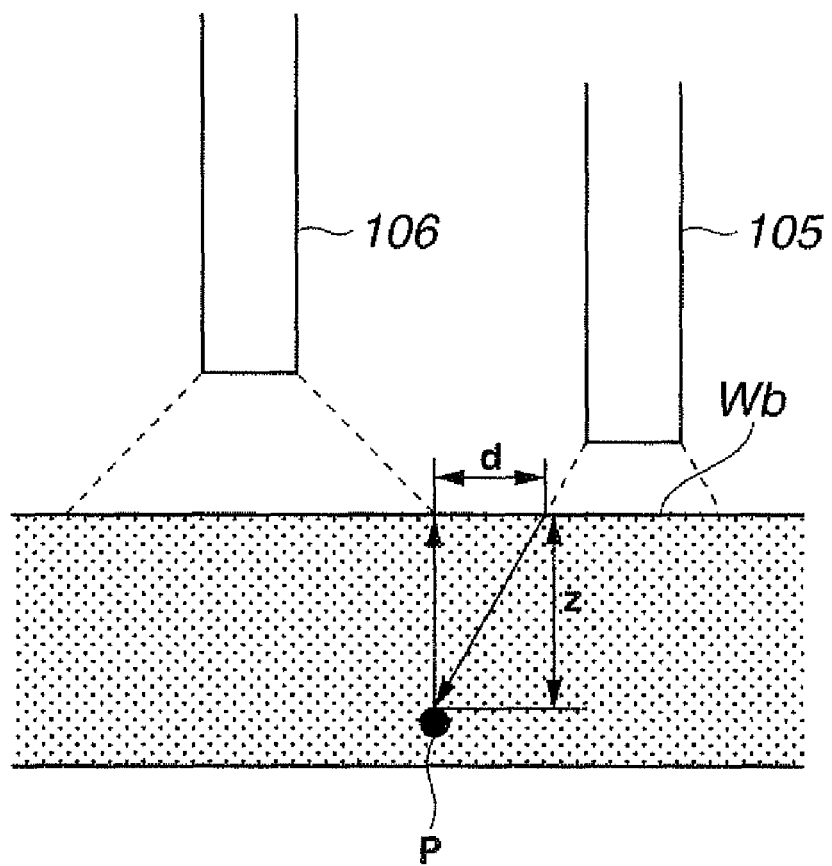
FIG. 16 is a conceptual diagram showing a behavior of illuminating light when image pickup is performed by an endoscope apparatus according to the fourth embodiment of the present invention.

Furthermore, in the endoscope apparatus 101, as shown in FIG. 16, the timing control apparatus 109 is preferably configured such that if d denotes a spatial deviation between the illuminating range of the illuminating apparatus 105 at the sample (scattering material Wb) surface and the image pickup range of the image pickup apparatus 106, z denotes a distance from the sample surface to the observation object site P in the depth direction, n denotes a refractive index of the sample, and c denotes the speed of light through air, the image pickup timing is controlled so that image pickup is not performed on light exiting the sample at least before a time period Δt provided by the following formula (I) elapses after the illuminating light is incident to the sample.

$$\Delta t = n\left(z + \sqrt{d^2 + z^2}\right)/c \tag{1}$$

Here, with respect to the spatial deviation d between the illuminating range of the illuminating apparatus 105 at the sample surface and the image pickup range of the image pickup apparatus 106 (d=0 is assumed when an overlap exists between the illuminating range and the image pickup range), when observing an observation object site P existing at a depth z from the sample surface on the edge of the image pickup range, it is assumed that the illuminating light does not scatter in mid-course inside the sample and is reflected/scattered at the observation object site P.

In this case, a shortest optical path for the illuminating light to enter the sample and to return once again to the surface is configured by a straight optical path connecting the point of incidence to the sample and the observation object site P and a straight optical path connecting the observation object site P and an outer peripheral edge of the image pickup range which is closest to the observation object site P. If $\Delta t$ denotes the time that is required by the illuminating light to travel the shortest optical path, then $\Delta t$ may be expressed by formula (1) provided above.

Light returning at a time point earlier than time $\Delta t$ after entering the sample surface is limited to light scattered closer to the sample surface than the observation object site P (i.e., unnecessary scattered light). Therefore, by controlling the image pickup timing so as not to pick up images of light exiting the sample before at least a time $\Delta t$ has elapsed from incidence to the sample surface, the influence of unnecessary scattered light can be reliably reduced.

Here, even if the deviation of an image pickup timing or a shutter timing can be optimized with respect to a single pulsed light, if the distances of the illuminating apparatus 105 and the image pickup apparatus 106 with respect to the sample change temporally, image pickup conditions change and favorable images cannot be obtained.

In this case, it shall suffice to change the image pickup timing or the shutter timing in accordance with the change in the distances of the illuminating apparatus 105 and the image pickup apparatus 106 with respect to the sample so that image pickup is always performed under certain image pickup conditions. However, in many cases, an actual implementation is difficult.

Therefore, by arranging the endoscope apparatus 101 described above so that the distances of the illuminating apparatus 105 and the image pickup apparatus 106 can be fixed with respect to the sample, since image pickup conditions become stable and the influence of unnecessary scattered light during observation of an observation object site is reduced, favorable image pickup can be performed.

More specifically, it is preferable to provide either a fixing apparatus that fixes the distal end of the insertion portion 104 to a sample or a position adjusting apparatus which maintains a constant distance between the sample and the distal end of the insertion portion 104 by varying the position of the distal end of the insertion portion 104 so as to follow the fluctuation of the sample.

With the endoscope apparatus 101 shown in the fourth embodiment, an image of a sample is picked up based on the principle described above.

An example of an image pickup method according to the endoscope apparatus 101 will be described below.

The example assumes that blood vessels (arteries and veins) embedded in a living body tissue (sample) covered by visceral fat are to be observed.

In the case of the sample, fat is a scattering body and the blood vessels correspond to an absorbing body. In the present example, a depth z of the blood vessels from the fat surface is assumed to be approximately 5 mm. The relationships between the sample and the illuminating apparatus 105 and the image pickup apparatus 106 are assumed to be the same as the relationships shown in FIG. 16, and in the case of the present example, d=0. Although the refractive index of fat varies due to individual differences and the environment and therefore cannot be accurately determined, a value of approximately 1.5 is assumed. Since the speed of light through air is 0.3 mm/ps (picoseconds), in the present example, $\Delta t$=50 ps.

Therefore, with the present example, an image pickup timing signal is controlled by the timing control apparatus 109 so that image pickup of light exiting the sample before at least 50 ps elapses from incidence of pulsed light to the sample is not performed. However, blood vessels do not necessarily always exist on an edge side of an illuminating side of an image pickup range. Since 50 ps is a shortest time period for a signal light to return from the blood vessels, in a case where blood vessels exist around the center of the image pickup range, a delay to a longer time period than 50 ps is preferable. Therefore, in the present example, a phase of the image pickup timing signal (in other words, amount of temporal deviation) is arranged to be variable within an accuracy of 5 ps.

Furthermore, since a CCD apparatus that is the image pickup device 125 is capable of performing image pickup at 1000 fps (frames per second), the frequency of the pulsed laser emitted by the pulsed laser apparatus that is the light source 111 is set at 1 kHz in accordance thereto. Under such conditions, the image pickup device 125 acquires one frame in 1 ms (millisecond). Here, since the noise increases if the image pickup gate of the image pickup device 125 is open even during a period in which light no longer returns from the sample, the present example is set so that the image pickup gate is opened by an electronic shutter built into the image pickup device 125 for only 1 μs (microsecond).

(Fifth Embodiment)

A fifth embodiment of the present invention will now be described with reference to FIGS. 17 and 18.

Figure 17:
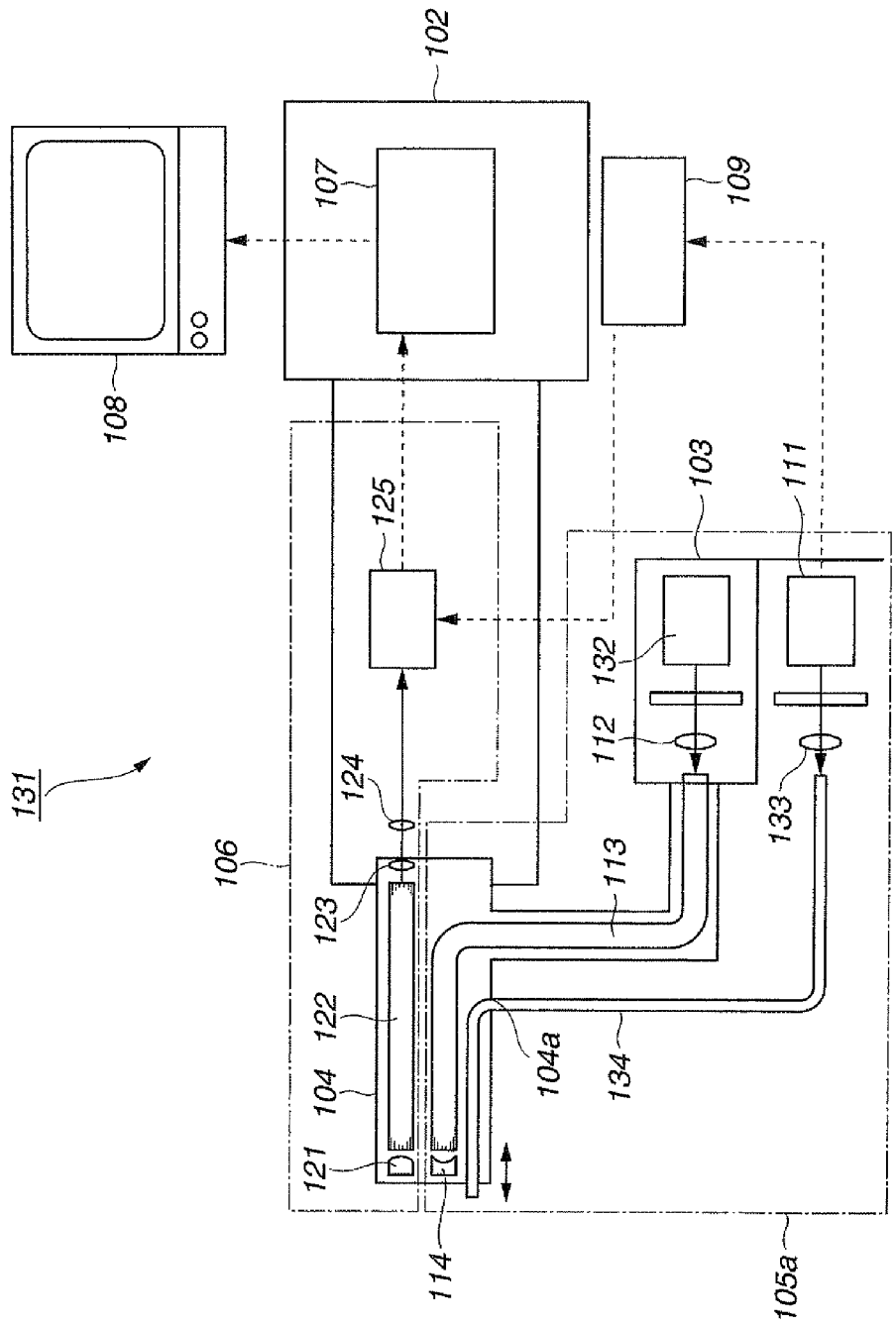
FIG. 17 is a block diagram showing a configuration of an endoscope apparatus according to a fifth embodiment of the present invention.

As shown in FIG. 17, an endoscope apparatus 131 according to the fifth embodiment is the endoscope apparatus 101 according to the fourth embodiment, wherein an illuminating apparatus 105*a* is used in place of the illuminating apparatus 105. Hereinafter, similar or same members as in the endoscope apparatus 101 shown in the fourth embodiment shall be denoted using same reference characters and detailed descriptions shall be omitted.

The illuminating apparatus 105*a* is configured such that, in the illuminating apparatus 105 shown in the fourth embodiment, an endoscope observation light source 132 (for example, a halogen lamp or a xenon lamp) is provided in addition to a photographic light source 111.

In the fifth embodiment, the illuminating apparatus 105*a* is configured such that, in the illuminating apparatus 105 shown in the fourth embodiment, the light source 132 is provided in the operation portion 103 in place of the light source 111, whereby light emitted by the light source 132 travels through the lens 112, the light guide 113, the lens 114, and exits the distal end of the insertion portion 104.

In addition, in the illuminating apparatus 105*a*, the light source 111 is provided outside the operation portion 103, and a lens 133 that collects light emitted by the light source 111 and a light guide 134 (optical fiber) that relays light collected by the lens 133 are provided.

The light guide 134 is inserted into the insertion portion 104 from a central portion of the insertion portion 104. In addition, the light guide 134 is arranged to be fixable to the insertion portion 104 in a state where the distal end of the light guide 134 protrudes from the distal end of the insertion portion 104. In the fifth embodiment, as the insertion portion 104, an insertion portion is used which has a forceps opening 104*a* into which a forceps is inserted. The light guide 134 is inserted into the forceps opening.

Figure 18:
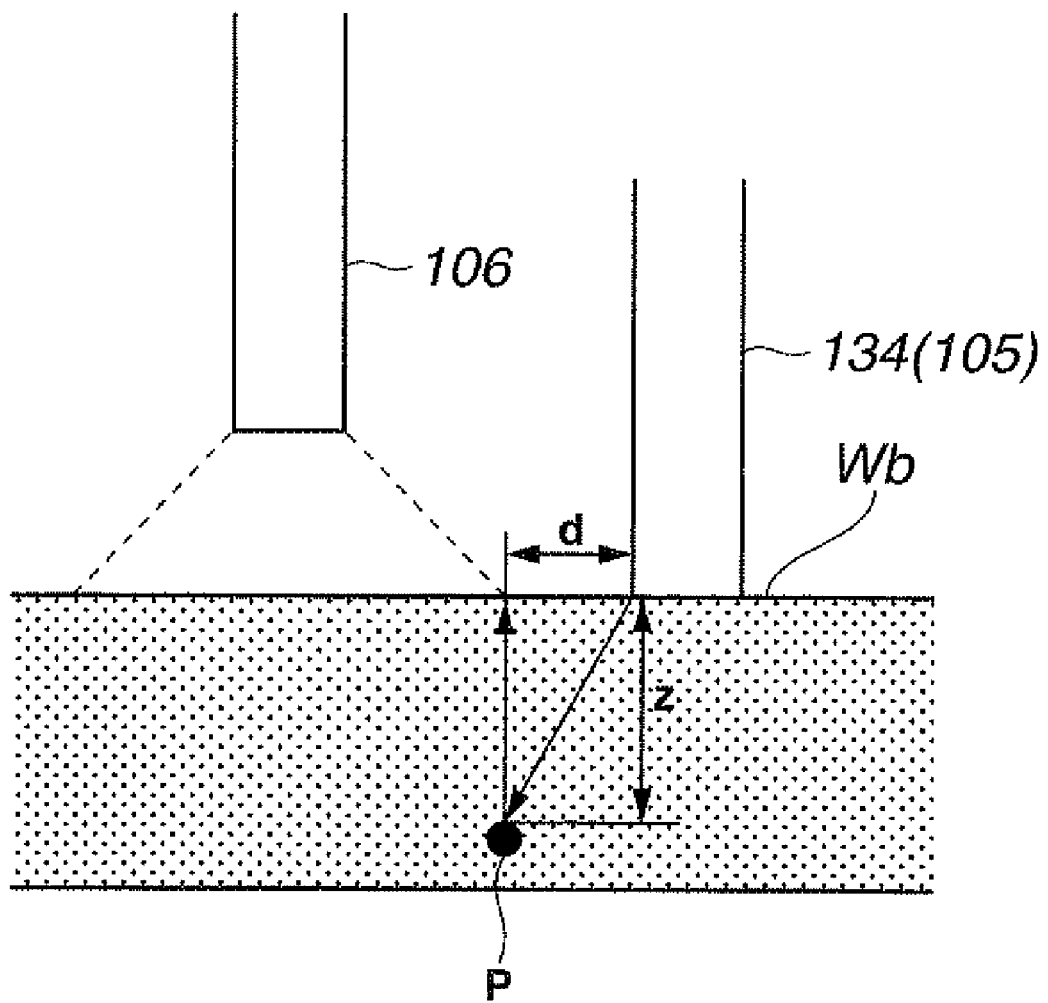
FIG. 18 is a conceptual diagram showing a behavior of illuminating light when image pickup is performed by an endoscope apparatus according to the fifth embodiment of the present invention.

With the endoscope apparatus 131, as shown in FIG. 18, by bringing a distal end of the light guide 134 into close contact to a surface of a sample (scattering material Wb) in a state where the distal end of the light guide 134 is projected from the insertion portion 104, illuminating light irradiated from the distal end of the light guide 134 can be arranged to be directly incident to the sample surface. Consequently, since light reflected at the sample surface is no longer directly incident to the image pickup apparatus 106, images can be picked up at favorable contrast when picking up images of blood vessels inside fat or the like.

In addition, in a state where the distal end of the light guide 134 is projected from the insertion portion 104 as described above, by fixing the light guide 134 to the insertion portion 104 and bringing the distal end of the light guide 134 into close contact with the sample surface, the distances of the illuminating apparatus 105 and the image pickup apparatus 106 with respect to the sample can be fixed.

In the fifth embodiment, it is assumed that the spatial deviation d between an illuminating range of the illuminating apparatus 105 at the sample surface and an image pickup range of the image pickup apparatus 106 is 3 mm and the depth z of the observation object site P from the sample surface is 5 mm (the same as the fourth embodiment). Therefore, since $\Delta t \approx 54.1$ ps, in the fifth embodiment, an image pickup timing signal is controlled so that image pickup of light exiting the sample before at least 55 ps elapses from incidence of pulsed light to the sample is not performed. Moreover, also in the fifth embodiment, the phase of the image pickup timing signal is arranged to be variable to an accuracy of 5 ps in the same manner as the fourth embodiment. Furthermore, in the fifth embodiment, conditions including a CCD frame rate, a pulsed laser frequency and the like are the same as the conditions shown in the fourth embodiment.

Incidentally, while the fifth embodiment has been arranged so that the light guide 134 is to be inserted from the forceps opening of the insertion portion 104, it is needless to say that the light guide 134 may be provided separately from the insertion portion 104. By arranging the light guide 134 to be separate from the insertion portion 104, a degree of freedom of the value of d shown in FIG. 18 increases. In this manner, by changing the value of d, the value of $\Delta t$ can be controlled to a value suitable for practical situations.

(Sixth Embodiment)

A sixth embodiment of the present invention will now be described with reference to FIGS. 19 to 21.

Figure 19:
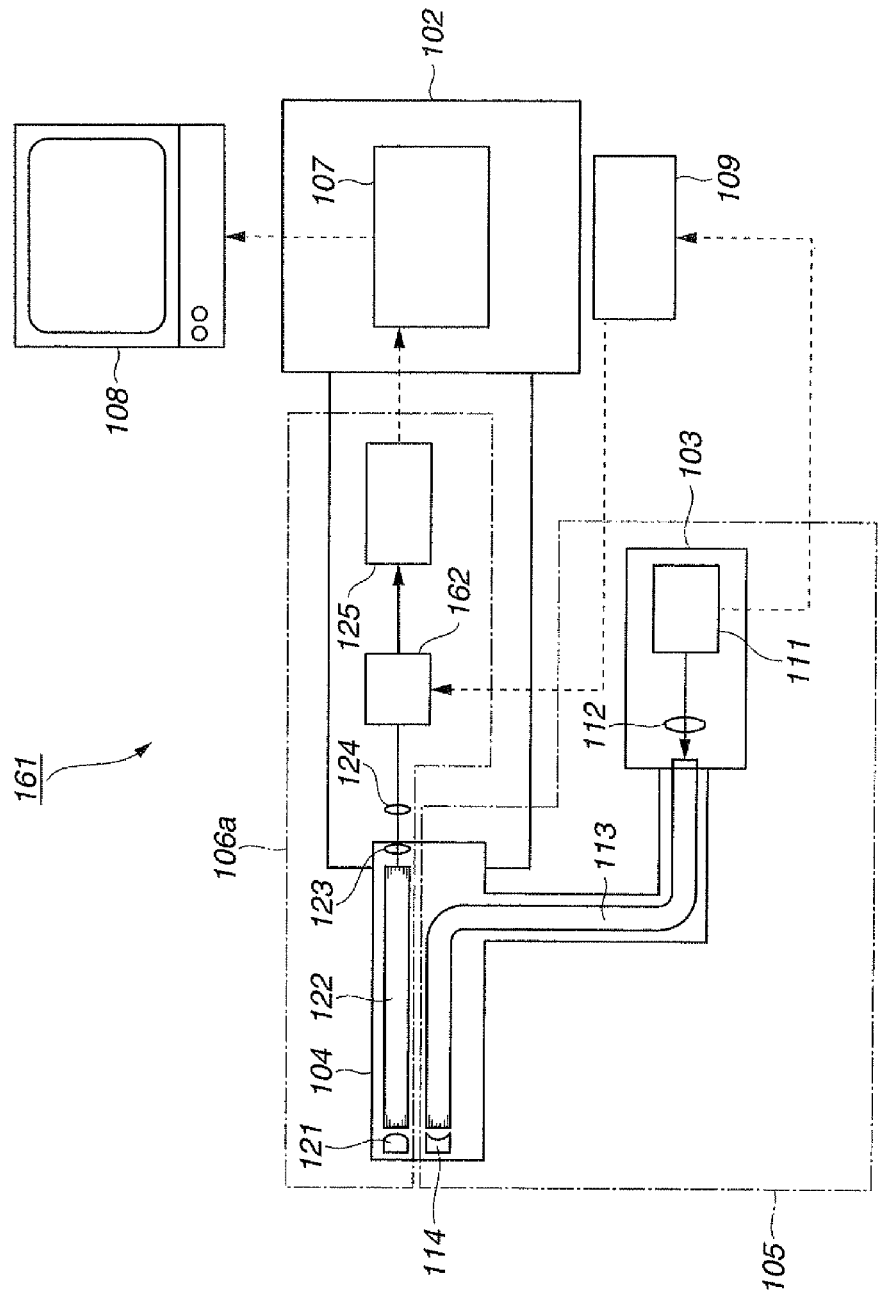
FIG. 19 is a block diagram showing a configuration of an endoscope apparatus according to a sixth embodiment of the present invention.

As shown in FIG. 19, an endoscope apparatus 161 according to the sixth embodiment is the endoscope apparatus 101 according to the fourth embodiment, wherein an image pickup apparatus 106a is used in place of the image pickup apparatus 106. Hereinafter, similar or same members as in the endoscope apparatus 101 shown in the fourth embodiment shall be denoted using same reference characters and detailed descriptions shall be omitted.

The image pickup apparatus 106a is the image pickup apparatus 106 shown in the fourth embodiment, wherein a shutter apparatus 162 for blocking incidence of light returned from the sample to the image pickup device 125 is provided.

In the present embodiment, the timing control apparatus 109 is configured so that a shutter timing signal delayed by a predetermined time period with respect to an illuminating timing signal of the illuminating apparatus 105 (a trigger signal of the light source 111) is inputted to the shutter apparatus 162. In addition, in a stage previous to the image pickup device 125, the shutter apparatus 162 is configured by a mechanical shutter that opens for a predetermined time period in synchronization with a shutter timing signal emitted by the timing control apparatus 109.

In other words, the timing control apparatus 109 is configured so as to match an irradiating interval of the illuminating apparatus 105 with a shutter interval of the shutter apparatus 162, and send a shutter timing signal to the shutter apparatus 162 so that the shutter apparatus 162 operates after a predetermined time delay from the irradiating timing of the illuminating apparatus 105.

Consequently, an image of at least a portion of unnecessary scattered light generated at the sample illuminated by the illuminating apparatus is arranged not to be picked up by the image pickup apparatus 106a.

Also with the endoscope apparatus 161, the timing control apparatus 109 is preferably configured such that, after setting an amount of time lag between an irradiating timing and a shutter timing to an arbitrary initial value and having the image pickup apparatus 106a perform preliminary image pickup, the amount of time lag is varied based on a result of the image pickup to optimize a state of scattered light removal from a pickup image of the image pickup apparatus 106a.

By adopting the configuration described above, an amount of time lag can be optimized and a favorable pickup image can be obtained even when an adequate value of the amount of time lag between the irradiating timing and the shutter timing for removing unnecessary scattered light cannot be accurately estimated in advance or when a complete removal of unnecessary scattered light results in insufficient image brightness.

In addition, the endoscope apparatus 161 is preferably configured so that, in order to prevent images of unnecessary scattered light from being picked up, shutter timing is controlled so as not to pick up images of light exiting the sample before at least a time $\Delta t$ expressed by formula (I) presented above has elapsed from incidence of illuminating light to the sample.

In the sixth embodiment, a frequency at which the shutter apparatus 162 opens the shutter is set to 1 MHz and the shutter is arranged to open for 100 ns (nanoseconds) at the described frequency (every 1 μs). In accordance therewith, the frequency of pulsed light emitted by the light source 111 is also set to 1 MHz.

In the sixth embodiment, since the positional relationship of the illuminating apparatus 105 and the image pickup apparatus 106 with respect to the sample is assumed to be the same as the positional relationship shown in the fourth embodiment, $\Delta t=50$ ps. Therefore, with the present embodiment, the timing control apparatus 109 controls an image pickup timing signal so that light exiting the sample before at least 50 ps elapses from incidence of pulsed light to the sample does not penetrate the shutter apparatus 162.

Figure 20:
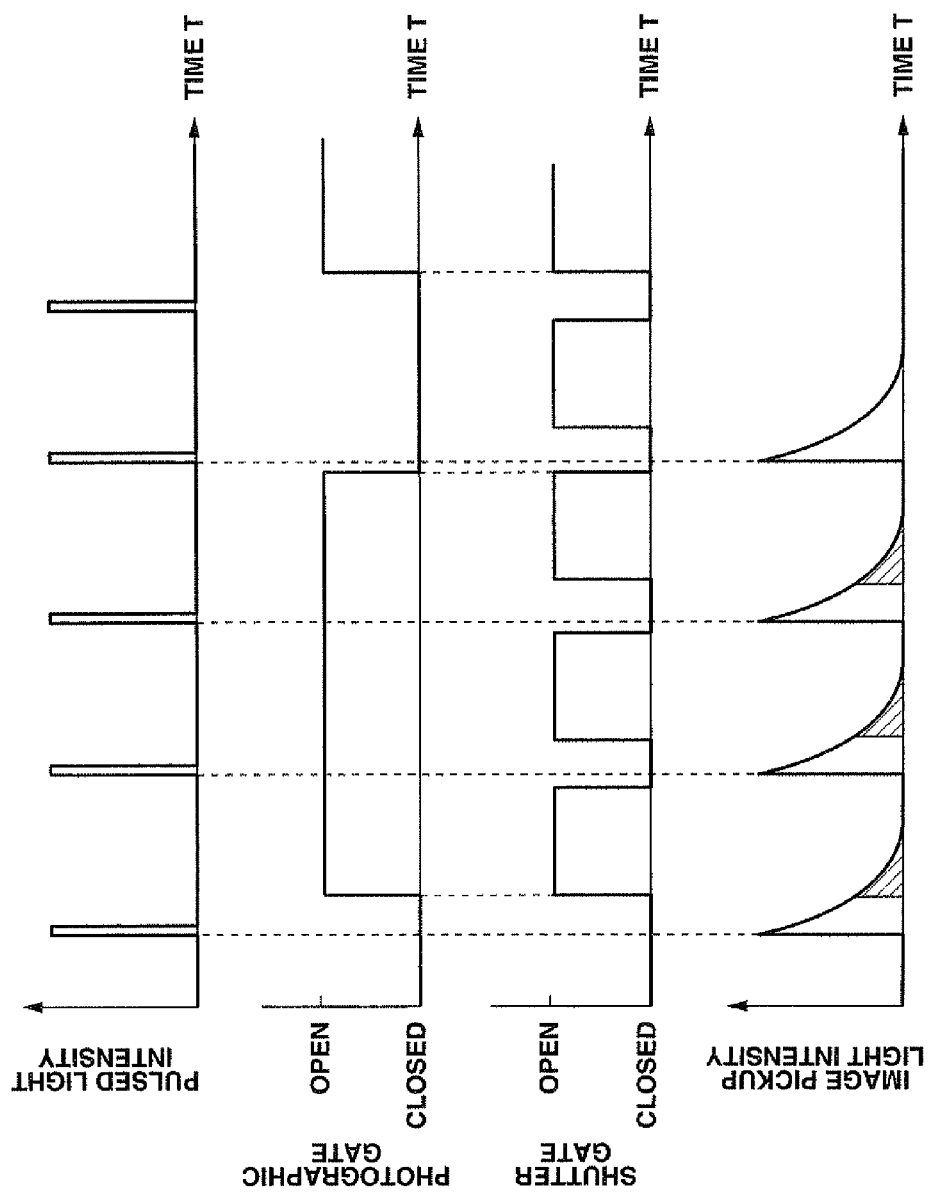
FIG. 20 is a diagram showing temporal relationships with respect to pulsed light intensity of an illuminating apparatus, operations of an image pickup gate of an image pickup apparatus, operations of a shutter gate, and image pickup light intensity of an image pickup apparatus in an endoscope apparatus according to the sixth embodiment of the present invention.
Figure 21:
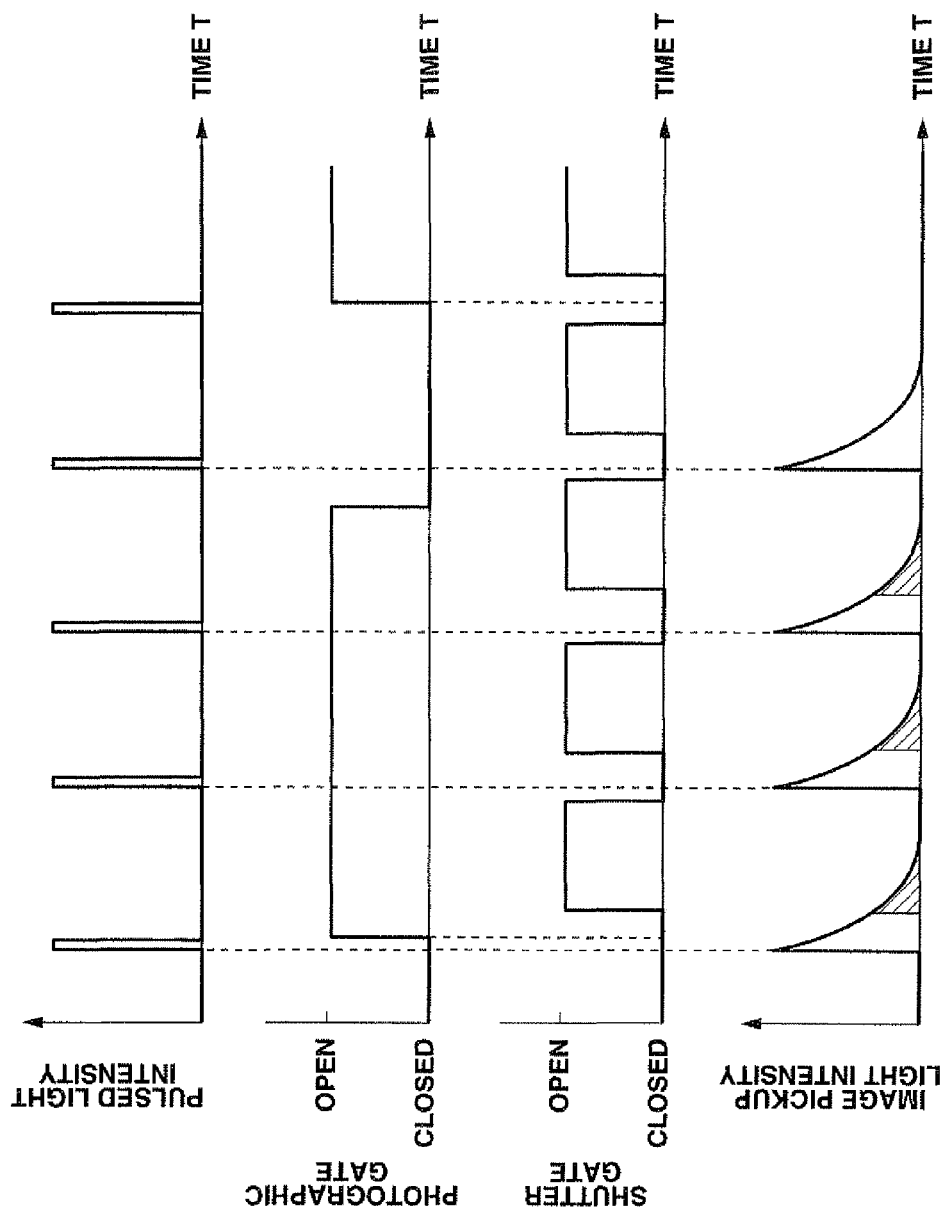
FIG. 21 is a diagram showing temporal relationships with respect to pulsed light intensity of an illuminating apparatus, operations of an image pickup gate of an image pickup apparatus, operations of a shutter gate, and image pickup light intensity of an image pickup apparatus in an endoscope apparatus according to the sixth embodiment of the present invention.

At this point, while an opening timing of the shutter apparatus 162 and an opening timing of an image pickup gate of the image pickup device 125 are desirably consistent with each other as shown in FIG. 20, since both a shutter timing and an image pickup timing must be controlled in order to achieve such an arrangement, control becomes complex. However, even if the opening timing of the image pickup gate is upset and a state such as shown in FIG. 21 is created, since unnecessary scattered light does not enter the image pickup device 125, only the opening timing of the shutter gate is controlled in the present embodiment.

Although the sixth embodiment is similar to the fourth embodiment in that a CCD apparatus is used as the image pickup device 125, the sixth embodiment is arranged so that image integration in one frame can be controlled by controlling a gate interval of an electronic shutter inside the CCD apparatus.

For example, if the gate interval of the electronic shutter is set to 100 ps, since the shutter apparatus 162 opens for 100 ns every 1 μs, 100 pulses worth of signals can be integrated to pickup images for one frame.

Here, it is needless to say that, when a change in the number of integrations in one frame is desired, the gate interval of the electronic shutter may be changed or the shutter timing frequency and the pulse frequency of the pulsed light may be changed.

While reducing the irradiating interval of the illuminating apparatus 105 increases the number of integrations of pulsed light in one frame of the image pickup apparatus 106 and is therefore advantageous, in order to reliably reduce unnecessary scattered light, incidence of a subsequent pulsed light to the image pickup apparatus 106 must be avoided until returned light of a pulsed light incident to the sample is sufficiently attenuated. In addition, a saturation of the image pickup device 125 due to an excessive number of pulsed light integrations must also be avoided.

In consideration thereof, by arranging the irradiating interval of the illuminating apparatus 105 and the shutter interval of the shutter apparatus 162 to be variable, the image pickup apparatus 106 is able to perform image pickup at an optimum brightness and image quality.

Moreover, in the present embodiment, while a configuration is shown in which the endoscope apparatus 101 shown in the fourth embodiment is provided with the shutter apparatus 162, the configuration is not restrictive and a configuration may be adopted in which the endoscope apparatus 131 shown in the fifth embodiment is provided with the shutter apparatus 162.

(Seventh Embodiment)

Figure 22:
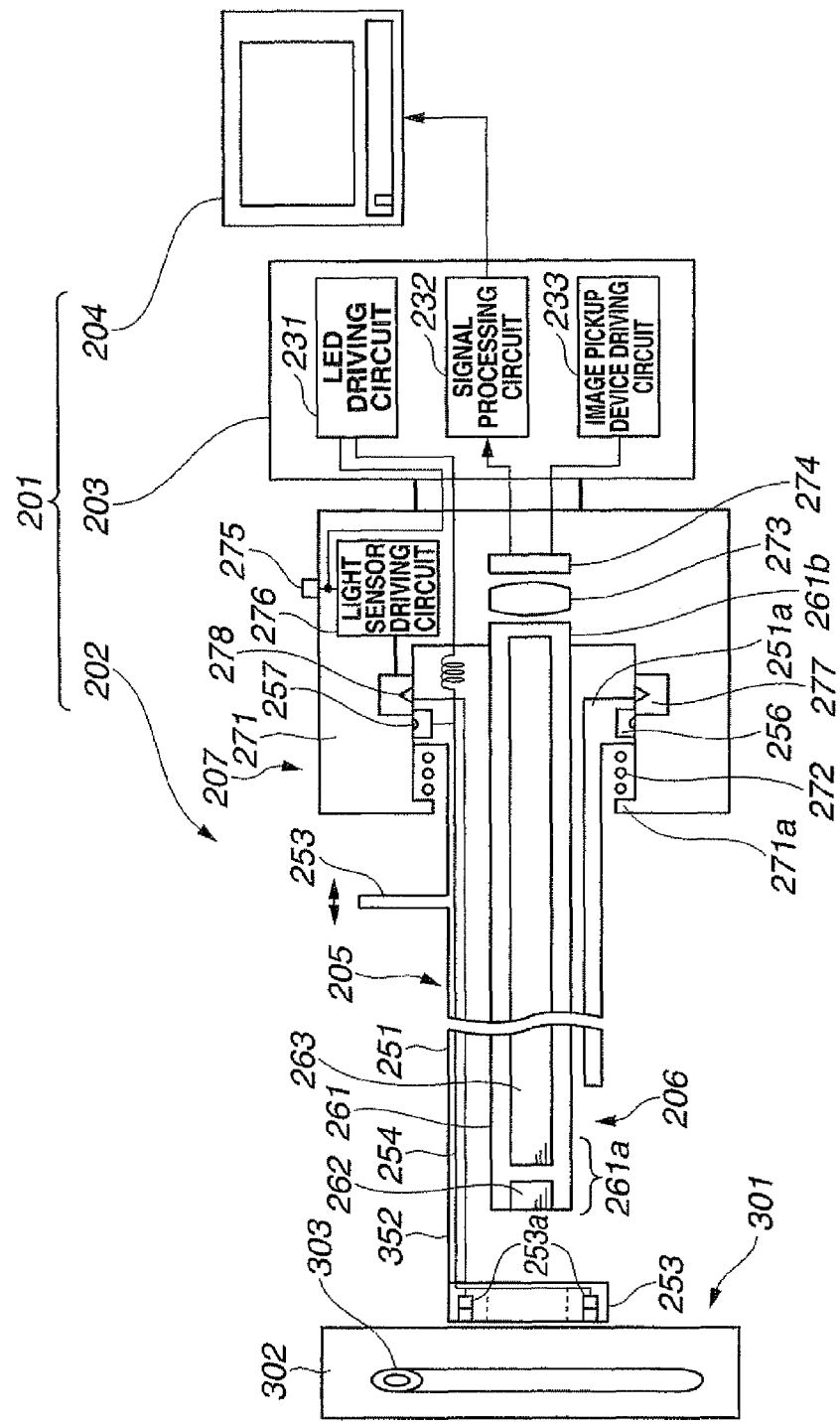
FIG. 22 is a diagram showing an example of a configuration of substantial portions of an image pickup system according to a seventh embodiment of the present invention.
Figure 23:
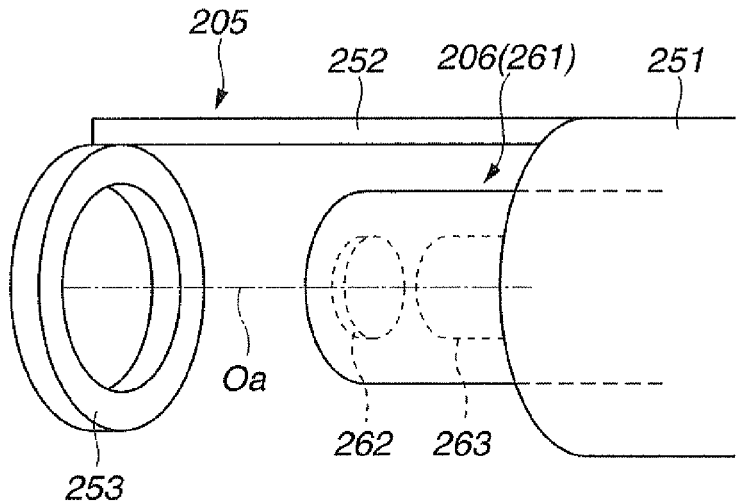
FIG. 23 is a perspective view showing a distal end-side configuration of an illuminating unit and an endoscope main body shown in FIG. 22.
Figure 24:
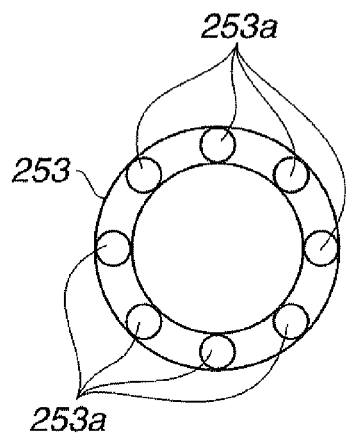
FIG. 24 is a front view showing a configuration of an illuminating portion provided at the illuminating unit shown in FIG. 22.
Figure 25:
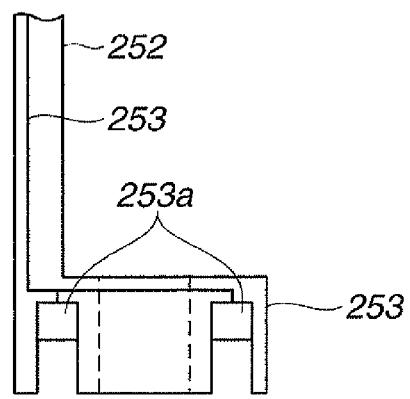
FIG. 25 is a cross sectional view showing a distal end-side configuration of the illuminating unit shown in FIG. 22.
Figure 26:
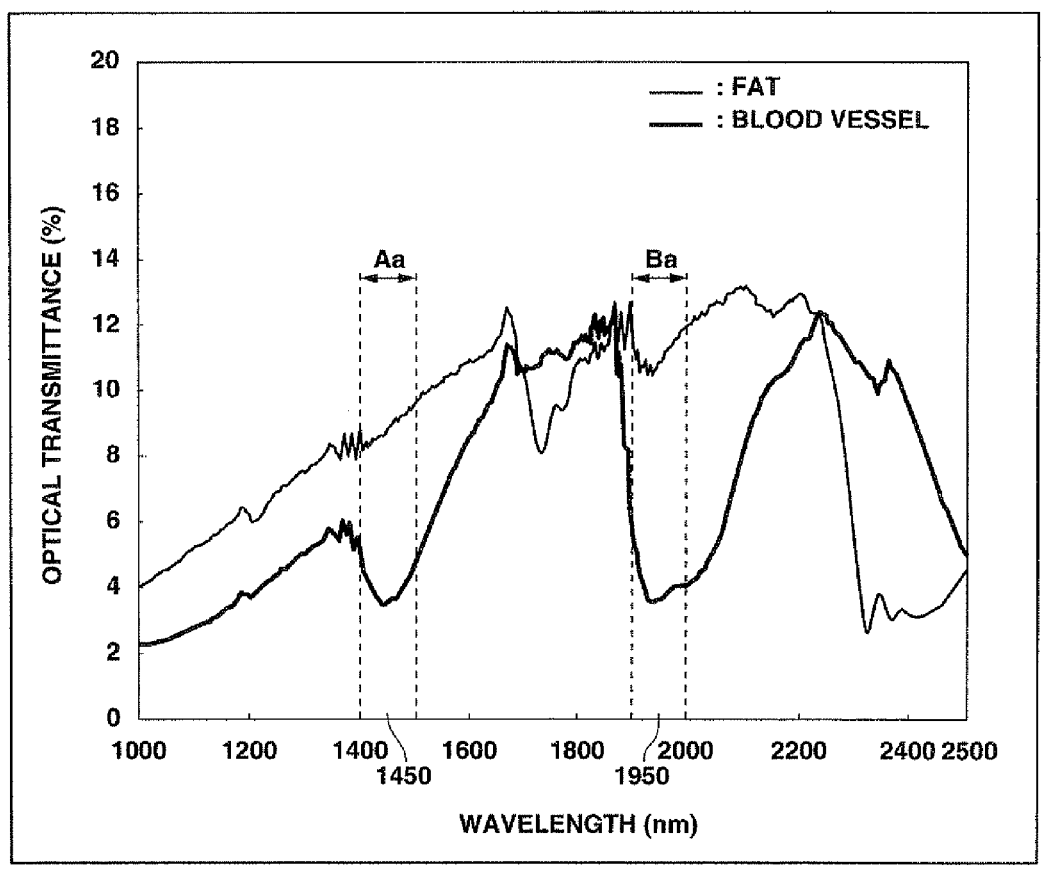
FIG. 26 is a diagram showing transmittance characteristics of blood vessels and fat in a living body tissue.
Figure 27:
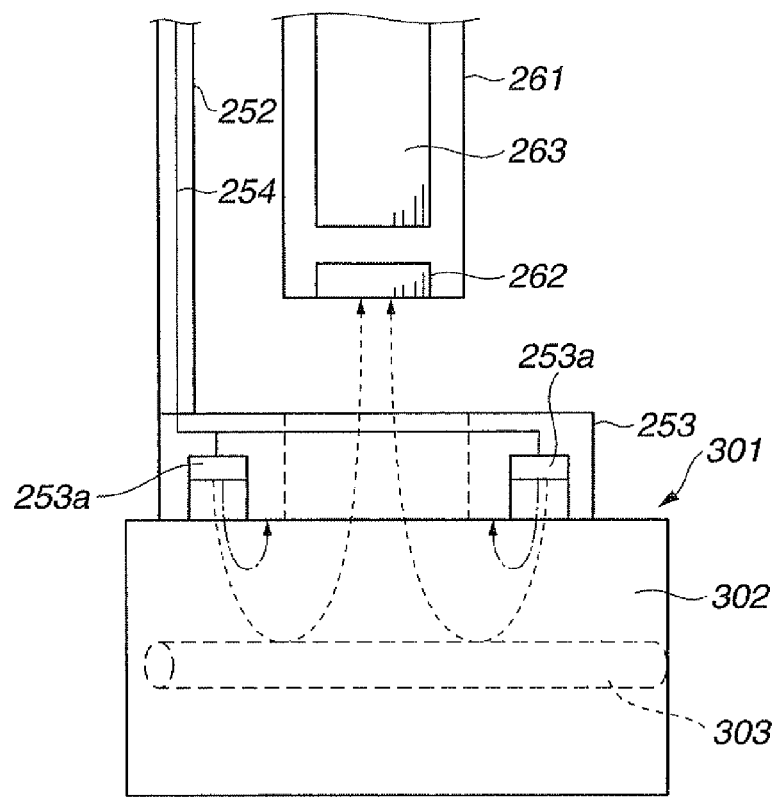
FIG. 27 is a schematic diagram showing optical paths of illuminating light and reflected light when a state of vascular flow is obtained using the image pickup system shown in FIG. 22.
Figure 28:
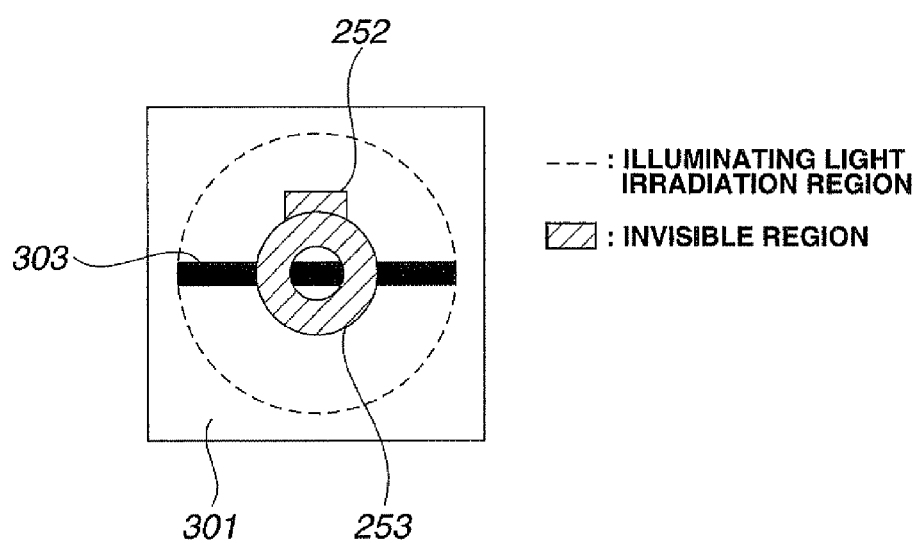
FIG. 28 is an example of a vascular image displayed on a monitor after image pickup is performed in the state shown in FIG. 27.
Figure 29:
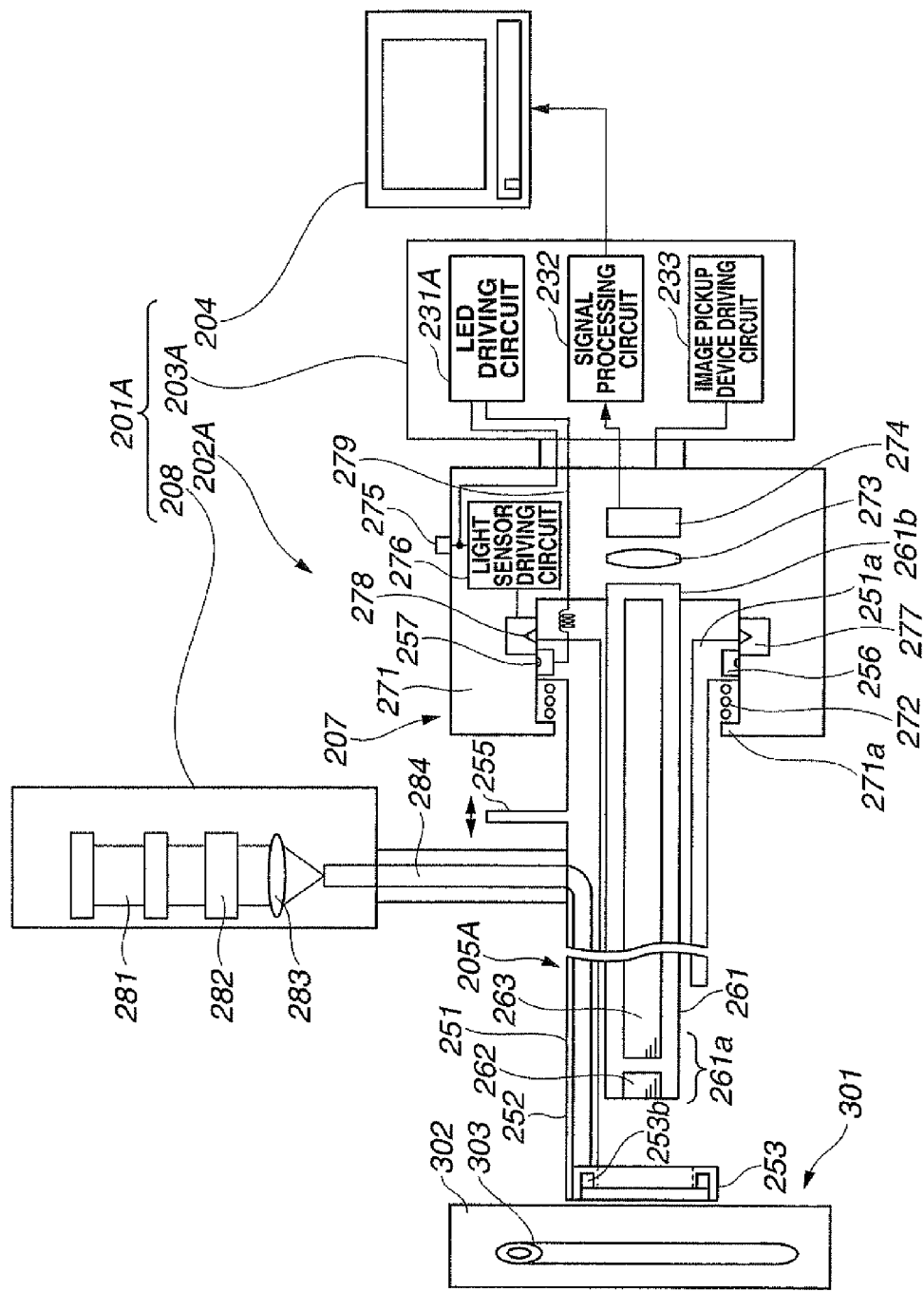
FIG. 29 is a diagram showing an example of a configuration of substantial portions of an image pickup system according to the seventh embodiment of the present invention which differs from the example shown in FIG. 22.
Figure 30:
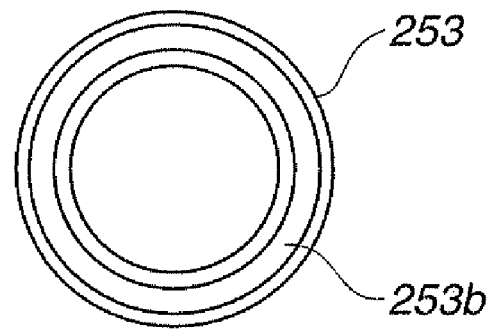
FIG. 30 is a front view showing a configuration of an illuminating portion provided at an illuminating unit shown in FIG. 29.
Figure 31:
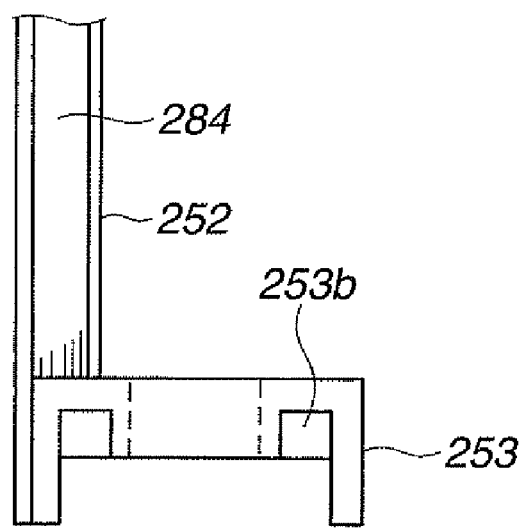
FIG. 31 is a cross sectional view showing a distal end-side configuration of the illuminating unit shown in FIG. 29.

FIGS. 22 to 31 relate to an embodiment of the present invention. FIG. 22 is a diagram showing an example of a configuration of substantial portions of an image pickup system according to a seventh embodiment of the present invention. FIG. 23 is a perspective view showing a distal end-side configuration of an illuminating unit and an endoscope main body shown in FIG. 22. FIG. 24 is a front view showing a configuration of an illuminating portion provided at the illuminating unit shown in FIG. 22. FIG. 25 is a cross sectional view showing a distal end-side configuration of the illuminating unit shown in FIG. 22. FIG. 26 is a diagram showing transmittance characteristics of blood vessels and fat in living body tissue. FIG. 27 is a schematic diagram showing optical paths of illuminating light and reflected light when a state of vascular flow is obtained using the image pickup system shown in FIG. 22. FIG. 28 is an example of a vascular image displayed on a monitor after image pickup is performed in the state shown in FIG. 27. FIG. 29 is a diagram showing an example of a configuration of substantial portions of an image pickup system according to the seventh embodiment of the present invention which differs from the example shown in FIG. 22. FIG. 30 is a front view showing a configuration of an illuminating portion provided at an illuminating unit shown in FIG. 29. FIG. 31 is a cross sectional view showing a distal end-side configuration of the illuminating unit shown in FIG. 29.

As shown in FIG. 22, an image pickup system 201 is configured so as to include, as substantial portions thereof: an endoscope 202 that picks up an image of a living body tissue 301 as a subject and outputs the pickup image of the living body tissue 301 as an image pickup signal; a camera control unit (hereinafter abbreviated as CCU) 203 that performs image processing on the image pickup signal outputted from the endoscope 202 and outputs the image pickup signal subjected to the image processing as a video signal; and a monitor 204 that image-displays an image of the living body tissue 301 based on the video signal outputted from the CCU 203.

In addition, the endoscope 202 is configured so as to include: an illuminating unit 205 that assumes either a driven state or a suspended state based on a drive signal outputted from the CCU 203 and in the driven state, irradiates illuminating light including at least a band in the infrared region to the living body tissue 301; an endoscope main body 206 that collects and transmits an image of the living body tissue 301 illuminated by the illuminating unit 205; and a camera head 207 that forms the image of the living body tissue 301 transmitted from the endoscope main body 206 and outputs the image as an image pickup signal.

As shown in FIG. 22, the illuminating unit 205 provided with functions as illuminating section includes: a cylindrical sliding portion 251 that fits onto an outer peripheral surface of a sheathing tube forming an insertion portion 261 of the endoscope main body 206 so as to be slidable; a supporting rod 252 extended from a distal end-side of the sliding portion 251; a toric illuminating portion 253 provided so as to be integrally fixed to the distal end-side of the supporting rod 252; and a signal line 254 provided inserted through the insides of the sliding portion 251 and the supporting rod 252 and which transmits a drive signal outputted from the CCU 203 to the illuminating portion 253.

More specifically, the sliding portion 251, the supporting rod 252 and the illuminating portion 253 are respectively configured as, for example, shown in FIG. 23. The sliding portion 251 is configured so as to be slidable in a direction of an optical axis Oa shown in FIG. 23 of an objective lens 262 provided at the endoscope main body 206. In addition, an inner diameter of a toric portion of the illuminating portion 253 is configured so as to be larger than an outer diameter of a distal end portion 261a of the insertion portion 261. As a result, a distal end part of the insertion portion 261 can be inserted through the inside of the toric portion of the illuminating portion 253.

As shown in FIG. 22, the illuminating portion 253 assumes either a driven state or a suspended state based on a drive signal outputted from the CCU 203 via the signal line 254. In addition, the illuminating portion 253 is configured so as to include, for example, as shown in FIG. 24, a plurality of LEDs 253a that respectively irradiates, in the driven state, illuminating light including at least a wavelength band exceeding a wavelength of 1200 nm as a predetermined wavelength band. Furthermore, the signal line 254 is respectively connected to the LEDs 253a.

Incidentally, the predetermined wavelength band included in the illuminating light respectively irradiated by the LEDs 253a is a wavelength band at which a difference between the optical transmittance of fat and the optical transmittance of blood vessels (walls of the blood vessels) in the living body tissue 301 becomes maximum. More specifically, the predetermined wavelength band is either one of, for example, a wavelength band of 1450 nm±50 nm indicated by the reference character Aa in FIG. 26 or a wavelength band of 1950 nm±50 nm indicated by the reference character Ba in FIG. 26. In other words, the predetermined wavelength band is a wavelength band including a wavelength at which the difference between the optical transmittance of fat and the optical transmittance of blood vessels (walls of the blood vessels) becomes maximum.

In addition, the LEDs 253a of the illuminating portion 253 are capable of illuminating the living body tissue 301 by illuminating light and are respectively disposed at, for example, positions shown in FIG. 25 such that the LEDs 253a do not come into direct contact with the living body tissue 301 when the illuminating portion 253 is brought into close contact with the living body tissue 301. Therefore, when performing an observation using the image pickup system 201, a user can obtain a state of vascular flow of a living body tissue existing in a desired observation site in a state where thermal damage to the living body tissue is suppressed.

Furthermore, as shown in FIG. 22, a rear end portion 251a of the sliding portion 251 is disposed on, for example, an inner side of a cylindrical portion 271 of the camera head 207. A coil spring 272 is disposed in a space sandwiched between the rear end portion 251a of the sliding portion 251 and an inner peripheral face of the cylindrical portion 271. In addition, the illuminating unit 205 is arranged to be biased towards a posterior side of the insertion portion 261 by the coil spring 272. Moreover, retaining protrusions are formed at a front end portion 271a of the cylindrical portion 271 and the rear end portion 251a of the sliding portion 251 to which both ends of the coil spring 272 abut.

Furthermore, a slide lever 255 for slide-operating the sliding portion 251 is provided on a rear end-side of the sliding portion 251. According to such a configuration, for example, when the slide lever 255 is operated in a direction indicated by the arrow in FIG. 22, the illuminating unit 205 slidingly moves towards an axial direction side of the insertion portion 261.

Incidentally, the coil spring 272 extends towards the posterior side of the insertion portion 261 in a state where the slide lever 255 is not operated. The aforementioned slide lever 255 of the illuminating unit 205 is configured so as to abut the front end portion 271a of the camera head 207 in a state where the coil spring 272 extends towards the posterior side of the insertion portion 261. Furthermore, the aforementioned illuminating portion 253 of the illuminating unit 205 is configured such that a light output side-end face is disposed on approximately the same plane as a light incident face of the objective lens 262 in the state where the coil spring 272 extends towards the posterior side of the insertion portion 261.

In addition, as shown in FIG. 22, the illuminating unit 205 includes: a toric magnetic metal 256 provided at a protrusion of the rear end portion 251a and which is formed by iron, nickel, or the like; and a toric LED 257 provided on an outer surface of the magnetic metal 256 and which is driven based on a drive signal outputted from the CCU 203.

The magnetic metal 256 provided with functions as positioning section is provided in a state where a portion of an outer surface thereof including at least the LED 257 is exposed on an inner peripheral surface-side of the cylindrical portion 271 of the camera head 207 at the protrusion provided on the rear end portion 251a. In addition, the magnetic metal 256 and the LED 257 are slid while remaining in close contact with the inner peripheral face of the cylindrical portion 271 according to a sliding state of the illuminating unit 205 (or the sliding portion 251).

The endoscope main body 206 is configured so as to include: a hard insertion portion 261 configured in a shape and size allowing insertion into a body cavity; an objective lens 262 disposed on a distal end-side inside the insertion portion 261 and which collects and forms an image of the living body tissue 301; and an image guide 263 whose distal end face is disposed at an image-forming position of the objective lens 262 and whose rear end face is disposed on a rear end-side inside the insertion portion 261. According to such a configuration, an image of the living body tissue 301 collected by the objective lens 262 is first formed on a distal end face of the image guide 263 and then transmitted to a rear end face of the image guide 263 disposed on the rear end-side inside the insertion portion 261. In addition, the insertion portion 261 is configured such that the camera head 207 is detachable at a rear end portion 261b of the endoscope main body. By mounting the insertion portion 261 onto the camera head 207, positions of the respective portions of the endoscope main body 206 with respect to the position of an image pickup device 274 of the camera head 207 become fixed.

The camera head 207 is configured so as to include: an image-forming lens 273 disposed at a position opposing the rear end face of the image guide 263; and an image pickup device 274 that picks up an image of the living body tissue 301 formed by the image-forming lens 273 and outputs the image as an image pickup signal.

The image pickup device 274 as image pickup section is formed by a semiconductor detecting element (photovoltaic semiconductor detecting element) such as Ex-InGaAs, InAs, or InSb which is sensitive in an infrared region exceeding at least a wavelength of 1200 nm.

Incidentally, the camera head 207 is not limited to an arrangement including only the image pickup device 274 capable of detecting light in the infrared region and may also include a CCD (charge coupled device) capable of detecting light in the visible region in addition to the image pickup device 274.

In addition, the camera head 207 includes: an optical sensor switch 275 that assumes either an enabled state or a disabled state according to a user operation; an optical sensor drive circuit 276 that detects whether the optical sensor switch 275 is in the enabled state or the disabled state and outputs an optical sensor drive signal when the optical sensor switch 275 is in the enabled state; a toric electromagnet 277 provided on the cylindrical portion 271; and a toric optical sensor 278 provided on an outer surface of the electromagnet 277 and which is driven based on an optical sensor drive signal outputted from the optical sensor drive circuit 276.

The electromagnet 277 having functions as positioning section is provided in a state where a portion of the outer surface including at least the optical sensor 278 is exposed towards a rear end portion 251a side of the cylindrical portion 271.

Based on an optical sensor drive signal outputted from the optical sensor drive circuit 276, the optical sensor 278 assumes a driven state when the optical sensor drive signal is outputted and assumes a suspended state when the optical sensor drive signal is not outputted. Furthermore, when light is detected in the driven state, the optical sensor 278 outputs a current in accordance with the detected light to the electromagnet 277. According to the aforementioned configuration of the optical sensor 278, the electromagnet 277 generates a magnetic force corresponding to a current outputted from the optical sensor 278.

Incidentally, the LED 257 of the illuminating unit 205 is disposed at a protrusion provided on the rear end portion 251a in a pre-positioned state so that, when the illuminating unit 205 is slid to an optimal position corresponding to focal positions of the endoscope main body 206 and the camera head 207, approximately the entire LED 257 enters an optical detection range of the optical sensor 278 of the camera head 207. More specifically, the LED 257 of the illuminating unit 205 is disposed so that, for example, when the distance between the light output side-end face of the illuminating portion 253 and the light incident face of the objective lens 262 becomes 30 mm, approximately the entire LED 257 enters then optical detection range of the optical sensor 278 of the camera head 207.

The CCU 203 is configured to include: an LED drive circuit 231; a signal processing circuit 232; and an image pickup device drive circuit 233 that supplies power for driving the image pickup device 274 of the camera head 207.

The LED drive circuit 231 outputs via the signal line 254 inside the sliding portion 251a drive signal that causes each of the LEDs 253a of the illuminating portion 253 to assume either a driven state or a suspended state. In addition, the LED drive circuit 231 detects whether the optical sensor switch 275 is in an enabled state or a disabled state, and when the optical sensor switch 275 is in the enabled state, outputs via the signal line 254 a drive signal for driving the LED 257 provided at the illuminating unit 205.

The signal processing circuit 232 performs image processing on an image pickup signal outputted from the image pickup device 274 of the camera head 207, and outputs the image pickup signal subjected to the image processing as a video signal.

Next, operations of the image pickup system 201 will be described.

First, in a state where the camera head 207 is mounted onto the insertion portion 261, in order to obtain a state of vascular flow in the living body tissue 301 of a desired observation site, a user operates the slide lever 255 and slides the sliding portion 251 of the illuminating unit 205 in order to bring a light output-side end face on the of the illuminating portion 253 into close contact with the living body tissue 301. By performing such an operation, the user places the illuminating portion 253 and the objective lens 262 of the endoscope main body 206 at, for example, positions such as shown in FIG. 27 with respect to a surface of the living body tissue 301.

Subsequently, the user operates the optical sensor switch 275 and changes the optical sensor switch 275 to the enabled state so that the surface of the living body tissue 301 which is in a state of close contact with the light output-side end face of the illuminating portion 253 and the light incident face of the objective lens 262 are respectively continuously disposed at optimal positions corresponding to the focal positions of the endoscope main body 206 and the camera head 207.

Due to the optical sensor switch 275 assuming the enabled state, an optical sensor drive signal is outputted from the optical sensor drive circuit 276. Then, based on the optical sensor drive signal, the optical sensor 278 assumes a driven state. In addition, upon detecting that the optical sensor switch 275 is in the enabled state, the LED drive circuit 231 outputs a drive signal for driving the LED 257.

Subsequently, due to the sliding of the sliding portion 251 by the user, as a light emitted by the LED 257 enters an optical detection range of the optical sensor 278, the optical sensor 278 outputs a current corresponding to the light emitted by the LED 257 to the electromagnet 277.

Then, the electromagnet 277 generates a magnetic force corresponding to the current outputted from the optical sensor 278 and attracts the magnetic metal 256 by the magnetic force. Consequently, the position of the illuminating unit 205 with respect to the position of the endoscope main body 206 becomes fixed, and as a result, the surface of the living body tissue 301 in a state of close contact with the light output-side end face of the illuminating portion 253 and the light incident face of the objective lens 262 are respectively continuously disposed at optimal positions corresponding to the focal positions of the endoscope main body 206 and the camera head 207. In addition, since the insertion portion 261 is mounted onto the camera head 207, the position of the image pickup device 274 with respect to the position of the objective lens 262 becomes fixed. In other words, in the case where the magnetic metal 256 is attracted by the magnetic force generated by the electromagnet 277 and the insertion portion 261 is mounted onto the camera head 207, the distance between the light output-side end face of the illuminating portion 253 and an image pickup face of the image pickup device 274 is maintained at a predetermined distance corresponding to the focal distances of the endoscope main body 206 and the camera head 207.

In addition, when the LED 253a is in a driven state, an illuminating light having a wavelength band of 1450 nm±50 nm or an illuminating light having a wavelength band of 1950 nm±50 nm as an illuminating light having a predetermined wavelength band at least exceeding a wavelength of 1200 mm is irradiated to the inside of the living body tissue 301.

Furthermore, a portion of light among the illuminating light irradiated from the LED 253a is reflected by fat 302 existing inside the living body tissue 301 near the surface of the same and becomes reflected light having, for example, an optical path indicated by the dashed-dotted line shown in FIG. 27. In addition, another portion of light among the illuminating light irradiated from the LED 253a that is not reflected by the fat 302 is reflected by blood vessels 303 of which at least a portion is covered by fat 302 and which exist at a deep portion inside the living body tissue 301, and becomes reflected light having, for example, an optical path indicated by the dotted line shown in FIG. 27.

Consequently, reflected light that is reflected by fat 302 existing inside the living body tissue 301 near the surface of the same and which has, for example, the optical path indicated by the dashed-dotted line shown in FIG. 27 is shielded by the toric portion of the illuminating portion 253 having functions of reflected light suppressing section and is therefore not collected by the objective lens 262. In addition, reflected light that is reflected by blood vessels 303 existing at a deep portion inside the living body tissue 301 and which has, for example, the optical path indicated by the dotted line shown in FIG. 27 is not shielded by the toric portion of the illuminating portion 253 having functions of reflected light suppressing section and passes an inner side of the toric portion to be collected by the objective lens 262.

An image of the living body tissue 301 including an image of the blood vessels 303 which is included in reflected light collected by the objective lens 262 is transmitted by the image guide 263, then formed by the image-forming lens 273, and after picked up by the image pickup device 274, outputted as an image pickup signal to the CCU 203.

The signal processing circuit 232 performs image processing on an image pickup signal outputted from the image pickup device 274 of the camera head 207, and outputs the image pickup signal subjected to the image processing as a video signal.

Consequently, for example, an image of the living body tissue 301 including an image of the blood vessels 303 such as shown in FIG. 28 is image-displayed on the monitor 204. More specifically, among images of the living body tissue 301, an image such as the image shown in FIG. 28 in which an image of the blood vessels 303 existing within an irradiating range of the illuminating light from the LED 253a is visualized at a higher contrast than images of the periphery of the blood vessels is displayed on the monitor 204.

Incidentally, the shaded area in FIG. 28 represents, for example, an image of the toric portions of the supporting rod 252 and the illuminating portion 253 as an invisible region in the image of the living body tissue 301 image-displayed on the monitor 204. In a state where the slide lever 255 is not operated and the coil spring 272 extends towards the posterior side of the insertion portion 261, the light output side-end face is disposed on approximately the same plane as the light incident face of the objective lens 262. Therefore, the user is also able to observe an image of the blood vessels 303 in a state where an image of the toric portions of the supporting rod 252 and the illuminating portion 253 such as described above is not image-displayed on the monitor 204.

In addition, as long as the aforementioned electromagnet 277 is disposed in the cylindrical portion 271 in a state where a portion of the external surface including at least the optical sensor 278 is exposed to the rear end portion 251a side, the electromagnet 277 may be provided with a configuration in which, for example, the electromagnet 277 is slidable towards an axial direction-side of the insertion portion 261 in conjunction with the optical sensor 278. Furthermore, when the electromagnet 277 is provided with a configuration in which the electromagnet 277 is slidable towards an axial direction-side of the insertion portion 261, the user is able to dispose and fix the position of the illuminating unit 205 with respect to the position of the endoscope main body 206 at a desired position in accordance with the movable range of the electromagnet 277.

Moreover, the image pickup system 201 according to the seventh embodiment is not limited to an image pickup system provided with a configuration in which illuminating light is irradiated from the LED 253a to the living body tissue 301, and may also be configured as an image pickup system 201A shown in FIG. 29 provided with a configuration in which, for example, illuminating light is irradiated from a lamp inside a light source apparatus to the living body tissue 301.

As shown in FIG. 29, the image pickup system 201A is configured to include: an endoscope 202A; a CCU 203A having an LED drive circuit 231A in place of the LED drive circuit 231 of the CCU 203; a monitor 204 provided with the configuration described above; and a light source apparatus 208.

In addition, the endoscope 202A is configured to include: an illuminating unit 205A that transmits illuminating light irradiated from the light source apparatus 208 and which irradiates the illuminating light to the living body tissue 301; an endoscope main body 206 having the configuration described above; and a camera head 207 having the configuration described above.

The illuminating unit 205A having a portion of functions as illuminating section is provided with a configuration in which the signal line 254 is removed from the configuration described above, and a light guide 284 is provided so as to be inserted through the inside of the sliding portion 251 and the supporting rod 252 of the illuminating unit 205A.

Furthermore, at the illuminating portion 253 of the illuminating unit 205A, a light guide 253b that irradiates illuminating light transmitted from the light guide 284 is provided in place of the LED 253a. The light guide 253b is formed with, for example, a shape conforming to the toric shape of the illuminating portion 253 as shown in FIG. 30.

The illuminating portion 253 of the illuminating unit 205A is, for example, as shown in FIG. 31, provided so as to be integrally fixed to a distal end-side of the supporting rod 252. In addition, the light guide 253b of the illuminating portion 253 is provided so as to be integrally fusion-bonded to a distal end-side end face of the light guide 284.

The light source apparatus 208 provided with a portion of functions as illuminating section is configured to include: a lamp 281 that irradiates light of a wavelength band of at least 1200 nm or more and which is configured by, for example, a halogen lamp or the like; a bandpass filter 282 inserted on an optical path of the light irradiated from the lamp 281; and a collecting lens 283 that collects light having passed through the bandpass filter 282 and supplies the light as illuminating light having a predetermined wavelength band for illuminating the living body tissue 301.

Moreover, the bandpass filter 282 as spectroscopic section is provided with a configuration in which among light irradiated from the lamp 281, for example, only light of either one of a wavelength band of 1450 nm±50 nm indicated by the reference character Aa in FIG. 26 or a wavelength band of 1950 nm±50 nm indicated by the reference character Ba in FIG. 26 is passed through as the predetermined wavelength band. Incidentally, the position at which the bandpass filter 282 is disposed is not limited to on the optical path of light irradiated from the lamp 281 and, for example, may be disposed between the image-forming lens 273 and the image pickup device 274 inside the camera head 207.

Furthermore, a proximal end-side end face of the light guide 284 provided with a configuration so as to be detachable with respect to the light source apparatus 208 is disposed in the image-forming position of the collecting lens 283. In addition, according to the configurations of the illuminating unit 205A, the light source apparatus 208 and the light guide 284 described above, illuminating light having a predetermined wavelength band and which is supplied to the proximal end-side end face of the light guide 284 is irradiated from a light guide 253b integrally provided on the distal end-side end face of the light guide 284 to the living body tissue 301.

The LED drive circuit 231A detects whether the optical sensor switch 275 is in an enabled state or a disabled state, and when the optical sensor switch 275 is in the enabled state, outputs via a signal line 279 a drive signal for driving the LED 257 provided at the illuminating unit 205.

Incidentally, operations of the image pickup system 201A provided with the configuration described above is approximately similar to the operations of the aforementioned image pickup system 201. As such, a detailed description on the operations of the image pickup system 201A shall be hereby omitted.

As described above, the image pickup system 201 according to the seventh embodiment is capable of obtaining a state of vascular flow of blood vessels covered by fat and which exist in a living body tissue of a desired observation site without having to perform operations such as removal of fat surrounding the blood vessels. In addition, by having the configuration described above, the image pickup system 201 according to the seventh embodiment is capable of modifying an arrangement state of illuminating section for irradiating illuminating light and image pickup section for picking up an image of blood vessels illuminated by the illuminating light to an arrangement state optimal for obtaining a vascular image even without a user performing case-by-case adjustments.

As a result, compared to conventional arrangements, the image pickup system 201 according to the seventh embodiment is capable of reducing the time period required for performing treatment on living body tissue. It should be noted that the effects achieved by the image pickup system 201 described above can be similarly achieved by the image pickup system 201A.

(Eighth Embodiment)

Figure 32:
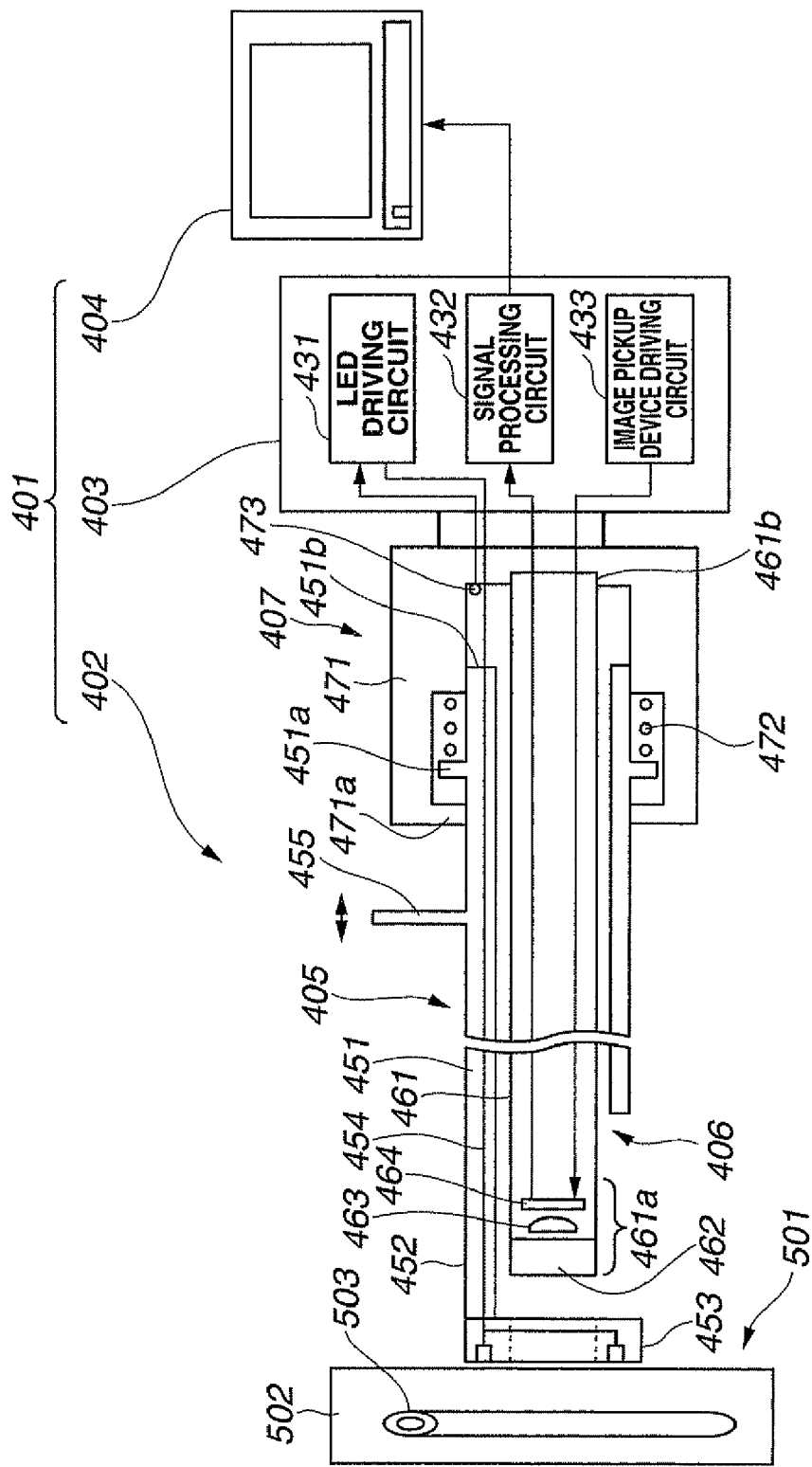
FIG. 32 is a diagram showing an example of a configuration of substantial portions of an image pickup system according to an eighth embodiment of the present invention.

FIGS. 32 to 44 relate to an eighth embodiment of the present invention. FIG. 32 is a diagram showing an example of a configuration of substantial portions of an image pickup system according to the eighth embodiment of the present invention.

Figure 33:
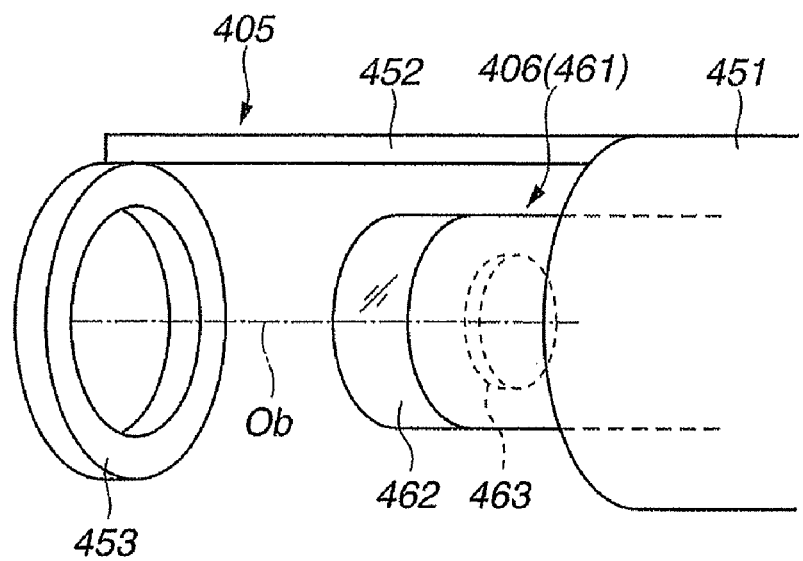
FIG. 33 is a perspective view showing a distal end-side configuration of an illuminating unit and an endoscope main body shown in FIG. 32.
Figure 34:
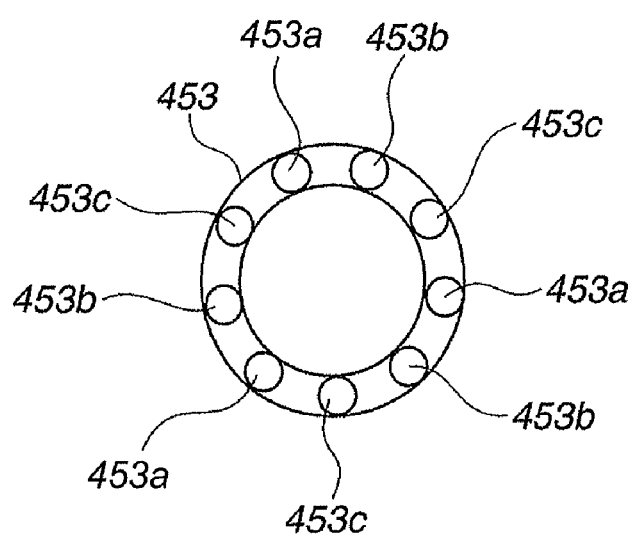
FIG. 34 is a front view showing a configuration of an illuminating portion provided at the illuminating unit shown in FIG. 32.
Figure 35:
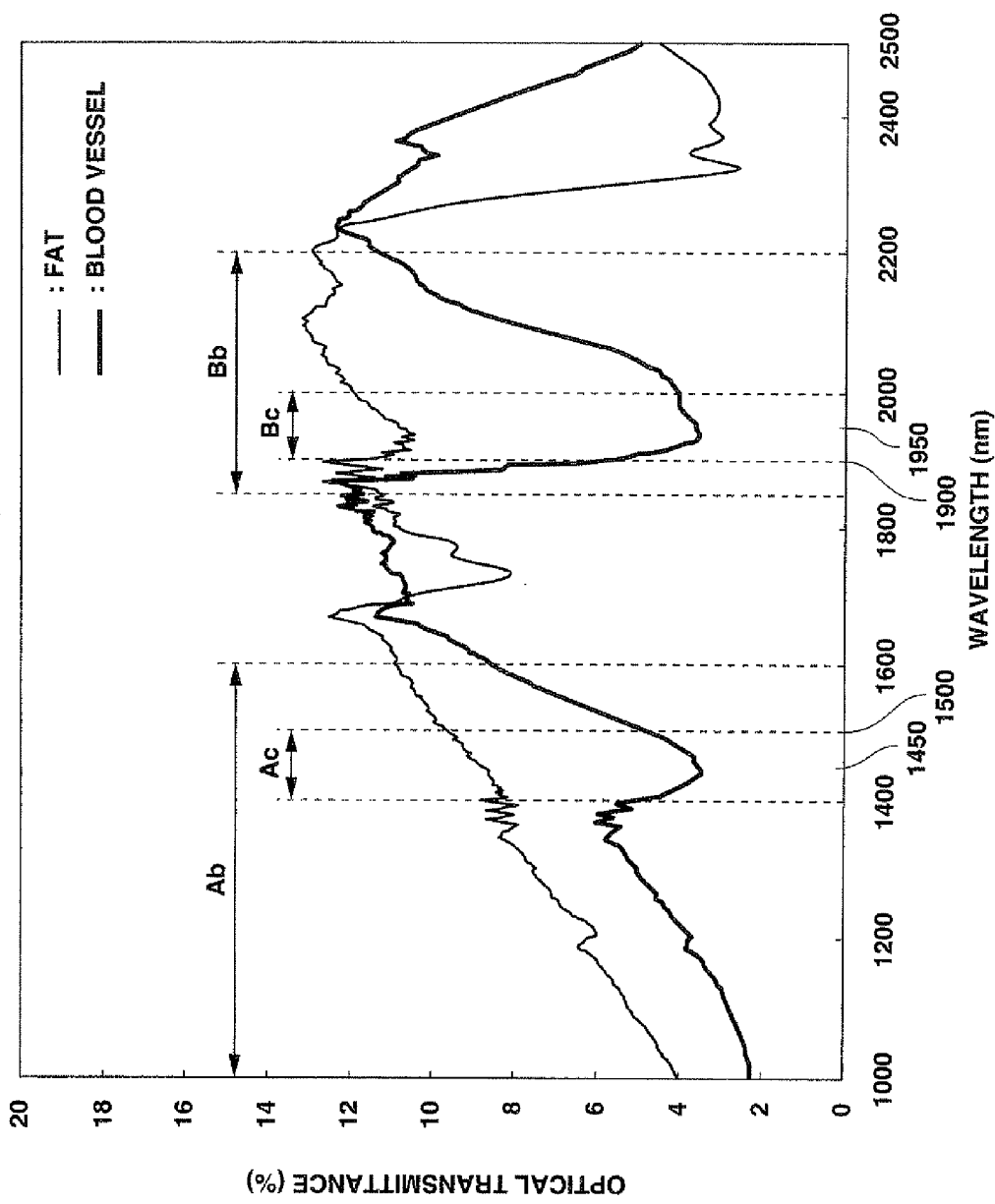
FIG. 35 is a diagram showing transmittance characteristics of blood vessels and fat in a living body tissue.
Figure 36:
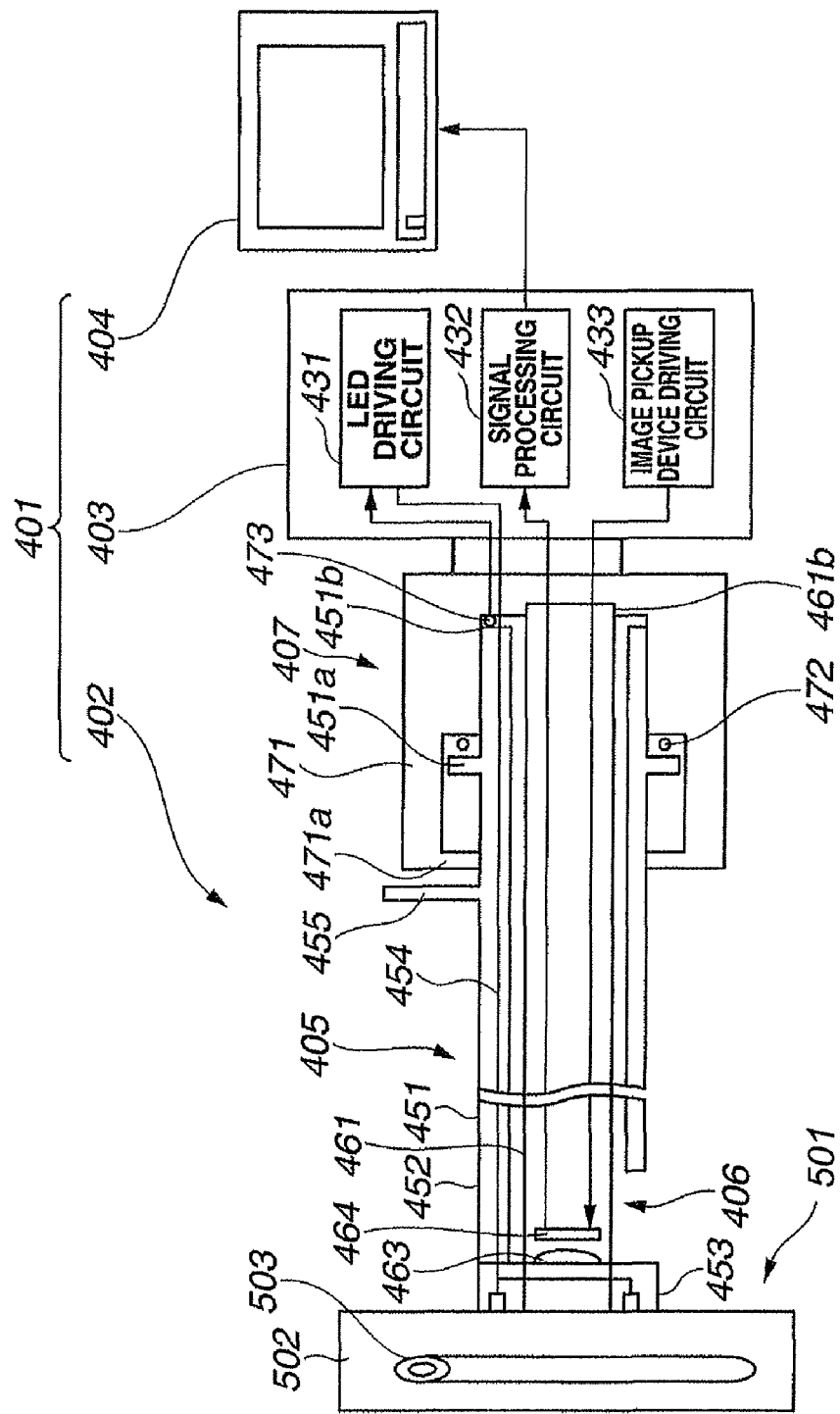
FIG. 36 is a diagram showing an example of a case where a slide detection switch is in an enabled state in the image pickup system shown in FIG. 32.
Figure 37:
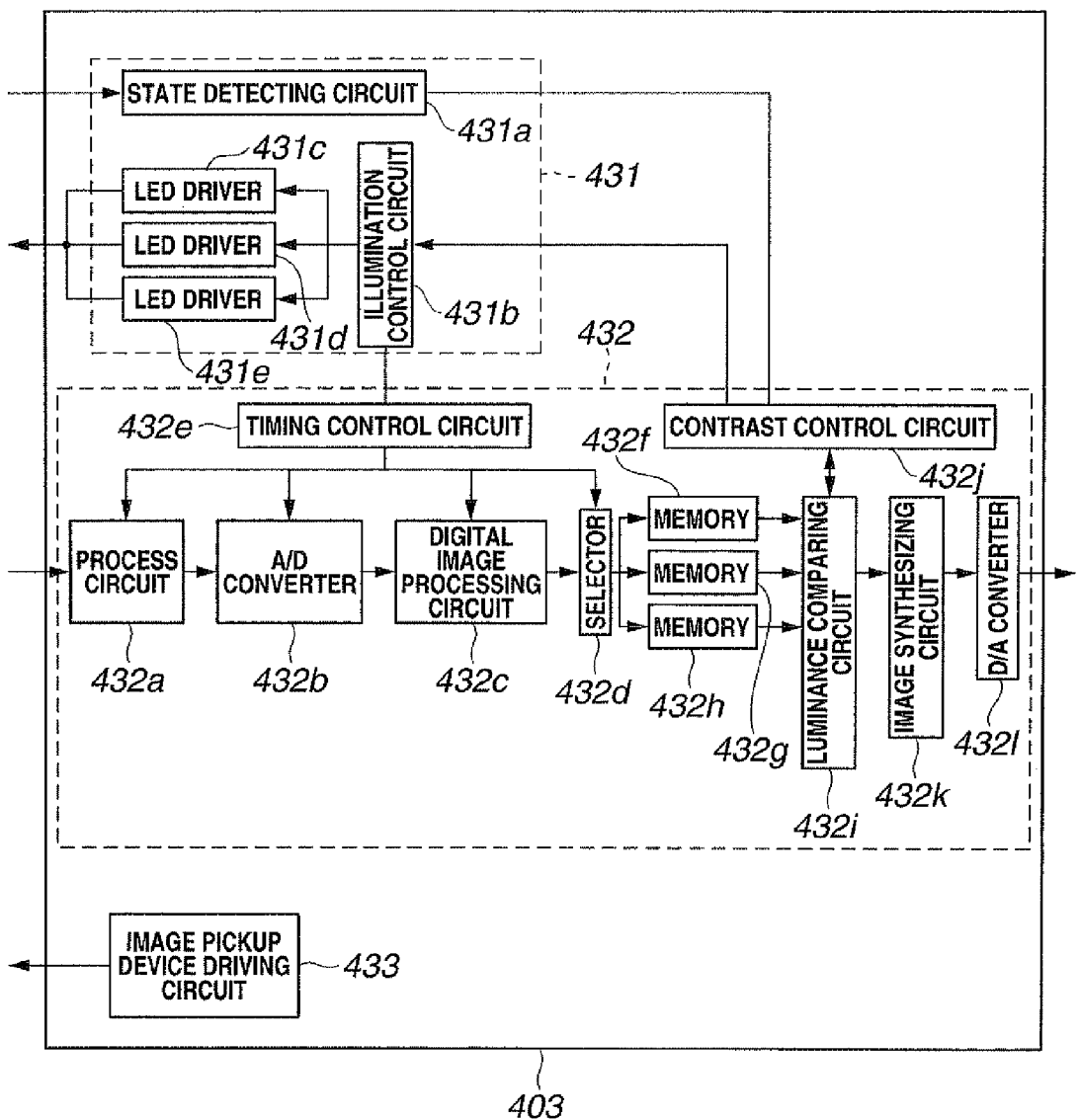
FIG. 37 is a block diagram showing an internal configuration of a CCU in the image pickup system shown in FIG. 32.
Figure 38:
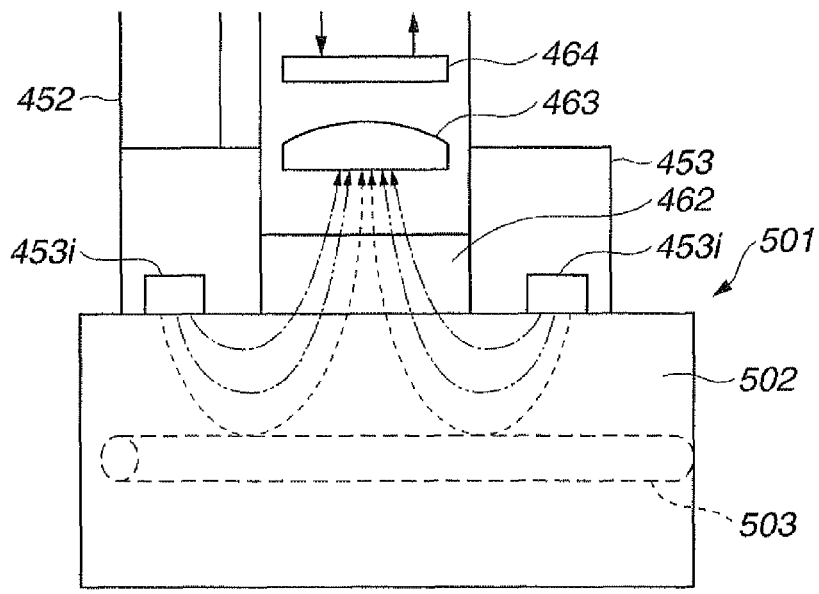
FIG. 38 is a schematic diagram showing optical paths of illuminating light and reflected light when a state of vascular flow is obtained using the image pickup system shown in FIG. 32.
Figure 39:
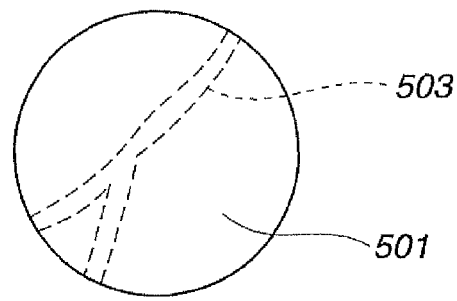
FIG. 39 is a schematic diagram showing an image of a living body tissue and blood vessels illuminated by a first illuminating light when a state of vascular flow is obtained using the image pickup system shown in FIG. 32.
Figure 40:
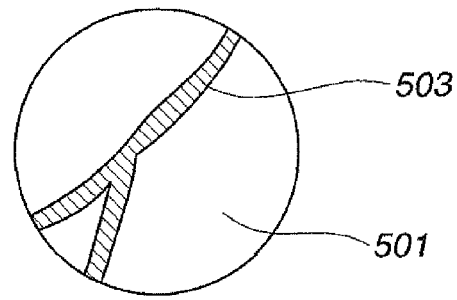
FIG. 40 is a schematic diagram showing an image of a living body tissue and blood vessels illuminated by a second illuminating light when a state of vascular flow is obtained using the image pickup system shown in FIG. 32.
Figure 41:
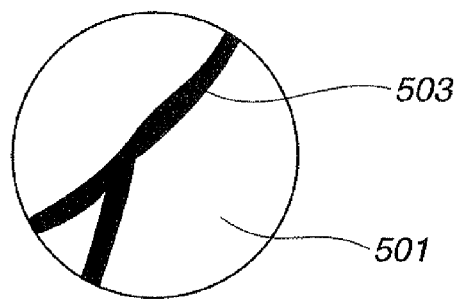
FIG. 41 is a schematic diagram showing an image of a living body tissue and blood vessels illuminated by a third illuminating light when a state of vascular flow is obtained using the image pickup system shown in FIG. 32.
Figure 42:
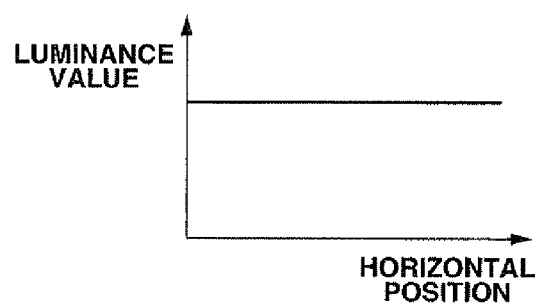
FIG. 42 is a diagram showing an example of a luminance value detection result regarding the image of the living body tissue and blood vessels shown in FIG. 39.
Figure 43:
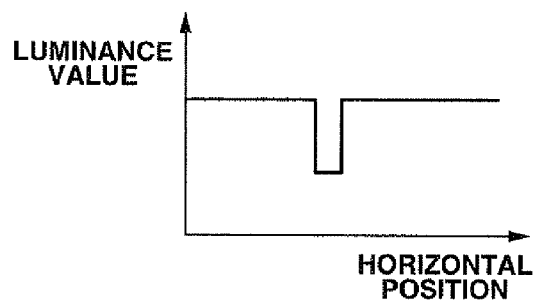
FIG. 43 is a diagram showing an example of a luminance value detection result regarding the image of the living body tissue and blood vessels shown in FIG. 40.
Figure 44:
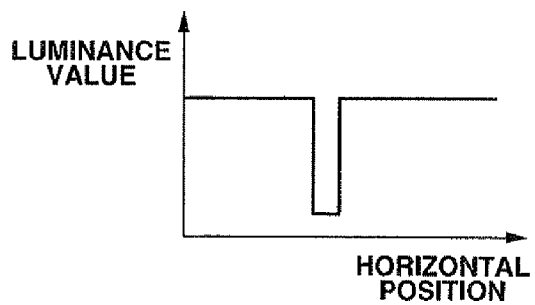
FIG. 44 is a diagram showing an example of a luminance value detection result regarding the image of the living body tissue and blood vessels shown in FIG. 41.

FIG. 33 is a perspective view showing a distal end-side configuration of an illuminating unit and an endoscope main body shown in FIG. 32. FIG. 34 is a front view showing a configuration of an illuminating portion provided at the illuminating unit shown in FIG. 32. FIG. 35 is a diagram showing transmittance characteristics of blood vessels and fat in a living body tissue. FIG. 36 is a diagram showing an example of a case where a slide detection switch is in an enabled state in the image pickup system shown in FIG. 32. FIG. 37 is a block diagram showing an internal configuration of a camera control unit (hereinafter referred to as CCU) in the image pickup system shown in FIG. 32. FIG. 38 is a schematic diagram showing optical paths of illuminating light and reflected light when a state of vascular flow is obtained using the image pickup system shown in FIG. 32. FIG. 39 is a schematic diagram showing an image of a living body tissue and blood vessels illuminated by a first illuminating light when a state of vascular flow is obtained using the image pickup system shown in FIG. 32. FIG. 40 is a schematic diagram showing an image of a living body tissue and blood vessels illuminated by a second illuminating light when a state of vascular flow is obtained using the image pickup system shown in FIG. 32. FIG. 41 is a schematic diagram showing an image of a living body tissue and blood vessels illuminated by a third illuminating light when a state of vascular flow is obtained using the image pickup system shown in FIG. 32. FIG. 42 is a diagram showing an example of a luminance value detection result regarding the image of the living body tissue and blood vessels shown in FIG. 39. FIG. 43 is a diagram showing an example of a luminance value detection result regarding the image of the living body tissue and blood vessels shown in FIG. 40. FIG. 44 is a diagram showing an example of a luminance value detection result regarding the image of the living body tissue and blood vessels shown in FIG. 41.

As shown in FIG. 32, an image pickup system 401 is configured so as to include, as substantial portions thereof: an endoscope 402 that picks up an image of a living body tissue 501 as a subject and outputs the pickup image of the living body tissue 501 as an image pickup signal; a CCU 403 that performs image processing on the image pickup signal outputted from the endoscope 402 and outputs the image pickup signal subjected to the image processing as a video signal; and a monitor 404 that image-displays an image of the living body tissue 501 based on an analog video signal outputted from the CCU 403.

In addition, the endoscope 402 is configured so as to include: an illuminating unit 405 that is driven based on a drive signal outputted from the CCU 403 and which irradiates illuminating light including at least a band in the infrared region to the living body tissue 501; an endoscope main body 406 that forms and picks up an image of the living body tissue 501 illuminated by the illuminating unit 405 and which outputs the image as an image pickup signal; and an adapter 407 that enables attaching and detaching of the endoscope main body 406.

As shown in FIG. 32, the illuminating unit 405 provided with functions as illuminating section includes: a cylindrical sliding portion 451 that fits onto an outer peripheral surface of a sheathing tube forming an insertion portion 461 of the endoscope main body 406 so as to be slidable; a supporting rod 452 extended from a distal end-side of the sliding portion 451; a toric illuminating portion 453 provided so as to be integrally fixed to the distal end-side of the supporting rod 452; and a signal line 454 provided inserted through the insides of the sliding portion 451 and the supporting rod 452 and which transmits a drive signal outputted from the CCU 403 to the illuminating portion 453.

More specifically, the sliding portion 451, the supporting rod 452 and the illuminating portion 453 are respectively configured as, for example, shown in FIG. 33. The sliding portion 451 is configured so as to be slidable in a direction of an optical axis Ob shown in FIG. 33 of an objective lens 463 provided at the endoscope main body 406. In addition, an inner diameter of a toric portion of the illuminating portion 453 is configured so as to be larger than an outer diameter of a distal end portion 461a of the insertion portion 461. As a result, a distal end portion 461a of the insertion portion 461 can be inserted through the inside of the toric portion of the illuminating portion 453.

As shown in FIG. 32, the illuminating portion 453 assumes either a driven state or a suspended state based on a drive signal outputted from the CCU 403 via the signal line 454. In addition, the illuminating portion 453 is configured so as to include, for example, as shown in FIG. 34, LEDs 453a, 453b and 453c that respectively irradiate, in the driven state, illuminating light including at least a wavelength band exceeding a wavelength of 1000 nm as a predetermined wavelength band. Incidentally, in the eighth embodiment, as shown in FIG. 34, the illuminating portion 453 is assumed as having three each of the LEDs 453a, 453b and 453c.

The LEDs 453a, 453b and 453c respectively irradiate illuminating lights having different wavelength bands which at least include a wavelength in which the optical transmittance of fat becomes greater than the optical transmittance of blood vessels. More specifically, a first illuminating light irradiated from the LED 453a, a second illuminating light irradiated from the LED 453b, and a third illuminating light irradiated from the LED 453c respectively include, for example, at least any one of the respective wavelengths included in a wavelength band indicated by the reference character Ab shown in FIG. 35 and which range from 1000 nm to 1600 nm or the respective wavelengths included in a wavelength band indicated by the reference character Bb shown in FIG. 35 and which range from 150 nm to 2200 nm, and respectively have wavelength bands that differ from each other. Incidentally, in the eighth embodiment, if λ1 denotes a central wavelength of a wavelength band of the first illuminating light, λ2 denotes a central wavelength of a wavelength band of the second illuminating light, and λ3 denotes a central wavelength of a wavelength band of the third illuminating light, it is assumed that a relationship expressed as λ1<λ2<λ3 exists.

Furthermore, as shown in FIG. 32, a protrusion 451a of the sliding portion 451 is disposed on, for example, an inner side of a cylindrical portion 471 of the adapter 407. A coil spring 472 is disposed in a space sandwiched between the protrusion 451a of the sliding portion 451 and an inner peripheral face of the cylindrical portion 471. In addition, the illuminating unit 405 is arranged to be biased towards an anterior side of the insertion portion 461 by the coil spring 472. Moreover, retaining protrusions are formed so as to engage with the protrusion 451a of the sliding portion 451 at a front end portion 471a of the cylindrical portion 471 to which both ends of the coil spring 472 abut.

Furthermore, a slide lever 455 for slide-operating the sliding portion 451 is provided on a rear end-side of the sliding portion 451. According to such a configuration, for example, when the slide lever 455 is operated in a direction indicated by the arrow in FIG. 32, the illuminating unit 405 slidingly moves towards an axial direction side of the insertion portion 461.

In addition, the adapter 407 includes a slide detection switch 473 for detecting a sliding state of the sliding portion 451.

The slide detection switch 473 is disposed on an inner side of the cylindrical portion 471 of the adapter 407 and, as shown in FIG. 32, assumes a disabled state when not pressed by the rear end portion 451b of the sliding portion 451, and, as shown in FIG. 36, assumes an enabled state when pressed by the rear end portion 451b of the sliding portion 451. Furthermore, the slide detection switch 473 outputs a switch state signal for indicating whether the state of the slide detection switch 473 is in the disabled state or in the enabled state to the CCU 403.

The endoscope main body 406 is configured so as to include: a hard insertion portion 461 configured in a shape and size allowing insertion into a body cavity; a transparent hood 462 disposed at a distal end portion 461a of the insertion portion 461; an objective lens 463 that collects and forms an image of the living body tissue 501 having passed through the transparent hood 462; and an image pickup device 464 that picks up an image of the living body tissue 501 formed by the objective lens 463 and which outputs the image as an image pickup signal. In addition, at an endoscope main body rear end portion 461b, the insertion portion 461 is configured so as to be detachable with respect to a cylindrical portion 471 of the adapter 407.

The image pickup device 464 including functions as image pickup section is formed by a semiconductor detecting element (photovoltaic semiconductor detecting element) such as InAs which is sensitive in an infrared region exceeding at least a wavelength of 1000 nm.

The CCU 403 is configured to include: an LED drive circuit 431; a signal processing circuit 432; and an image pickup device drive circuit 433 that supplies power for driving the image pickup device 464. Furthermore, the LED drive circuit 431 and the signal processing circuit 432 provided at the CCU 403 are configured as, for example, shown in FIG. 37.

As shown in FIG. 37, the LED drive circuit 431 is configured to include: a state detection circuit 431a; an illumination control circuit 431b; and LED drivers 431c, 431d and 431e.

The state detection circuit 431a detects a state of the slide detection switch 473 based on a switch state signal outputted from the slide detection switch 473 of the adapter 407, and outputs the detection result as a state detection signal to the signal processing circuit 432.

Based on a contrast control signal outputted from the signal processing circuit 432, the illumination control circuit 431b respectively outputs driver control signals for controlling operation states of the LED drivers 431c, 431d and 431e to the LED drivers 431c, 431d and 431e. In addition, the illumination control circuit 431b outputs a driver driven state signal for indicating an LED driver that had been changed to an enabled state by outputting the driver control signal among the LED drivers 431c, 431d and 431e to the signal processing circuit 432 at approximately the same timing as the timing at which the driver control signal was outputted.

The LED driver 431c outputs a drive signal to the LED 453a provided at the illuminating portion 453 based on the driver control signal outputted from the illumination control circuit 431b. Subsequently, the LED 453a shifts from a suspended state to a driven state due to the drive signal, and in the driven state, irradiates the first illuminating light to the living body tissue 501.

The LED driver 431d outputs a drive signal to the LED 453b provided at the illuminating portion 453 based on the driver control signal outputted from the illumination control circuit 431b. Subsequently, the LED 453b shifts from a suspended state to a driven state due to the drive signal, and in the driven state, irradiates the second illuminating light to the living body tissue 501.

The LED driver 431e outputs a drive signal to the LED 453c provided at the illuminating portion 453 based on the driver control signal outputted from the illumination control circuit 431b. Subsequently, the LED 453c shifts from a suspended state to a driven state due to the drive signal, and in the driven state, irradiates the third illuminating light to the living body tissue 501.

As shown in FIG. 37, the signal processing circuit 432 is configured to include: a process circuit 432a that performs processing such as noise reduction on an image pickup signal outputted from the endoscope 402; an A/D converter 432b that converts an image pickup signal outputted from the process circuit 432a to a digital image signal; a digital image processing circuit 432c that performs image processing on a digital image signal outputted from the A/D converter 432b; a selector 432d; and a timing control circuit 432e.

Furthermore, the signal processing circuit 432 is configured to include: memories 432f, 432g and 432h; a contrast control circuit 432i; a luminance comparison circuit 432j; an image synthesis circuit 432k; and a D/A converter 432l.

The timing control circuit 432e outputs, based on a driver driven state signal outputted from the illumination control circuit 431b, a timing signal for setting processing timings of the respective portions of the process circuit 432a, the A/D converter 432b, the digital image processing circuit 432c and the selector 432d. More specifically, based on a driver driven state signal outputted from the illumination control circuit 431b, when it is detected that the LED driver 431c has performed driving, the timing control circuit 432e outputs a first timing signal to the aforementioned respective portions. In addition, based on a driver driven state signal outputted from the illumination control circuit 431b, when it is detected that the LED driver 431d has performed driving, the timing control circuit 432e outputs a second timing signal to the aforementioned respective portions. Furthermore, based on a driver driven state signal outputted from the illumination control circuit 431b, when it is detected that the LED driver 431e has performed driving, the timing control circuit 432e outputs a third timing signal to the aforementioned respective portions.

Based on a timing signal outputted from the timing control circuit 432e, the selector 432d outputs a digital image signal outputted from the digital image processing circuit 432c to any one of the memories 432f, 432g and 432h. More specifically, based on a first timing signal outputted from the timing control circuit 432e, the selector 432d outputs a digital image signal outputted from the digital image processing circuit 432c to the memory 432f. In addition, based on a second timing signal outputted from the timing control circuit 432e, the selector 432d outputs a digital image signal outputted from the digital image processing circuit 432c to the memory 432g. Furthermore, based on a third timing signal outputted from the timing control circuit 432e, the selector 432d outputs a digital image signal outputted from the digital image processing circuit 432c to the memory 432h.

The memories 432f, 432g and 432h temporary store the digital image signal outputted from the selector 432d, and output the digital image signal to the luminance comparison circuit 432j at approximately the same timing based on a read timing of the luminance comparison circuit 432j.

The contrast control circuit 432i outputs a contrast control signal for controlling the respective portions of the illumination control circuit 431b and the luminance comparison circuit 432j to the respective portions based on a state detection signal outputted from the state detection circuit 431a and a luminance value comparison information signal outputted from the luminance comparison circuit 432j.

Based on respective digital image signals read from the respective memories 432f, 432g and 432h and on a contrast control signal outputted from the contrast control circuit 432i, the luminance comparison circuit 432j performs comparison processing of contrasts of the respective images corresponding to the respective digital image signals. Then, the luminance comparison circuit 432*j* outputs information obtained based on comparison results of the comparison processing as a luminance value comparison information signal to the contrast control circuit 432*i*. In addition, among the respective digital image signals outputted from the respective memories 432*f*, 432*g* and 432*h*, the luminance comparison circuit 432*j* outputs a digital image signal corresponding to the comparison result to the image synthesis circuit 432*k*.

The image synthesis circuit 432*k* converts the respective digital image signals outputted from the luminance comparison circuit 432*j* into a digital video signal, and outputs the digital video signal to the D/A converter 432*l*.

The D/A converter 432*l* converts the digital video signal outputted from the image synthesis circuit 432*k* into an analog video signal, and outputs the analog video signal to the monitor 404.

Next, operations of the image pickup system 401 will be described.

First, for example, as shown in FIG. 32, the user inserts the illuminating unit 405 and the insertion portion 461 up to near the living body tissue 501 existing in a desired observation site inside a body cavity while securing a state where the slide detection switch 473 is not pressed by the rear end portion 451*b* of the sliding portion 451. Subsequently, the user presses the illuminating portion 453 of the illuminating unit against the living body tissue 501 to bring the illuminating portion 453 into close contact with the living body tissue 501.

Since the slide detection switch 473 is not pressed by the rear end portion 451*b* of the sliding portion 451, the slide detection switch 473 outputs a switch state signal indicating that the slide detection switch 473 is in a disabled state to the CCU 403.

Based on the switch state signal outputted from the slide detection switch 473 of the adapter 407, the state detection circuit 431*a* outputs a state detection signal indicating that the slide detection switch 473 is in the disabled state to the signal processing circuit 432.

Based on the state detection signal outputted from the state detection circuit 431*a*, when it is detected that the slide detection switch 473 is in the disabled state, the contrast control circuit 432*i* outputs a contrast control signal corresponding to the disabled state to the illumination control circuit 431*b* and the luminance comparison circuit 432*j*.

Based on the contrast control signal outputted from the contrast control circuit 432*i*, the illumination control circuit 431*b* intermittently drives the respective LED drivers 431*c*, 431*d* and 431*e* by, for example, sequentially and continuously outputting a pulsed driver control signal to the respective drivers. In addition, the illumination control circuit 431*b* outputs a driver driven state signal for indicating an LED driver that had been changed to an enabled state by outputting the pulsed driver control signal among the LED drivers 431*c*, 431*d* and 431*e* to the signal processing circuit 432 at approximately the same timing as the timing at which the pulsed driver control signal was outputted.

The LED driver 431*c* outputs a drive signal to the LED 453*a* provided on the illuminating portion 453 based on the driver control signal outputted from the illumination control circuit 431*b* at approximately the same timing as the timing at which the driver control signal was inputted.

The LED 453*a* shifts from a suspended state to a driven state due to the drive signal, and in the driven state, irradiates the first illuminating light to the living body tissue 501. Then, an image of the living body tissue 501 illuminated by the first illuminating light passes through the transparent hood 462 before being formed at the objective lens 463, and after being respectively picked up by the image pickup device 464, inputted as an image pickup signal to the process circuit 432*a* of the CCU 403.

The LED driver 431*d* outputs a drive signal to the LED 453*b* provided on the illuminating portion 453 based on the driver control signal outputted from the illumination control circuit 431*b* at approximately the same timing as the timing at which the driver control signal was inputted.

The LED 453*b* shifts from a suspended state to a driven state due to the drive signal, and in the driven state, irradiates the second illuminating light to the living body tissue 501. Then, an image of the living body tissue 501 illuminated by the second illuminating light passes through the transparent hood 462 before being formed at the objective lens 463, and after being respectively picked up by the image pickup device 464, inputted as an image pickup signal to the process circuit 432*a* of the CCU 403.

The LED driver 431*e* outputs a drive signal to the LED 453*c* provided on the illuminating portion 453 based on the driver control signal outputted from the illumination control circuit 431*b* at approximately the same timing as the timing at which the driver control signal was inputted.

Subsequently, the LED 453*c* shifts from a suspended state to a driven state due to the drive signal, and in the driven state, irradiates the third illuminating light to the living body tissue 501. Then, an image of the living body tissue 501 illuminated by the third illuminating light passes through the transparent hood 462 before being formed at the objective lens 463, and after being respectively picked up by the image pickup device 464, inputted as an image pickup signal to the process circuit 432*a* of the CCU 403.

The image pickup signal based on the image of the living body tissue 501 illuminated by the first illuminating light is subjected to processing at the respective portions of the process circuit 432*a*, the A/D converter 432*b*, the digital image processing circuit 432*c* and the selector 432*d* at a timing based on the first timing signal outputted from the timing control circuit 432*e*. Then, the image pickup signal based on the image of the living body tissue 501 illuminated by the first illuminating light and which was subjected to processing at the respective portions is outputted to the memory 432*f* by the selector 432*d* in a state where the image pickup signal is converted to a digital image signal.

In addition, the image pickup signal based on the image of the living body tissue 501 illuminated by the second illuminating light is subjected to processing at the respective portions of the process circuit 432*a*, the A/D converter 432*b*, the digital image processing circuit 432*c* and the selector 432*d* at a timing based on the second timing signal outputted from the timing control circuit 432*e*. Then, the image pickup signal based on the image of the living body tissue 501 illuminated by the second illuminating light and which was subjected to processing at the respective portions is outputted to the memory 432*g* by the selector 432*d* in a state where the image pickup signal is converted to a digital image signal.

Furthermore, the image pickup signal based on the image of the living body tissue 501 illuminated by the third illuminating light is subjected to processing at the respective portions of the process circuit 432*a*, the A/D converter 432*b*, the digital image processing circuit 432*c* and the selector 432*d* at a timing based on the third timing signal outputted from the timing control circuit 432*e*. Then, the image pickup signal based on the image of the living body tissue 501 illuminated by the first illuminating light and which was subjected to processing at the respective portions is outputted to the memory 432h by the selector 432d in a state where the image pickup signal is converted to a digital image signal.

Based on the respective digital image signals read from the respective memories 432f, 432g and 432h and on the contrast control signal outputted from the contrast control circuit 432i, the luminance comparison circuit 432j does not perform contrast comparison processing on the respective digital image signals read from the respective memories 432f, 432g and 432h and outputs the respective digital image signals without modification.

The image synthesis circuit 432k synthesizes respective images based on the respective digital image signals outputted from the luminance comparison circuit 432j and converts the images into a digital video signal, and outputs the digital video signal to the D/A converter 432l.

The D/A converter 432l converts the digital video signal outputted from the image synthesis circuit 432k into an analog video signal, and outputs the analog video signal to the monitor 404.

According to the operations described heretofore, an image in which is synthesized an image of the living body tissue 501 illuminated by the first illuminating light, an image of the living body tissue 501 illuminated by the second illuminating light, and an image of the living body tissue 501 illuminated by the third illuminating light is displayed on the monitor 404.

Furthermore, as the illuminating unit 405 and the insertion portion 461 reach a location on the surface of the living body tissue 501 at which exists blood vessels 503 to be objects of obtaining a vascular flow, the user presses the distal end portion 461a of the insertion portion 461 in addition to the illuminating portion 453 of the illuminating unit 405 against the living body tissue 501 to bring the distal end portion 461a into close contact with the living body tissue 501. By performing such an operation, the user places the respective LEDS provided at the illuminating portion 453 and the transparent hood 462 of the endoscope main body 406 at, for example, positions such as shown in FIG. 38 with respect to a surface of the living body tissue 501. Incidentally, in FIG. 38 for the sake of brevity, it is assumed that any one type of LED among the LEDS 453a, 453b and 453c shall be depicted as the LED 453i. In addition, it is assumed that the state shown in FIG. 38 is a state immediately prior to the slide detection switch 473 being pressed by the rear end portion 451b of the sliding portion 451.

When assuming that the LED 453i shown in FIG. 38 is the LED 453a, a major portion of the first illuminating light irradiated from the LED 453a becomes reflected light reflected at the fat 502 existing in the vicinity of a superficial layer of the living body tissue 501 and which has, for example, an optical path such as that represented by the dashed-dotted line in FIG. 38. Then, an image of the living body tissue 501 and the blood vessels 503 illuminated by the first illuminating light and based on the reflected light passes through the transparent hood 462 before being formed at the objective lens 463, and after being respectively picked up by the image pickup device 464, inputted as an image pickup signal to the process circuit 432a of the CCU 403.

When assuming that the LED 453i shown in FIG. 38 is the LED 453b, a major portion of the second illuminating light irradiated from the LED 453b becomes reflected light reflected at the fat 502 existing in the vicinity of an intermediate layer of the living body tissue 501 and which has, for example, an optical path such as that represented by the dashed-two dotted line in FIG. 38. Then, an image of the living body tissue 501 and the blood vessels 503 illuminated by the second illuminating light and based on the reflected light passes through the transparent hood 462 before being formed at the objective lens 463, and after being respectively picked up by the image pickup device 464, inputted as an image pickup signal to the process circuit 432a of the CCU 403.

When assuming that the LED 453i shown in FIG. 38 is the LED 453c, a major portion of the third illuminating light irradiated from the LED 453c becomes reflected light reflected at the blood vessels 503 existing in the vicinity of a deep layer of the living body tissue 501 and which has, for example, an optical path such as that represented by the dotted line in FIG. 38. Then, an image of the living body tissue 501 and the blood vessels 503 illuminated by the third illuminating light and based on the reflected light passes through the transparent hood 462 before being formed at the objective lens 463, and after being respectively picked up by the image pickup device 464, inputted as an image pickup signal to the process circuit 432a of the CCU 403.

The image pickup signal based on the image of the living body tissue 501 illuminated by the first illuminating light is subjected to processing at the respective portions of the process circuit 432a, the A/D converter 432b, the digital image processing circuit 432c and the selector 432d at a timing based on the first timing signal outputted from the timing control circuit 432e. Then, the image pickup signal based on the image of the living body tissue 501 illuminated by the first illuminating light and which was subjected to processing at the respective portions is outputted to the memory 432f by the selector 432d in a state where the image pickup signal is converted to a digital image signal.

In addition, the image pickup signal based on the image of the living body tissue 501 illuminated by the second illuminating light is subjected to processing at the respective portions of the process circuit 432a, the A/D converter 432b, the digital image processing circuit 432c and the selector 432d at a timing based on the second timing signal outputted from the timing control circuit 432e. Then, the image pickup signal based on the image of the living body tissue 501 illuminated by the second illuminating light and which was subjected to processing at the respective portions is outputted to the memory 432g by the selector 432d in a state where the image pickup signal is converted to a digital image signal.

Furthermore, the image pickup signal based on the image of the living body tissue 501 illuminated by the third illuminating light is subjected to processing at the respective portions of the process circuit 432a, the A/D) converter 432b, the digital image processing circuit 432c and the selector 432d at a timing based on the third timing signal outputted from the timing control circuit 432e. Then, the image pickup signal based on the image of the living body tissue 501 illuminated by the first illuminating light and which was subjected to processing at the respective portions is outputted to the memory 432h by the selector 432d in a state where the image pickup signal is converted to a digital image signal.

Subsequently, the sliding portion 451 is slid further towards a proximal end-side of the endoscope 402 and, for example, in a state such as shown in FIG. 36, when the slide detection switch 473 is pressed by the rear end portion 451b of the sliding portion 451, the slide detection switch 473 outputs a switch state signal for indicating that the slide detection switch 473 has assumed an enabled state to the CCU 403.

Based on the switch state signal outputted from the slide detection switch 473 of the adapter 407, the state detection circuit 431a outputs a state detection signal indicating that the slide detection switch 473 is in the enabled state to the signal processing circuit 432.

Based on the state detection signal outputted from the state detection circuit 431a, when the contrast control circuit 432i detects that the slide detection switch 473 is in the disabled state, the contrast control circuit 432i outputs a contrast control signal corresponding to the enabled state to the luminance comparison circuit 432j.

When the luminance comparison circuit 432j as luminance value comparison section detects that the slide detection switch 473 is in the enabled state based on the contrast control signal outputted from the contrast control circuit 432i, the luminance comparison circuit 432j performs comparison processing of contrasts between the respective images while, for example, using luminance value detection results according to a method in which luminance values of pixels existing at positions that are approximately central in a vertical direction of the respective images corresponding to respective digital image signals read from the respective memories 432f, 432g and 432h are sequentially detected in a horizontal direction, as described hereinafter.

More specifically, when the image read from the memory 432f is the image shown in FIG. 39, the luminance comparison circuit 432j obtains, for example, a detection result such as shown in FIG. 42 by sequentially detecting, in a horizontal direction, luminance values of pixels existing at a position that is approximately the center of the image in a vertical direction.

In addition, when the image read from the memory 432g is the image shown in FIG. 40, the luminance comparison circuit 432j obtains, for example, a detection result such as shown in FIG. 43 by sequentially detecting, in a horizontal direction, luminance values of pixels existing at a position that is approximately the center of the image in a vertical direction.

Furthermore, when the image read from the memory 432h is the image shown in FIG. 41, the luminance comparison circuit 432j obtains, for example, a detection result such as shown in FIG. 44 by sequentially detecting, in a horizontal direction, luminance values of pixels existing at a position that is approximately the center of the image in a vertical direction.

Then, based on the luminance value detection result of each image, the luminance comparison circuit 432j as luminance value comparison section compares luminance value differences of an image of the blood vessel 503 and an image other than the blood vessel 503 in the respective images read from the respective memories 432f, 432g and 432h. Then, among the respective images read from the respective memories 432f, 432g and 432h, the luminance comparison circuit 432j as image extracting section extracts a single image having a maximum difference in luminance values of an image of the blood vessel 503 and an image other than the blood vessel 503 in an image of the living body tissue 501. Subsequently, the luminance comparison circuit 432j outputs information regarding the single image as a luminance value comparison information signal to the contrast control circuit 432i.

More specifically, when the luminance comparison circuit 432j obtains, for example, detection results such as shown in FIGS. 42, 43 and 44 as detection results of luminance values in the respective images, the luminance comparison circuit 432j extracts the image shown in FIG. 41 as the image having a maximum difference in luminance values of an image of the blood vessel 503 and an image other than the blood vessel 503 in an image of the living body tissue 501. Then, the luminance comparison circuit 432j outputs information regarding the image shown in FIG. 41 as a luminance value comparison information signal to the contrast control circuit 432i.

Incidentally, in the eighth embodiment, after performing the luminance value comparison processing described above, the luminance comparison circuit 432j does not perform luminance value comparison processing until the luminance comparison circuit 432j detects that the slide detection switch 473 once again shifts from the disabled state to the enabled state, and outputs the respective digital image signals read from the respective memories 432f, 432g and 432h without modification.

Subsequently, based on the luminance value comparison information signal outputted from the luminance comparison circuit 432j, the contrast control circuit 432i judges that the image shown in FIG. 41 is the single image in which the contrast between an image of the blood vessel 503 and an image other than the blood vessel 503 in an image of the living body tissue 501 becomes maximum. Then, the contrast control circuit 432i including functions as illumination selecting section selects a single illuminating light having a single wavelength band that enables an image having the same luminance value difference as the single image to be obtained among respective illuminating light irradiated from the respective LEDs of the illuminating portion 453. Furthermore, the contrast control circuit 432i outputs a contrast control signal for performing control according to the selection result to the illumination control circuit 431b.

Based on the contrast control signal outputted from the contrast control circuit 432i, the illumination control circuit 431b continuously causes the LED driver 431e to assume an enabled state by outputting a driver control signal to the LED driver 431e and changes the LED drivers 431c and 431d to a disabled state by suspending the output of driver control signals to the LED drivers 431c and 431d.

When the LED driver 431e is in the enabled state and the LED drivers 431c and 431d are in the disabled state, illuminating light is only irradiated from the LED 453c of the illuminating portion 453 and no illuminating light is irradiated from the LEDs 453a and 453b. Consequently, an image of the living body tissue 501 and the blood vessels 503 illuminated by the third illuminating light is formed on the objective lens 463.

The image of the living body tissue 501 and the blood vessels 503 illuminated by the third illuminating light is formed at the objective lens 463, and after being respectively picked up by the image pickup device 464, the image is inputted as an image pickup signal to the process circuit 432a.

The image pickup signal based on the image of the living body tissue 501 and the blood vessels 503 illuminated by the third illuminating light is subjected to processing at the respective portions of the process circuit 432a, the A/D converter 432b, the digital image processing circuit 432c and the selector 432d at a timing based on the third timing signal outputted from the timing control circuit 432e. Then, the image pickup signal based on the image of the living body tissue 501 illuminated by the third illuminating light and which was subjected to processing at the respective portions is outputted to the memories 432f, 432g and 432h by the selector 432d in a state where the image pickup signal is converted to a digital image signal.

Based on the respective digital image signals read from the respective memories 432f, 432g and 432h and on the contrast control signal outputted from the contrast control circuit 432i, the luminance comparison circuit 432j does not perform luminance value comparison processing on the respective digital image signals read from the respective memories 432f, 432g and 432h and outputs the respective digital image signals without modification.

The image synthesis circuit 432k synthesizes respective images based on the respective digital image signals outputted from the luminance comparison circuit 432j and converts the images into a digital video signal, and outputs the digital video signal to the D/A converter 432l.

The D/A converter 432l converts the digital video signal outputted from the image synthesis circuit 432k into an analog video signal, and outputs the analog video signal to the monitor 404.

According to the operations heretofore described, for example, the image shown in FIG. 41 is image-displayed on the monitor 404 as an image of the living body tissue 501 and the blood vessels 503 illuminated by the third illuminating light.

As described above, the image pickup system 401 according to the eighth embodiment is capable of obtaining a state of vascular flow of blood vessels covered by fat and which exist in a living body tissue of a desired observation site without having to perform operations such as removal of the fat surrounding the blood vessels. As a result, compared to conventional arrangements, the image pickup system 401 according to the eighth embodiment is capable of reducing the time period required for performing treatment on living body tissue.

In addition, with respect to blood vessels existing in a living body tissue in a desired observation site and which is covered with fat, the image pickup system 401 according to the eighth embodiment is capable of irradiating illuminating light having a wavelength band in accordance with the depth at which the blood vessels in the living body tissue exist. As a result, the image pickup system 401 according to the eighth embodiment is capable of obtaining an image having a high contrast between an image of blood vessels that are objects of obtaining vascular flow and an image other than the blood vessels among images of the living body tissue of the desired observation site.

Incidentally, when the wavelength band included in the illuminating lights irradiated from the respective LEDs 453a, 453b and 453c is set to a predetermined wavelength band at which a difference between the optical transmittance of fat and the optical transmittance of blood vessels (walls of blood vessels) in the living body tissue 501 becomes maximum, the image pickup system 401 according to the eighth embodiment is capable of obtaining an image having an even higher contrast between an image of blood vessels that are objects of obtaining vascular flow and an image other than the blood vessels. More specifically, the predetermined wavelength band is either one of, for example, a wavelength band of 1450 nm±50 nm indicated by the reference character Ac in FIG. 35 or a wavelength band of 1950 nm±50 nm indicated by the reference character Bc in FIG. 35.

(Ninth Embodiment)

Figure 45:
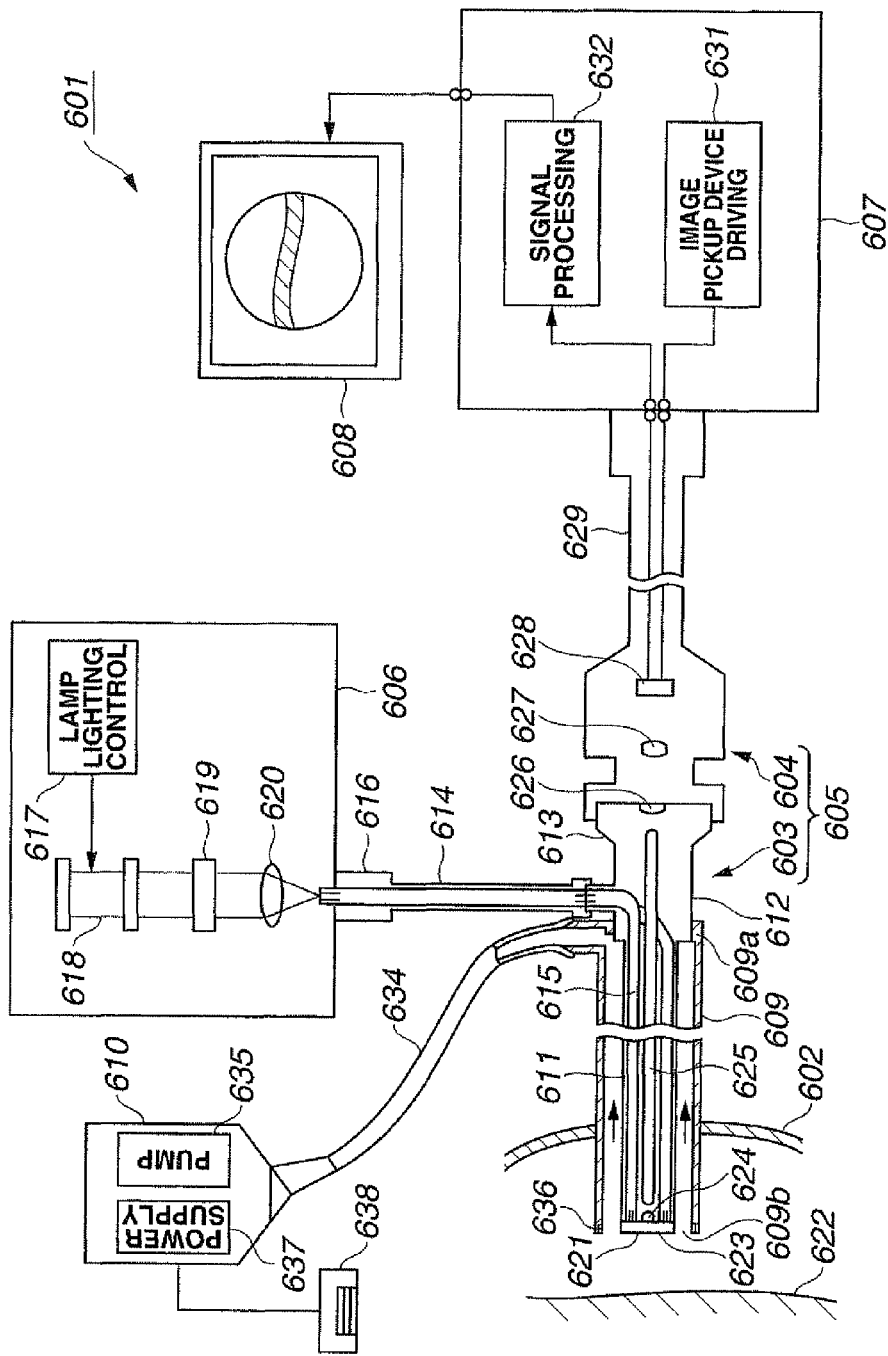
FIG. 45 is an overall configuration diagram of an endoscope apparatus according to a ninth embodiment of the present invention.
Figure 46:
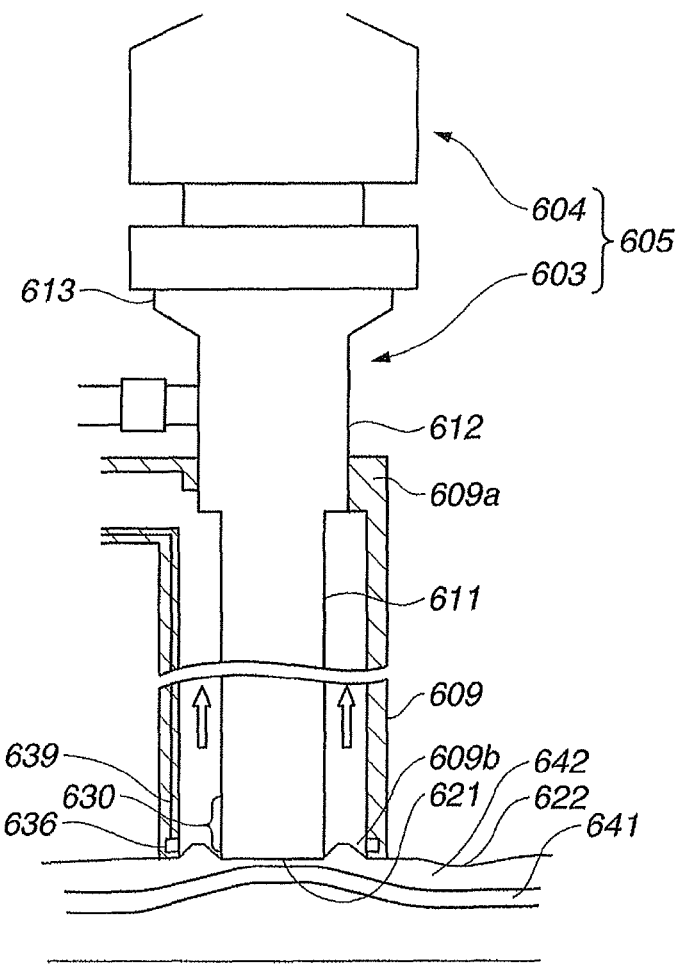
FIG. 46 is a diagram showing an endoscope during vascular observation by a usage example.
Figure 47:
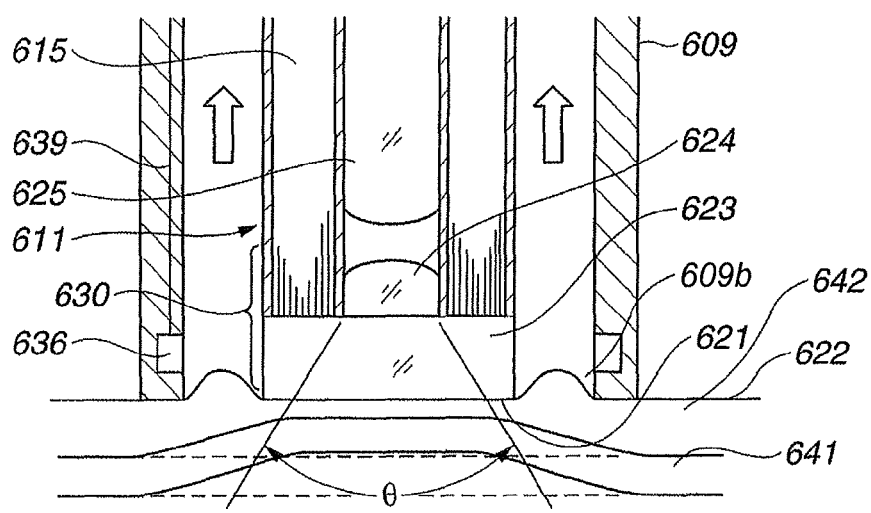
FIG. 47 is an enlarged view of the vicinity of a distal end portion shown in FIG. 46.
Figure 48:
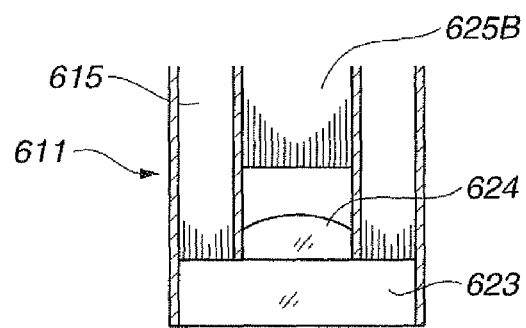
FIG. 48 is a diagram showing a configuration of a distal end portion of an endoscope according to a modification.
Figure 49:
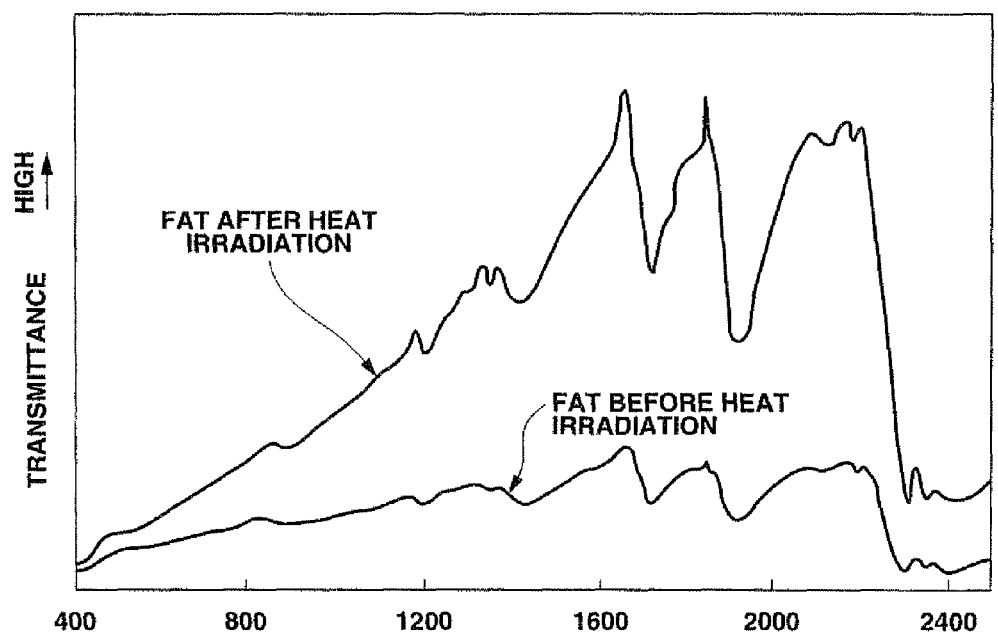
FIG. 49 is a diagram showing transmittance characteristics of fat before and after heat irradiation is applied.
Figure 50:
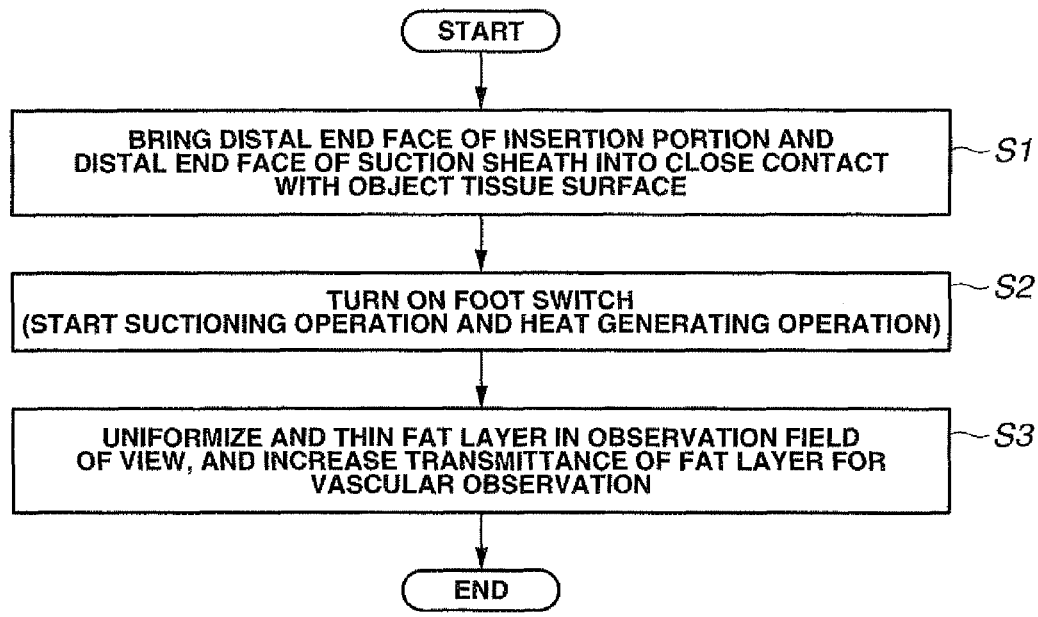
FIG. 50 is a flowchart diagram showing a vascular observation method according to the ninth embodiment.

FIGS. 45 to 50 relate to a ninth embodiment of the present invention, wherein: FIG. 45 is an overall configuration diagram of an endoscope apparatus according to the ninth embodiment of the present invention; FIG. 46 is a diagram showing an endoscope during vascular observation; FIG. 47 is an enlarged view of a vicinity of a distal end portion shown in FIG. 46; FIG. 48 is a diagram showing a configuration of a distal end portion of an endoscope according to a modification; FIG. 49 is a diagram showing transmittance characteristics of fat before and after heat irradiation is applied; and FIG. 50 is a flowchart diagram showing a vascular observation method according to the ninth embodiment.

As shown in FIG. 45, an endoscope apparatus 601 according to the ninth embodiment of the present invention includes: a camera-mounted endoscope (hereinafter simply abbreviated to endoscope) 605 in which a camera head 604 incorporating built-in image pickup section is mounted to, for example, an optical endoscope 603 whose distal end-side is to be inserted into, for example, an abdominal portion 602; a light source apparatus 606 that supplies illuminating light to the optical endoscope 603; a camera control unit (abbreviated to CCU) 607 that performs signal processing with respect to the image pickup section built into the camera head 604; a monitor 608 that receives input of a standard video signal outputted from the CCU 607 and displays an endoscopic image picked up by the image pickup section; a sheath for suction (abbreviated to suction sheath) 609 detachably mounted to the optical endoscope 603; and a suction apparatus 610 connected to a proximal end-side of the suction sheath 609 and which has built-in suction section and performs suction.

The optical endoscope 603 includes: an insertion portion 611 that is, for example, rigid; a grasping portion 612 provided on a rear end of the insertion portion 611; and an eyepiece portion 613 provided on a rear end of the grasping portion 612, wherein a light guide cable 614 is connected to a cap of the grasping portion 612.

A light guide 615 that transmits illuminating light is inserted through the insertion portion 611. A light guide connector 616 provided at an end portion of the light guide 615 via the light guide cable 614 connected to a cap at a side portion of the grasping portion 612 is detachably connected to the light source apparatus 606.

A lamp 618 such as a halogen lamp which is lighted by a lamp lighting power source supplied from a lamp lighting control circuit 617 is provided inside the light source apparatus 606. The lamp 618 covers wavelength bands in the visible region and, at the same time, generates light in the infrared region having a wavelength exceeding 1000 nm.

Among light from the lamp 618, only infrared light in the infrared region is passed through an infrared filter 619 disposed on an illuminating optical path. The infrared light is then collected by a collecting lens 620 and travels through the light guide of the light guide cable 614, whereby the illuminating light is incident to the light guide 615 of the optical endoscope 603.

Furthermore, the infrared illuminating light incident to the light guide 615 is guided (transmitted) to a distal end-side of the light guide 615. The infrared illuminating light is then irradiated from a distal end-face of the light guide 615.

As shown in FIG. 46 or 47, a distal end face 621 of a distal end portion 630 provided on a distal end of the insertion portion 611 of the optical endoscope 603 is formed as a circular flat face that is perpendicular to an axial direction of the insertion portion 611, and is arranged so that the distal end face 621 can be brought into close contact with living body tissue surface 622 of an observation object (abbreviated to object tissue surface) 622 such as a gastroepiploic portion of the abdominal portion 602.

As shown in FIG. 47, a transparent hood 623 formed of glass or the like and having, for example, a disk-like shape is mounted to the distal end face 621 of the insertion portion 611. An objective lens 624 is disposed at a central position on an inner side of the transparent hood 623, and the light guide 615 having, for example, a ring shape is disposed around the objective lens 624.

In this case, a portion of the transparent hood 623 opposing the distal end face of the ring-shaped light guide 615 is provided with functions of an illuminating window that irradiates illuminating light, while a central portion of the transparent hood 623 opposing the objective lens 624 is provided with functions of an observing window into which illuminating light is incident.

Reflected light of the illuminating light irradiated from the distal end face of the light guide 615 is incident to the objective lens 624, whereby the objective lens 624 forms an optical image at an image-forming position thereof. The optical image is transmitted to a posterior eyepiece portion 613 side by a relay lens system 625 disposed inside the insertion portion 611.

The transmitted optical image becomes observable under magnification via an eyepiece lens 626 provided at the eyepiece portion 613 as shown in FIG. 45. In a case where the camera head 604 is mounted to the eyepiece portion 613, an optical image transmitted via an image pickup lens 627 inside the camera head 604 is formed on an image pickup device 628.

The image pickup device 628 is an image pickup device formed using a semiconductor detecting element (photovoltaic semiconductor detecting element) such as Ex-InGaAs, InAs, and InSb and which is sensitive in an infrared region exceeding, for example, a wavelength of 1000 nm. An image pickup device using such a semiconductor detecting element is sensitive in a wavelength band ranging from at least 1000 nm to around 2550 nm. Incidentally, InAs and InSb are also sensitive in long wavelength regions of 3000 nm or more which have longer wavelengths than 2550 nm.

In addition, a camera cable 629 extended from the camera head 604 is connected to the CCU 607. The CCU 607 includes an image pickup device drive circuit 631 and a signal processing circuit 632, in which the image pickup device drive circuit 631 applies an image pickup device drive signal to the image pickup device 628.

An image pickup signal photoelectrically converted by the image pickup device 628 due to the application of the image pickup device drive signal is inputted to the signal processing circuit 632. The signal processing circuit 632 performs signal processing for generating a video signal on the inputted image pickup signal.

The generated video signal is outputted to the monitor 608, whereby an image picked up by the image pickup device 628 is displayed on a display screen of the monitor 608.

In addition, the suction sheath 609 detachably mounted so as to cover the insertion portion 611 of the optical endoscope 603 by having a mounting portion 609*a* at a proximal end of the suction sheath 609 fit onto the grasping portion 612 of the optical endoscope 603 has a hollow cylindrical shape. The suction sheath 609 is connected to the suction apparatus 610 via a suction tube 634 connected to a cap portion provided near the proximal end of the suction sheath 609.

The inside of the suction apparatus 610 is communicated with the suction tube 634 and a hollow portion of the suction sheath 609, and is provided with a suction pump 635 that performs suction of fluids such as air and a heat generating element power source (simply abbreviated to power source in FIG. 45) 637 that supplies driving power to a heat generating element 636 provided near the distal end portion of the suction sheath 609.

In addition, a foot switch 638 for enabling/disabling operations of the suction pump 635 and operations for supplying drive power to the heat generating element 636 is connected to the suction apparatus 610 and is arranged so as to enable a user such as an operator to enable/disable operations of the suction pump 635 and the heat generating element 636 by operating the foot switch 638.

Incidentally, as shown in FIG. 47, the heat generating element 636 is internally provided in, for example, a ring shape near, for example, the distal end portion of the suction sheath 609, and is electrically connected to the power source 637 shown in FIG. 45 via a power supply line 639 that is, for example, embedded in a longitudinal direction of the suction sheath 609.

In FIG. 47, while an example is shown in which a relay lens system 625 is adopted as means for transmitting an optical image by the objective lens 624, an image guide 625B formed by a fiber bundle as shown in FIG. 48 may also be adopted. In this case, a distal end face of the image guide 625B is disposed at an image-forming position of the objective lens 624, whereby an optical image formed on the distal end face is transmitted to a rear end face of the image guide 625B.

The ninth embodiment is arranged such that, by setting a state in which the distal end face 621 of the insertion portion 611 and the distal end face of the suction sheath 609 is brought into close contact with the object tissue surface 622 that is the observation object such as shown in FIG. 46 or 47 and by operating the suction pump 635 of the suction apparatus 610, distance reducing section is formed which reduces the distance from a portion of the object tissue surface 622 opposing the distal end face 621 to blood vessels 641 as internal observation object tissue which run inside the surface 622.

Furthermore, according to the distance reducing section, observation (image pickup) of blood vessels with favorable S/N is enabled by reducing attenuation in light intensity of illuminating light and observation light incident from the observation window to the objective lens 624 at a living body tissue such as fat 642 interposed between the object tissue surface 622 to the blood vessels 641 running therein. Incidentally, in FIGS. 46 and 47, while the positions of the distal end face 621 of the insertion portion 611 and the distal end face of the suction sheath 609 in the longitudinal direction of the insertion portion 611 are arranged to be the same, different positions may be set as shown in a tenth embodiment to be described later.

The aforementioned distance reducing section is formed as described below. By causing the suction pump 635 to perform suction, the suction pump 635 sucks the air in a hollow portion surrounding the insertion portion 611 as indicated by the arrows shown in FIGS. 46 and 47. As a result of the suction, a force that sucks a portion of the object tissue opposing a ring-shape distal end opening 609*b* of an outer peripheral portion of the distal end face 621 towards the inside of the distal end opening 609*b* acts from the distal end opening 609*b* and, as shown in FIGS. 46 and 47, the object tissue is sucked towards the inside of the distal end opening 609*b*.

When the portion of the object tissue opposing the aforementioned ring-shape distal end opening 609*b* moves due to the suction, a portion of the object tissue opposing the distal end face 621 that is now on an inner peripheral side of the ring-shape distal end opening 609*b* deforms and moves so as to be attracted towards the suction apparatus 610 side (i.e., the objective lens 624 side) by the aforementioned suction. Due to the deformation and movement, the distance of the blood vessels 641 and the like from the distal end face 621 is reduced in comparison to prior to the deformation and movement.

In other words, due to the suction operation of the suction pump 635, an internal tissue portion of the object tissue surface 622 near a portion opposing the distal end face 621, or more specifically, an internal tissue portion of the object tissue surface 622 inside an observation field of view (the range of the field of view is indicated by θ in FIG. 47) of the objective lens 624 disposed at the center of the distal end face 621 is attracted towards the objective lens 624 side, thereby reducing (shortening) the distance to the blood vessels 641 as internal observation object tissue inside the object tissue surface 622 and enabling a condition to be set in which a state of vascular flow of blood vessels is readily observed. Incidentally, the insertion portion 611 is concentrically disposed at the center of the suction sheath 609.

Furthermore, as described later, by bringing the distal end face 621 into close contact with the object tissue surface 622, it is also possible to suppress irregularities and the like of the object tissue surface 622 inside the observation field of view θ to enable uniformization of the fat 642 layer substantially forming the living body tissue existing around the internal blood vessels 641.

Moreover, in this case, by causing the heat generating element 636 to generate heat, when the living body tissue existing around the blood vessels 641 running from the object tissue surface 622 to the inside is the fat 642, the transmittance of the fat 642 is raised (increased) to raise the optical transmittance of the fat 642 layer portion, thereby enabling blood vessels 641 underneath the fat 642 to be readily observed. In other words, in the case where the living body tissue surrounding the blood vessels 641 is substantially the fat 642, the heat generating element 636 includes functions of transmittance increasing section for increasing transmittance with respect to infrared light to be used for illumination and observation.

An example of characteristics of a measurement result in which, by performing heat irradiation on fat, the transmittance of the fat increases is shown in FIG. 49. FIG. 49 shows a measurement result of transmittance of fat before and after heat irradiation.

As for conditions of the heat irradiation, shown is a case where, for example, a 1200 W dryer is used as a heat source to irradiate heat to fat to be a measurement object sample for 10 seconds. As shown, due to heat irradiation, the transmittance of fat at least with respect to infrared light can be increased to enable observation images of blood vessel under fat or the like to be obtained at a favorable S/N.

Next, operations of a case will be described in which a surgical operation or the like is performed under observation by the endoscope 605 taking, for example, the stomach inside the abdominal portion 602 as an observation object tissue.

As shown in FIG. 45, the insertion portion 611 of the endoscope 605 is inserted into the abdominal portion 602 via a trocar, not shown. The stomach is covered by an omental portion. The omental portion in adults accumulates fat 642 and becomes thick because of the fat tissue. Thus, there may be cases where, due to the tissue of the fat 642, grasping a state of vascular flow of the blood vessels 641 inside the object tissue surface 622 becomes difficult.

In such a case, the state of vascular flow of the blood vessels 641 can be observed by a method such as shown in FIG. 50. As shown in step S1 of FIG. 50, an operator brings the distal end face 621 of the insertion portion 611 of the endoscope 605 and the distal end face of the suction sheath 609 into close contact with the object tissue surface 622.

Next, the operator steps on the foot switch 638 as shown in step S2 to activate the foot switch 638. As a result, the suction pump 635 commences a suction operation and the heat generating element 636 commences a heat generating operation. Then, a state is achieved in which, as shown in an outline described in step S3, a fat 642 layer configuring the living body tissue within an observation field of view θ and which extends from the object tissue surface 622 to the blood vessels 641 is uniformized and thinned (shortened) and a transmittance of the fat 642 layer is increased to enable vascular observation.

In this case, due to the suction operation of the suction pump 635, as shown in FIG. 46 or 47, a portion of the object tissue surface 622 facing the distal end opening 609b of the suction sheath 609 is drawn towards the inside of the distal end opening 609b.

Due to the suction operation, the portion of the object tissue surface 622 opposing the distal end face 621 of the insertion portion 611 disposed at a central position of the distal end opening 609b deforms and moves so as to be attracted towards the endoscope side. In the example illustrated in FIGS. 46 and 47, the portion of the object tissue portion opposing the distal end face 621 moves more upwards than an object tissue portion that is to the outside of the distal end opening 609b.

Due to the movement when blood vessels 641 are running inside the object tissue as an internal observation object tissue according to the ninth embodiment, the blood vessels 641 also deform and move from, for example, the position indicated by the dotted line in FIG. 47 towards a distal end face 621 side (i.e., the objective lens 624 side) as indicated by the bold line.

As shown, a portion opposing the distal end face 621 or, in other words, the blood vessels 641 as an internal observation object tissue that enters the observation field of view θ of the objective lens 624 can be moved towards the objective lens 624 side in order to reduce the distance therebetween.

In this case, specifically using a distance reducing function or distance reducing section for reducing the distance between the object tissue surface 622 and the blood vessels 641, the fat 642 portion existing around the blood vessels 641 may be specifically thinned in order to reduce attenuation of an illuminating light for illuminating the blood vessels 641 at the fat 642 portion or to reduce attenuation of observation light when light reflected by the blood vessels 641 is incident to the objective lens 624.

More specifically, by reducing (or thinning) the fat 642 layer interposed between the object tissue surface 622 and the blood vessels 641 by around 1 mm using the aforementioned distance reducing section, an observation state of the blood vessels 641 by infrared light can be significantly improved. As seen, the distance reducing section may also be described as means for reducing the fat 642 layer interposed between the living body surface and the blood vessels 641 and which inhibits observation when observing the blood vessels 641.

As described above, according to the ninth embodiment, even when performing a surgical operation under an endoscope by inserting the endoscope into a body cavity, a state of vascular flow of blood vessels 641 running inside a living body tissue such as the fat 642 can now be observed under improved S/N. Therefore, since an operator is able to grasp the vascular flow, treatment such as an excision while avoiding portions of the blood vessels 641 can be performed smoothly and in a short time period. Consequently, the time period required for surgery can be significantly reduced and the burden on both the operator and the patient can be significantly alleviated.

(Tenth Embodiment)

Figure 51:
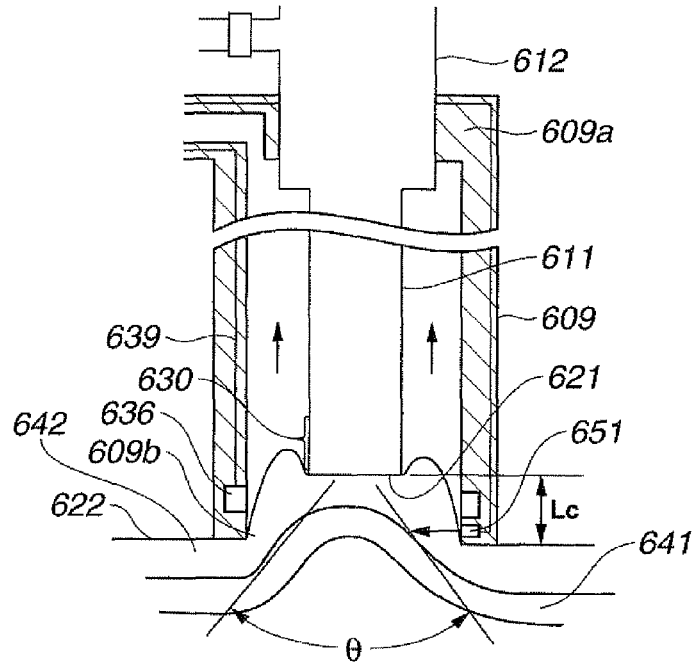
FIG. 51 is a diagram showing, by a usage example, a distal end-side of an endoscope during vascular observation according to a tenth embodiment of the present invention.

Next, a tenth embodiment of the present invention will be described with reference to FIGS. 51 to 54. FIG. 51 is a diagram showing, using a usage example, a configuration of a distal end-side of an endoscope and a suction sheath according to the tenth embodiment. In the tenth embodiment, a laser diode (abbreviated to LD) 651 as a light generating element is mounted to an inner peripheral face near a distal end of the suction sheath 609 according to the ninth embodiment. The LD 651 emits laser light in a wavelength having a high transmittance with respect to fat and blood vessels and a lower transmittance with respect to blood such as, for example, a plurality of wavelengths in the infrared region indicated by the dotted line in FIG. 53.

An outputting face of the LD 651 is disposed so as to irradiate laser light towards a center side of the distal end opening 609b of the suction sheath 609 or, in other words, towards a center side of the observation field of view. Accordingly, the LD 651 irradiates infrared laser light towards a center side of the distal end opening 609b in, for example, a linear formation.

Additionally, in the tenth embodiment, a position of the distal end face 621 of the insertion portion 611 in a longitudinal direction of the insertion portion 611 is set posterior to a position of the distal end face of the suction sheath 609 in the longitudinal direction of the insertion portion 611 (more specifically, the distance therebetween is denoted as Lc in FIG. 51). Furthermore, in the tenth embodiment, the endoscope and the suction sheath 609 is set to a state such as shown in FIG. 51 by operating the suction apparatus 610 by a method such as used in the ninth embodiment.

Figure 52A:
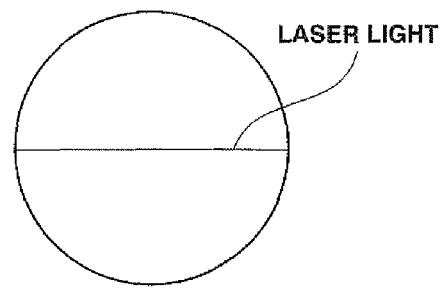
FIG. 52A is a diagram showing an example of an observation image in a case where blood vessels do not exist on an optical path of a laser light.
Figure 52B:
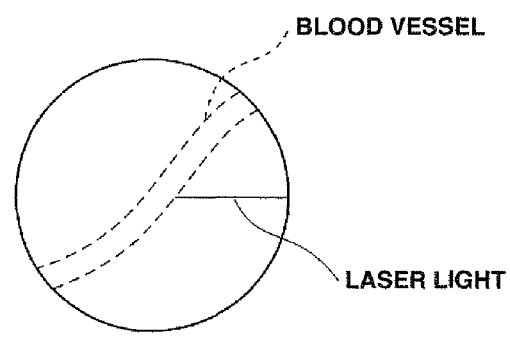
FIG. 52B is a diagram showing an example of an observation image in a case where blood vessels exist on an optical path of a laser light.
Figure 53:
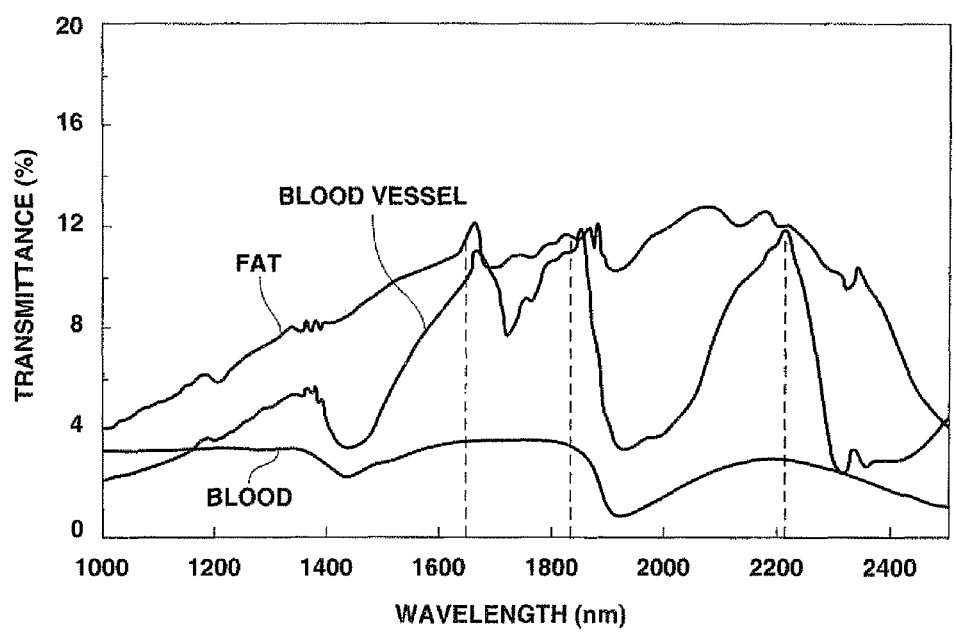
FIG. 53 is a diagram showing an example of wavelengths of laser light.

In this case, if blood vessels 641 exist within a distance of around Lc from the distal end face 621 in the observation field of view θ, since the laser light is absorbed by a blood portion inside the blood vessels 641 as shown in FIG. 52B, the laser light is observed as though interrupted midway.

In contrast, if blood vessels 641 do not exist within a distance of around Lc from the distal end face 621 in the observation field of view θ, the laser light is observed as being uninterrupted as shown in FIG. 52A. Therefore, the presence of blood vessels can be readily confirmed from the observed state of the laser light.

Figure 54:
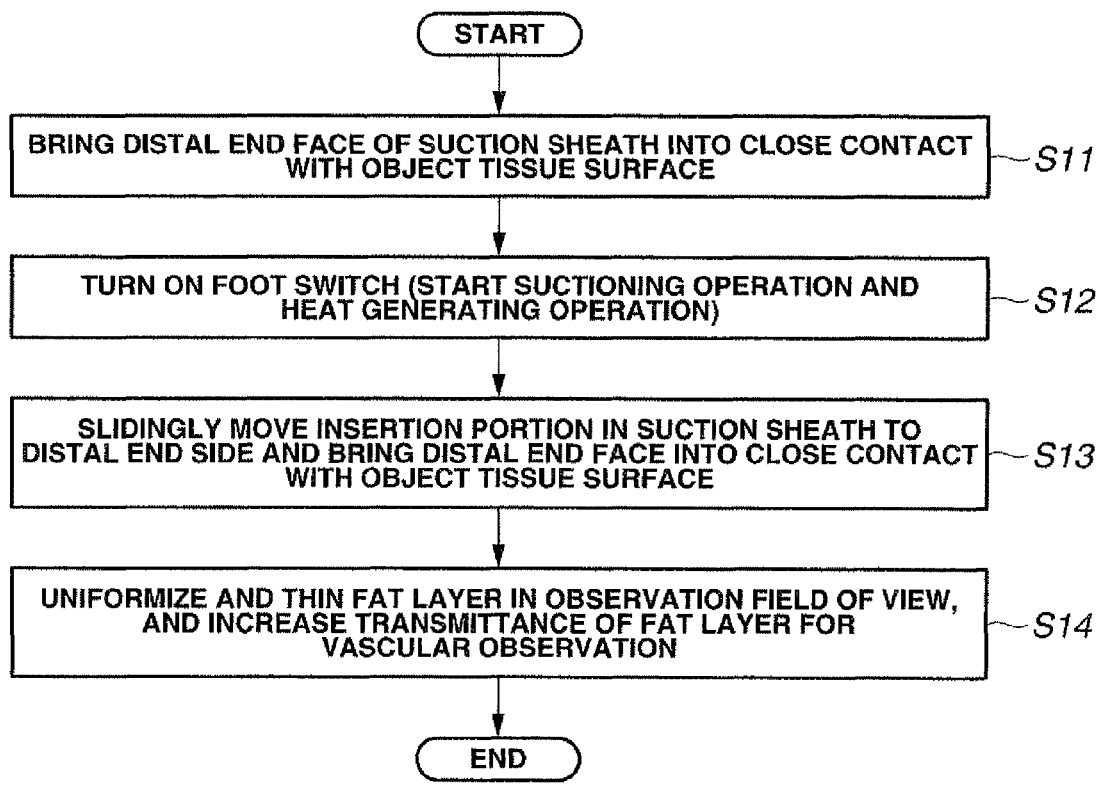
FIG. 54 is a flowchart diagram showing a vascular observation method according to the tenth embodiment.

Incidentally, in the tenth embodiment, while vascular observation may be performed in the method shown in FIG. 50 according to the ninth embodiment, vascular observation may also be performed in a method shown in FIG. 54.

In the tenth embodiment, as shown in FIG. 51, the mounting portion 609a on a proximal end of the suction sheath 609 fits onto the grasping portion 612 of the optical endoscope 603 and is set so as to be slidable in a longitudinal direction (upwards and downwards in FIG. 51) of the grasping portion 612.

As shown in FIG. 54, when performing vascular observation while in close contact with the object tissue surface 622, in a first step S11, an operator brings the distal end face of the suction sheath 609 into close contact with the object tissue surface 622.

In this case, the position of the mounting portion 609a of the suction sheath 609 is assumed to be set anterior to the state shown in FIG. 51 (the grasping portion 612 is assumed to be posterior to the position shown in FIG. 51).

Then, as shown in step S12, the operator activates the foot switch 638. Consequently, the suction pump 635 commences a suction operation and the heat generating element 636 commences a heat generating operation. Due to the suction operation of the suction pump 635, a portion of the object tissue surface 622 facing the distal end opening 609b of the suction sheath 609 is drawn towards the inside of the distal end opening 609b. In addition, due to the heat generating operation of the heat generating element 636, the transmittance of fat with respect to infrared light inside the object tissue surface 622 in the vicinity of the heat generating element 636 is increased.

In the next step S13, the operator slidingly moves the insertion portion 611 towards the distal end-side in the suction sheath and brings the distal end face 621 into close contact with the object tissue surface 622 by pressing the distal end face 621 against the object tissue surface 622.

In other words, due to the suction operation of step S12, the object tissue enters the inside of the distal end opening 609b of the suction sheath 609, and the operator presses the distal end face 621 that has slidingly moved towards the distal end-side against the object tissue that has entered the inside of the distal end opening 609b to bring the distal end face 621 into close contact with the object tissue surface 622 to achieve a state such as shown in FIG. 51.

In this state, a portion of the object tissue surface 622 opposing the distal end face 621 of the insertion portion 611 disposed at the center of the distal end opening 609b is strongly pressed against a surface of the transparent hood 623. The operator is now able to perform vascular observation in the state of step S14.

In this case, the portion opposing the distal end face 621 or, in other words, the object tissue, i.e., the fat layer portion within the observation field of view θ is uniformed and thinned, and the heat generating operation of the heat generating element 636 increases the transmittance of the fat layer portion. Consequently, the operator can set the blood vessels 641 as internal observation tissue inside the object tissue surface 622 to a readily observable state and obtain observation images.

Moreover, in the above description, a light emitting element that emits light in an infrared region can be provided on an inner side of the illuminating window at the distal end portion 630 of the insertion portion 611, whereby image pickup in the infrared region is performed under illuminating light caused by emitting light from the light emitting element.

It should be noted that the present invention is not limited to the various embodiments described above, and various modifications and applications can obviously be made without departing from the scope of the invention.

What is claimed is:

1. A scattering medium internal observation apparatus, comprising:
   a light source;
   an illuminating apparatus that guides light from the light source to an observation object that is a scattering body; and
   an observation optical system for observing the observation object illuminated by the illuminating apparatus, wherein
   the illuminating apparatus has a light-guiding member that guides light from the light source to a surface of the observation object, and
   a light-shielding member is disposed at an end portion of the light-guiding member on an observation object-side, wherein the light-shielding member covers at least a part of the surface of the observation object, and wherein the light-shielding member shields light reflected or scattered from the observation object that comes from the vicinity of the light-guiding member while at the same time not shielding light reflected or scattered from the observation object that comes from outside the vicinity of the light-guiding member.

2. The scattering medium internal observation apparatus according to claim 1, wherein the light-shielding member is arranged so as to be capable of coming into contact with the observation object.

3. The scattering medium internal observation apparatus according to claim 2, comprising a scanning apparatus that causes the light-guiding member to scan over the observation object.

4. The scattering medium internal observation apparatus according to claim 1, comprising a scanning apparatus that causes the light-guiding member to scan over the observation object.

5. The scattering medium internal observation apparatus according to claim 1, wherein the light-guiding member and the light-shielding member are integrated.

6. The scattering medium internal observation apparatus according to claim 1, wherein a plurality of the light-guiding members are provided.

7. A scattering medium internal observation apparatus, comprising:
  a light source;
  an illuminating apparatus that guides light from the light source to an observation object that is a scattering body; and
  an image pickup apparatus that picks up an image of the observation object illuminated by the illuminating apparatus, wherein
  the illuminating apparatus has a light-guiding member that guides light from the light source to a surface of the observation object, and
  a light-shielding member is disposed at an end portion of the light-guiding member on an observation object-side, wherein the light-shielding member covers at least a part of the surface of the observation object, and wherein the light-shielding member shields light reflected or scattered from the observation object that comes from the vicinity of the light-guiding member while at the same time not shielding light reflected or scattered from the observation object that comes from outside the vicinity of the light-guiding member, and
  the image pickup apparatus creates an image of a structure existing inside the observation object using light which is guided to the surface of the observation object by the light-guiding member, which is scattered inside the observation object and which is returned from a portion other than a region covered by the light-shielding member.

8. The scattering medium internal observation apparatus according to claim 7, wherein the light-shielding member is arranged so as to be capable of coming into contact with the observation object.

9. The scattering medium internal observation apparatus according to claim 8, comprising a scanning apparatus that causes the light-guiding member to scan over the observation object.

10. The scattering medium internal observation apparatus according to claim 7, comprising a scanning apparatus that causes the light-guiding member to scan over the observation object.

11. The scattering medium internal observation apparatus according to claim 7, wherein the light-guiding member and the light-shielding member are integrated.

12. The scattering medium internal observation apparatus according to claim 7, wherein a plurality of the light-guiding members are provided.

13. A scattering medium internal observation apparatus, comprising:
  a light source;
  an illuminating apparatus that guides light from the light source to an observation object that is a scattering body; and
  an observation optical system for observing the observation object illuminated by the illuminating apparatus, wherein
  the illuminating apparatus has a light-guiding member that guides light from the light source to the inside of the observation object, and
  a light-shielding member is disposed at an end portion of the light-guiding member on an observation object-side, wherein the light-shielding member covers at least a part of the surface of the observation object, and wherein the light-shielding member shields light reflected or scattered from the observation object that comes from the vicinity of the light-guiding member of the observation object while at the same time not shielding light reflected or scattered from the observation object that comes from outside the vicinity of the light-guiding member.

14. The scattering medium internal observation apparatus according to claim 13, wherein the observation object-side end portion of the light-guiding member is housed inside a hollow needle-like member at least a distal end of which is to be inserted into the observation object.

15. The scattering medium internal observation apparatus according to claim 14, wherein the light-shielding member configures a stopper that regulates an ingression amount of the hollow needle-like member or the light-guiding member into the inside of the observation object.

16. The scattering medium internal observation apparatus according to claim 15, wherein the light-shielding member is arranged so as to be positionally adjustable with respect to the light-guiding member.

17. The scattering medium internal observation apparatus according to claim 13, wherein the observation object-side distal end portion of the light-guiding member is formed in a needle-like shape.

18. The scattering medium internal observation apparatus according to claim 17, wherein the light-shielding member configures a stopper that regulates an ingression amount of the hollow needle-like member or the light-guiding member into the inside of the observation object.

19. The scattering medium internal observation apparatus according to claim 18, wherein the light-shielding member is arranged so as to be positionally adjustable with respect to the light-guiding member.

20. The scattering medium internal observation apparatus according to claim 13, wherein the light-guiding member and the light-shielding member are integrated.

21. The scattering medium internal observation apparatus according to claim 13, wherein a plurality of the light-guiding members are provided.

22. A scattering medium internal observation apparatus, comprising:
  a light source;
  an illuminating apparatus that guides light from the light source to an observation object that is a scattering body; and
  an image pickup apparatus that picks up an image of the observation object illuminated by the illuminating apparatus, wherein
  the illuminating apparatus has a light-guiding member that guides light from the light source to the inside of the observation object,
  a light-shielding member disposed at an end portion of the light-guiding member on an observation object-side, wherein the light-shielding member covers at least a part of the surface of the observation object, and wherein the light-shielding member shields light reflected or scattered from the observation object that comes from the vicinity of the light-guiding member while at the same time not shielding light reflected or scattered from the observation object that comes from outside the vicinity of the light-guiding member, and the image pickup apparatus creates an image of a structure existing inside the observation object using light which is guided to the inside of the observation object by the light-guiding member, which is scattered inside the observation object and which is returned from a portion other than a region covered by the light-shielding member.

23. The scattering medium internal observation apparatus according to claim 22, wherein the observation object-side end portion of the light-guiding member is housed inside a hollow needle-like member at least a distal end of which is to be inserted into the observation object.

24. The scattering medium internal observation apparatus according to claim 23, wherein the light-shielding member configures a stopper that regulates an ingression amount of the hollow needle-like member or the light-guiding member into the inside of the observation object.

25. The scattering medium internal observation apparatus according to claim 24, wherein the light-shielding member is arranged so as to be positionally adjustable with respect to the light-guiding member.

26. The scattering medium internal observation apparatus according to claim 22, wherein the observation object-side distal end portion of the light-guiding member is formed in a needle-like shape.

27. The scattering medium internal observation apparatus according to claim 26, wherein the light-shielding member configures a stopper that regulates an ingression amount of the hollow needle-like member or the light-guiding member into the inside of the observation object.

28. The scattering medium internal observation apparatus according to claim 27, wherein the light-shielding member is arranged so as to be positionally adjustable with respect to the light-guiding member.

29. The scattering medium internal observation apparatus according to claim 22, wherein the light-guiding member and the light-shielding member are integrated.

30. The scattering medium internal observation apparatus according to claim 22, wherein a plurality of the light-guiding members are provided.

31. An image pickup system, comprising:
an illuminating apparatus that illuminates a sample with a pulsed illuminating light, the illuminating light including at least an infrared wavelength component;
an image pickup apparatus that picks up an image of light from the sample illuminated by the illuminating apparatus; and
a timing control apparatus that controls an image pickup timing of the image pickup apparatus, wherein
the timing control apparatus is configured so as to control an irradiating interval of the illuminating apparatus relative to an image pickup interval of the image pickup apparatus, and
wherein the timing control apparatus is configured to send, to the image pickup apparatus, an image pickup timing signal that causes an image to be picked up after a predetermined time lag from an end of an irradiating timing of the illuminating apparatus during a period of non-illumination by the illuminating apparatus so that an image of at least a portion of unnecessary scattered light occurring at the sample illuminated by the illuminating apparatus is not picked up.

32. The image pickup system according to claim 31, wherein the timing control apparatus sets an amount of time lag between the irradiating timing and the image pickup timing to an arbitrary initial value and causes the image pickup apparatus to perform preliminary image pickup, and subsequently varies the amount of time lag based on a result of the image pickup in order to optimize a state of scattered light removal from a pickup image of the image pickup apparatus.

33. The image pickup system according to claim 32, wherein if
d denotes a spatial deviation between an illuminating range of the illuminating apparatus at the sample surface and an image pickup range of the image pickup apparatus,
z denotes a distance from the sample surface to the observation object site in the depth direction,
n denotes a refractive index of the sample, and c denotes the speed of light through air,
the timing control apparatus controls the image pickup timing so that image pickup is not performed on light exiting the sample at least before a time period $\Delta t$ provided by the following formula elapses after the illuminating light is incident to the sample $$\Delta t = n(z + \sqrt{d^2 + z^2})/c.$$

34. The image pickup system according to claim 31, wherein if
d denotes a spatial deviation between an illuminating range of the illuminating apparatus at the sample surface and an image pickup range of the image pickup apparatus,
z denotes a distance from the sample surface to the observation object site in the depth direction,
n denotes a refractive index of the sample, and c denotes the speed of light through air,
the timing control apparatus controls the image pickup timing so that image pickup is not performed on light exiting the sample at least before a time period $\Delta t$ provided by the following formula elapses after the illuminating light is incident to the sample $$\Delta t = n(z + \sqrt{d^2 + z^2})/c.$$

35. The image pickup system according to claim 31, wherein distances of the illuminating apparatus and the image pickup apparatus with respect to the sample are arranged so as to be fixable.

36. An image pickup system, comprising:
an illuminating apparatus that illuminates a sample with a pulsed illuminating light, the illuminating light including at least an infrared wavelength component;
an image pickup apparatus that picks up an image of light from the sample illuminated by the illuminating apparatus;
a shutter apparatus disposed either inside the image pickup apparatus or between the image pickup apparatus and the sample; and
a timing control apparatus that controls a shutter timing of the shutter apparatus, wherein
the timing control apparatus is configured so as to control an irradiating interval of the illuminating apparatus relative to a shutter interval of the shutter apparatus, and wherein the timing control apparatus is configured to send, to the shutter apparatus, a shutter timing signal that causes the shutter apparatus to operate after a predetermined time lag from an end of an irradiating timing of the illuminating apparatus during a period of non-illumination by the illuminating apparatus so that an image of at least a portion of unnecessary scattered light occurring at the sample illuminated by the illuminating apparatus is not picked up.

37. The image pickup system according to claim 36, wherein
the timing control apparatus sets an amount of time lag between the irradiating timing and the shutter timing to an arbitrary initial value and causes the image pickup apparatus to perform preliminary image pickup, and subsequently
varies the amount of time lag based on a result of the image pickup in order to optimize a state of scattered light removal from a pickup image of the image pickup apparatus.

38. The image pickup system according to claim 37, wherein if
d denotes a spatial deviation between an illuminating range of the illuminating apparatus at the sample surface and an image pickup range of the image pickup apparatus,
z denotes a distance from the sample surface to the observation object site in the depth direction,
n denotes a refractive index of the sample, and c denotes the speed of light through air,
the timing control apparatus controls the shutter timing so that image pickup is not performed on light exiting the sample at least before a time period Δt provided by the following formula elapses after the illuminating light is incident to the sample $$\Delta t = n\left(z + \sqrt{d^2 + z^2}\right)/c.$$

39. The image pickup system according to claim 36, wherein if
d denotes a spatial deviation between an illuminating range of the illuminating apparatus at the sample surface and an image pickup range of the image pickup apparatus,
z denotes a distance from the sample surface to the observation object site in the depth direction,
n denotes a refractive index of the sample, and c denotes the speed of light through air,
the timing control apparatus controls the shutter timing so that image pickup is not performed on light exiting the sample at least before a time period Δt provided by the following formula elapses after the illuminating light is incident to the sample $$\Delta t = n\left(z + \sqrt{d^2 + z^2}\right)/c.$$

40. The image pickup system according to claim 36, wherein an irradiating interval of the illuminating apparatus and the shutter interval of the shutter apparatus are arranged so as to be adjustable.

41. The image pickup system according to claim 36, wherein distances of the illuminating apparatus and the image pickup apparatus with respect to the sample are arranged so as to be fixable.

42. An image pickup method using an illuminating apparatus that illuminates a sample with an illuminating light and an image pickup apparatus that picks up an image of light from the sample illuminated by the illuminating apparatus, wherein the illuminating light includes at least an infrared wavelength component and wherein the image pickup method:
causes the illuminating apparatus to repetitively irradiate the illuminating light in a pulsed form;
correlates an irradiating interval of the illuminating apparatus with an image pickup interval of the image pickup apparatus; and
causes an image pickup timing of the image pickup apparatus to be delayed by a predetermined time period from an end of an irradiating timing of the illuminating apparatus during a period of non-illumination by the illuminating apparatus so that an image of at least a portion of unnecessary scattered light occurring at the sample illuminated by the illuminating apparatus is not picked up.

43. The image pickup method according to claim 42, wherein
after setting an amount of time lag between the irradiating timing and the image pickup timing to an arbitrary initial value and causing the image pickup apparatus to perform preliminary image pickup,
the amount of time lag based on a result of the image pickup is varied in order to optimize a state of scattered light removal from a pickup image of the image pickup apparatus.

44. The image pickup method according to claim 43, wherein if
d denotes a spatial deviation between an illuminating range of the illuminating apparatus at the sample surface and an image pickup range of the image pickup apparatus,
z denotes a distance from the sample surface to the observation object site in the depth direction,
n denotes a refractive index of the sample, and c denotes the speed of light through air,
the image pickup timing is controlled so that image pickup is not performed on light exiting the sample at least before a time period Δt provided by the following formula elapses after the illuminating light is incident to the sample $$\Delta t = n\left(z + \sqrt{d^2 + z^2}\right)/c.$$

45. The image pickup method according to claim 42, wherein if
d denotes a spatial deviation between an illuminating range of the illuminating apparatus at the sample surface and an image pickup range of the image pickup apparatus,
z denotes a distance from the sample surface to the observation object site in the depth direction,
n denotes a refractive index of the sample, and c denotes the speed of light through air,
the image pickup timing is controlled so that image pickup is not performed on light exiting the sample at least before a time period Δt provided by the following formula elapses after the illuminating light is incident to the sample $$\Delta t = n(z + \sqrt{d^2 + z^2})/c.$$

46. The image pickup method according to claim 42, wherein image pickup by the image pickup apparatus is performed in a state where distances of the illuminating apparatus and the image pickup apparatus with respect to the sample are fixed.

47. An image pickup method using an illuminating apparatus that illuminates a sample with an illuminating light, an image pickup apparatus that picks up an image of light from the sample illuminated by the illuminating apparatus, and a shutter apparatus disposed either inside the image pickup apparatus or between the image pickup apparatus and the sample, wherein the illuminating light includes at least an infrared wavelength component and wherein the image pickup method:
  causes the illuminating apparatus to repetitively irradiate the illuminating light in a pulsed form;
  correlates an irradiating interval of the illuminating apparatus with a shutter interval of the shutter apparatus; and
  causes a shutter timing of the shutter apparatus to be delayed by a predetermined time period from an end of an irradiating timing of the illuminating apparatus during a period of non-illumination by the illuminating apparatus so that an image of at least a portion of unnecessary scattered light occurring at the sample illuminated by the illuminating apparatus is not picked up.

48. The image pickup method according to claim 47, wherein
  after setting an amount of time lag between the irradiating timing and the shutter timing to an arbitrary initial value and causing the image pickup apparatus to perform preliminary image pickup,
  the amount of time lag based on a result of the image pickup is varied in order to optimize a state of scattered light removal from a pickup image of the image pickup apparatus.

49. The image pickup method according to claim 48, wherein if
  d denotes a spatial deviation between an illuminating range of the illuminating apparatus at the sample surface and an image pickup range of the image pickup apparatus,
  z denotes a distance from the sample surface to the observation object site in the depth direction,
  n denotes a refractive index of the sample, and c denotes the speed of light through air,
  the shutter timing is controlled so that image pickup is not performed on light exiting the sample at least before a time period Δt provided by the following formula elapses after the illuminating light is incident to the sample $$\Delta t = n(z + \sqrt{d^2 + z^2})/c.$$

50. The image pickup method according to claim 46, wherein if
  d denotes a spatial deviation between an illuminating range of the illuminating apparatus at the sample surface and an image pickup range of the image pickup apparatus,
  z denotes a distance from the sample surface to the observation object site in the depth direction,
  n denotes a refractive index of the sample, and c denotes the speed of light through air,
  the shutter timing is controlled so that image pickup is not performed on light exiting the sample at least before a time period Δt provided by the following formula elapses after the illuminating light is incident to the sample $$\Delta t = n(z + \sqrt{d^2 + z^2})/c.$$

51. The image pickup method according to claim 47, wherein an irradiating interval of the illuminating apparatus and the shutter interval of the shutter apparatus are adjusted and optimized in accordance with image pickup conditions of the image pickup apparatus.

52. The image pickup method according to claim 47, wherein image pickup by the image pickup apparatus is performed in a state where distances of the illuminating apparatus and the image pickup apparatus with respect to the sample are fixed.

53. An image pickup system, comprising:
  an illuminating section for irradiating an illuminating light having a predetermined wavelength band which at least exceeds a wavelength of 1200 nm to a living body tissue;
  a reflected light suppressing section configured, when the reflected light suppressing section is disposed in contact with a surface of the living body tissue, to shield, among illuminating light irradiated to the living body tissue, reflected light reflected off of a first living body tissue existing in the vicinity of a surface of the living body tissue and to pass among the illuminating light, reflected light reflected off of a second living body tissue that exists inside the living body tissue in a state where at least a portion of the second living body tissue is covered by the first living body tissue;
  an image pickup section that is sensitive in at least an infrared region whose wavelength exceeds 1200 nm and which picks up an image of the living body tissue based on reflected light reflected off of the second living body tissue; and
  a positioning section for maintaining a constant predetermined distance between the reflected light suppressing section and the image pickup section by fixing a position on the surface of the living body tissue at which the reflected light suppressing section is disposed.

54. The image pickup system according to claim 53, further comprising spectroscopic section for passing only light of a predetermined wavelength band.

55. The image pickup system according to claim 54, wherein the first living body tissue is fat.

56. The image pickup system according to claim 55, wherein the second living body tissue is a blood vessel.

57. The image pickup system according to claim 56, wherein the predetermined wavelength band is a wavelength band including a wavelength at which a difference between an optical transmittance of the first living body tissue and an optical transmittance of the second living body tissue becomes maximum.

58. The image pickup system according to claim 55, wherein the predetermined wavelength band is a wavelength band including a wavelength at which a difference between an optical transmittance of the first living body tissue and an optical transmittance of the second living body tissue becomes maximum.

59. The image pickup system according to claim 54, wherein the second living body tissue is a blood vessel.

60. The image pickup system according to claim 59, wherein the predetermined wavelength band is a wavelength band including a wavelength at which a difference between an optical transmittance of the first living body tissue and an optical transmittance of the second living body tissue becomes maximum.

61. The image pickup system according to claim 54, wherein the predetermined wavelength band is a wavelength band including a wavelength at which a difference between an optical transmittance of the first living body tissue and an optical transmittance of the second living body tissue becomes maximum.

62. The image pickup system according to claim 53, wherein the first living body tissue is fat.

63. The image pickup system according to claim 62, wherein the second living body tissue is a blood vessel.

64. The image pickup system according to claim 63, wherein the predetermined wavelength band is a wavelength band including a wavelength at which a difference between an optical transmittance of the first living body tissue and an optical transmittance of the second living body tissue becomes maximum.

65. The image pickup system according to claim 62, wherein the predetermined wavelength band is a wavelength band including a wavelength at which a difference between an optical transmittance of the first living body tissue and an optical transmittance of the second living body tissue becomes maximum.

66. The image pickup system according to claim 53, wherein the second living body tissue is a blood vessel.

67. The image pickup system according to claim 66, wherein the predetermined wavelength band is a wavelength band including a wavelength at which a difference between an optical transmittance of the first living body tissue and an optical transmittance of the second living body tissue becomes maximum.

68. The image pickup system according to claim 53, wherein the predetermined wavelength band is a wavelength band including a wavelength at which a difference between an optical transmittance of the first living body tissue and an optical transmittance of the second living body tissue becomes maximum.

69. An image pickup system, comprising:
an illuminating section capable of irradiating to a living body tissue a plurality of illuminating lights respectively having wavelength bands that differ from each other in at least a wavelength band equal to or greater than 1000 nm;
an image pickup section that is sensitive in at least a wavelength band equal to or greater than 1000 nm and which picks up living body tissue images respectively illuminated by the plurality of illuminating lights;
a luminance value comparing section for detecting luminance values of a plurality of images corresponding to the plurality of living body tissue images picked up by the image pickup section and for comparing, based on the detection results, differences in luminance values between a predetermined living body tissue image and an image other than the predetermined living body tissue for each of the plurality of images;
an image extracting section for extracting a single image with maximum difference in luminance values among the plurality of images; and
an illumination selecting section for selecting, based on information regarding the single image, a single illuminating light having a single wavelength band that enables an image having a difference in luminance values similar to the single image to be obtained among the plurality of illuminating lights respectively having wavelength bands that differ from each other.

70. The image pickup system according to claim 69, wherein the predetermined living body tissue is a blood vessel.

71. The image pickup system according to claim 70, wherein the plurality of illuminating lights are lights including at least a wavelength at which an optical transmittance of the predetermined living body tissue is equal to or lower than an optical transmittance of fat.

72. The image pickup system according to claim 71, wherein the illuminating section is capable of irradiating illuminating light having a wavelength band ranging from 1400 nm to 1500 nm.

73. The image pickup system according to claim 71, wherein the illuminating section is capable of irradiating illuminating light having a wavelength band ranging from 1900 nm to 2000 nm.

74. The image pickup system according to claim 70, wherein the illuminating section is capable of irradiating illuminating light having a wavelength band ranging from 1400 nm to 1500 nm.

75. The image pickup system according to claim 70, wherein the illuminating section is capable of irradiating illuminating light having a wavelength band ranging from 1900 nm to 2000 nm.

76. The image pickup system according to claim 69, wherein the plurality of illuminating lights are lights including at least a wavelength at which an optical transmittance of the predetermined living body tissue is equal to or lower than an optical transmittance of fat.

77. The image pickup system according to claim 76, wherein the illuminating section is capable of irradiating illuminating light having a wavelength band ranging from 1400 nm to 1500 nm.

78. The image pickup system according to claim 76, wherein the illuminating section is capable of irradiating illuminating light having a wavelength band ranging from 1900 nm to 2000 nm.

79. The image pickup system according to claim 69, wherein the illuminating section is capable of irradiating illuminating light having a wavelength band ranging from 1400 nm to 1500 nm.

80. The image pickup system according to claim 69, wherein the illuminating section is capable of irradiating illuminating light having a wavelength band ranging from 1900 nm to 2000 nm.

* * * * *

UNITED STATES PATENT AND TRADEMARK OFFICE
CERTIFICATE OF CORRECTION

PATENT NO. : 8,259,167 B2
APPLICATION NO. : 12/207239
DATED : September 4, 2012
INVENTOR(S) : Hiroshi Ishiwata et al.

It is certified that error appears in the above-identified patent and that said Letters Patent is hereby corrected as shown below:

Column 65, line 50 (claim 50, line 1) Should read: The image pickup method according to claim 47

Signed and Sealed this
Eighth Day of January, 2013

David J. Kappos
*Director of the United States Patent and Trademark Office*